US006242714B1

US 6,242,714 B1

(12) United States Patent
Narumiya et al.

(10) Patent No.: US 6,242,714 B1
(45) Date of Patent: Jun. 5, 2001

(54) NONCONTACT ARTICLE TEMPERATURE MEASURING DEVICE FOR FOOD

(75) Inventors: Tadaoki Narumiya; Eiji Kato; Tomoko Maeda, all of Tokyo; Yoshio Hagura, Hiroshima, all of (JP)

(73) Assignee: Mayekawa Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/530,358

(22) PCT Filed: Sep. 2, 1999

(86) PCT No.: PCT/JP99/04749

§ 371 Date: Jul. 21, 2000

§ 102(e) Date: Jul. 21, 2000

(87) PCT Pub. No.: WO00/14522

PCT Pub. Date: Mar. 16, 2000

(30) Foreign Application Priority Data

Sep. 2, 1998 (JP) .................................................. 10-247875

(51) Int. Cl.[7] .............................. F27D 11/00; G01K 1/08; A01J 11/04
(52) U.S. Cl. .............................. 219/385; 374/149; 99/467
(58) Field of Search .................................. 219/385, 520; 99/325, 483; 426/384; 62/532, 353, 324; 374/177, 184, 149; 361/266, 282; 501/10, 73

(56) References Cited

U.S. PATENT DOCUMENTS

| 3,649,891 | * | 3/1972 | Lawless | 361/276 |
| 3,759,104 | * | 9/1973 | Robinson | 374/177 |
| 4,164,147 | * | 8/1979 | Kulwicki et al. | 374/170 |
| 4,734,553 | * | 3/1988 | Noda | 219/710 |

(List continued on next page.)

FOREIGN PATENT DOCUMENTS

| 58-083263A | 5/1983 | (JP) . |
| 63-298143A | 12/1988 | (JP) . |
| 4-073582A | 3/1992 | (JP) . |

OTHER PUBLICATIONS

Japanese Patent Gazette No. 4511271, entitled "Freeze Sensor", published Apr. 23, 1970.

Primary Examiner—Teresa Walberg
Assistant Examiner—Daniel Robinson
(74) Attorney, Agent, or Firm—Evenson, McKeown, Edwards & Lenahan, P.L.L.C.

(57) ABSTRACT

A noncontact article temperature measuring device adapted for evaluating the quality including the food temperature, freezed/thawed state, presence/absence of bubble based on food capacitance measurement data and for evaluating/controlling the operation of a thawing device and used for a freezing/thawing system so as to solve conventional problems. The measuring device is so provided that an article of food can be passed or is provided on both vertical sides of a space or on the same plane of one of the sides. The measuring device comprises at least a pair of electrodes serving as a capacitance sensor and a capacitance measuring section for measuring the capacitance of the food article placed in the space from the signal generated by the paired electrodes. The capacitance is measured by applying a predetermined voltage between the electrodes, and the temperature of the article is determined and the freezed/thawed state is recognized from the measured capacitance. The voltage applied to the plus electrode is preferably a high-frequency voltage the frequency of which ranges from 50 kHz to 1 MHz. A guard electrode for preventing lines of electric force from diffusing surrounds the plus electrode at an insulation distance is preferably provided.

19 Claims, 43 Drawing Sheets

U.S. PATENT DOCUMENTS

| | | | |
|---|---|---|---|
| 4,857,686 | * | 8/1989 | Hirata et al. .......................... 219/710 |
| 4,883,366 | * | 11/1989 | Dohi et al. ............................ 374/184 |
| 4,920,450 | * | 4/1990 | Masiulis ............................... 361/282 |
| 5,036,172 | * | 7/1991 | Kokkeler et al. .................... 219/703 |
| 5,237,142 | * | 8/1993 | Cigarini et al. ...................... 219/708 |
| 5,407,276 | * | 4/1995 | Jones .................................... 374/184 |
| 5,483,414 | * | 1/1996 | Turtiainen ............................ 361/282 |
| 5,635,812 | * | 6/1997 | Eschbach et al. ....................... 320/1 |
| 5,788,376 | * | 8/1998 | Sultan et al. ......................... 374/184 |
| 5,796,081 | * | 8/1998 | Carlsson et al. ..................... 219/711 |

* cited by examiner

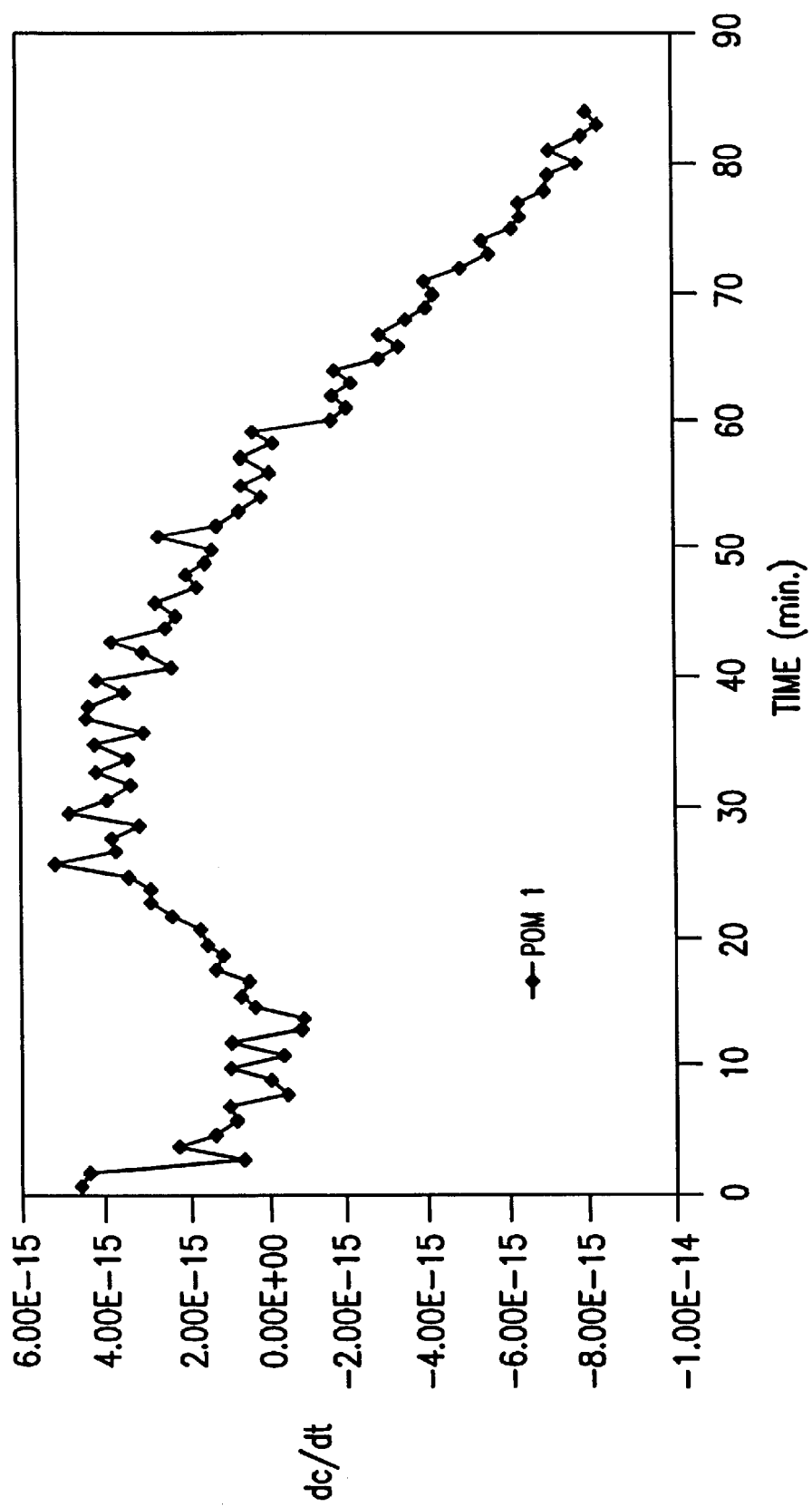

NONCONTACT ARTICLE TEMPERATURE MEASURING DEVICE FOR FOOD

FIELD OF THE INVENTION

The present invention relates to a noncontact article temperature measuring device for food based on capacity measurement of food article such as frozen hamburger, frozen meatball, and processed food, for enabling the production of homogeneous and high quality processed food and frozen food, specifically to a noncontact article temperature measuring device used for a freezing/thawing system in which the evaluation of qualities including article temperature, frozen/thawed state of food, presence/absence of bubble in food, and also the evaluation/control of operation of a thawing device are possible according to the measurement data.

Here, the article temperature of food includes quality evaluation such as the temperature, frozen/thawed state of food, and presence/absence of bubble in food.

BACKGROUND ART

Food, when frozen, can be preserved over a prolonged period by retarded biochemical reaction along with suppressed action of microorganism under decreased activity of water in the food owing to low temperature and freezing of the water contained in the food. The limit temperature for multiplication of microbe is about −10° C., and that of yeast is about −18° C.

It is said, therefore, that food is unlikely to be rotten or decomposed by self digestion when refrigerated under −18° C. (deep frozen state).

According to the Japanese Agricultural Standard, freezing method of processed food article such as hamburger and meatball should be such that the food article are rapidly passed through a temperature range from −1° C. to −5° C. which is the maximum ice-crystal formative temperature range in which most part of the water in the food freezes, to be frozen to −18° C.

Water contained in food comprises free water which can move freely and easy to be frozen and bound water which is hard to be frozen. The latter is the water in hydrated molecule of protein, glycogen, etc. and the higher the degree of hydration is, the harder it is to be frozen. So it is the free water in food that forms ice-crystal when the food is frozen. When food is cooled to freezing point, ice separates as crystal in the water solution in the food. When the food is further cooled below freezing point to the maximum ice-crystal formative temperature range (temperature range from −1° C. to −6° C. in the case freezing point of the food is −1° C.), ice-crystal grows in this temperature range, which causes the destruction of cell membrane. Therefore, it is desired that minute ice-crystals are separated by quick freezing in which the food is cooled passing through the maximum ice-crystal formative temperature range in short time so as to restrain the physical destruction of cells to the minimum.

It is also said that frost damage does not occur in the case where freezing is performed in a way in which, as even in the case of the said quick freezing a lot of small ice-crystals are formed in and outside of a cell and destruct the cell, this phenomenon is prevented by restraining initial freezing speed to a degree the separation of ice-crystal in the cell does not occur and shifting to quick freezing after the outside of the cell is solidified with ice-crystals.

For the operation without frost damage like this, it is necessary to know accurately an ever-changing temperature of food during freezing and to control freezing through programmed control responding to the change of the temperature.

Also, the uniformization of uneven temperature in a food article from the surface to deep part caused by quick freezing is necessary to be performed by interposing a temperature uniformizing freezing process between the said quick freezing and deep freezing (freezing to a temperature under the maximum ice-crystal formative temperature, for example, to a neighborhood of −20° C.), which temperature uniformizing freezing is possible by the change of freezing medium and freezing condition.

In this case also accurate understanding of food temperature and programmed control of freezing based on the understood measured food temperature is necessary.

It is said that, particularly in the freezing process of a cooked food article, the physical damage of fleshy or pulpy substance should be minimized by obtaining finer ice-crystal in quick freezing to minimize the physical and chemical influences to the composition of the food and then storage in low temperatures under −18° C. with small deviation of ±2° C. is necessary lest the growth of ice-crystal does not proceed fast during the storage.

In an individual freezing in which small sized food articles are individually frozen, it is necessary to measure the surface, center, and balanced temperature of each food article, to draw up their freezing curves, to freeze under an appropriate condition of freezing environment temperature, freezing speed, etc., and to check food temperature after freezing.

In unfreezing of food, rapid passing through the maximum ice-crystal thawing zone by rapid unfreezing is required, in the point of view of biochemical and enzymatic reaction, to keep the food temperature under −10° C., possibly under −5° C., until the food temperature is raised to 0° C. That is, also in this case, an unfreezing with high temperature at initial stage and then a programmed unfreezing with low temperature is required.

It is important to efficiently produce with low mortality homogeneous and high quality frozen food articles, that various states of the food such as temperature, temperature decreasing speed, freezing speed, completion of freezing, shape, size, composition, and in the case of continuous cooling/freezing/heating apparatus, arrangement on the transfer belt and transfer speed, are grasped and the most suitable and efficient operation for freezing the food is performed.

By the way, hitherto, the measurement of the temperature of a food article in freezing or unfreezing process has been performed by measuring the temperature of the surrounding air, water, or brine which comes in contact with the food article, or of the surface of the food article by allowing a sensor to contact the same, or of the inside of the food article by thrusting a sensor into the same and thus the temperature of a food article has not been grasped as the whole.

In the case of measurement by thrusting a sensor, the measured food article can not be used as a product, and in the case of measurement by contacting a sensor it is unhygienic.

Further, according to the conventional method, measurement of temperatures at various parts of a number of food articles have been practically impossible and so measurement has been performed on selected parts of a small number of sampled food articles and inferences have been made from the freezing environment such as the temperature, speed, direction of the cooling air, and freezing period. The control of the operation of a freezing apparatus has been done through feedback of the data of the freezing environment not that of the data of the temperature and degree of freeze of the food articles.

In the mean time, from now, to respond to the demands from user side such as PL Act, HACCP (Hazard Analysis and Critical Control Point), cost down, and differentiation of product with high added values, the quality control and operation control with high accuracy will be indispensable. However, by conventional method, a variety of sensors and measurement devices such as; for example, contact and/or insert temperature sensor; radiation surface thermometer; chemical and physical analyzer of sampled piece of food; X-ray or radiologic, magnetic, supersonic, photoelectronic devices; image sensor; touch sensor; have been used in accordance with increasing measurement items, and there have occurred problems such as the complication of apparatus and its operation, increase in the number of samples, and increase of work for caring sensors.

The most crucial point is the problem of hygienic quality of food article due to contacting of sensors with the food article.

For example, when measuring the temperature of a food article with a thermistor and so forth, the tip of the sensor must be inserted into the food article and so the sensor itself must be kept in a germ-free condition. Further, when a number of food articles are continuously transferred on the conveyor of a continuous freezing apparatus and so forth, it is impossible to measure the temperature of the food articles individually with thermistor and so forth.

An invention which, in a heat source apparatus for hydrous food, using as temperature detecting means a means for detecting impedance which varies with the temperature of the food due to the change of conductivity and permittivity of the same placed on a pair of electrodes formed on a base plate, performs chilled/partial control of the heat source apparatus, based on the detected value, is disclosed in Japanese Patent Publication No. 7-76664.

In the invention mentioned above, impedance is measured, placing a food on the pair of electrodes, but the state of contact of the food with the electrodes and the contact resistance are not constant and the measurement is always performed in an unstable condition and so the measurement value is inaccurate, therefore, the control of the heat source apparatus with high accuracy based on the measurement value can not be expected.

Conventionally, to grasp the various states of a food article, a variety of sensors are used, but with positions of sensors fixed, the temperatures of the food article can not be measured accurately when food articles of various size are transferred in a continuous freezing apparatus.

The present invention was made in light of such problems as mentioned above, and inventors took notice of the fact that the change in physical properties and composition of a food due to bonding/separation of water, change in molecular structure, and etc., caused by the freezing and unfreezing of the food, causes a change in permittivity of the food and the change in the permittivity correlates with the change in the capacitance between a pair of electrodes holding the food article in between without contact with them.

It is thinkable that the temperature of a food article in a frozen or unfrozen state correlates with the capacitance between the electrodes, and particularly at freeze point at which the physical properties of food change largely, change in the electrostatic capacity occurs owing to the change in physical properties of the food in accordance with the temperature of the same.

The object of the present invention is to provide a non-contact article temperature measuring device applicable to a freezing/unfreezing system which enables the evaluation of quality including the food temperature, frozen/thawed state, and presence/absence of bubble, and also enables the operation control of the unfreezing apparatus.

SUMMARY OF THE INVENTION

The present invention is constructed as described hereinbelow to solve the technical problems mentioned above.

The invention of claim 1 is characterized in that; at least a pair of electrodes serving as a capacitance sensor, facing each other vertically across a space to compose a capacitance sensor, through or in which space an article of food is passed or placed, and a capacitance measuring section for determining the capacitance of the food article located in the said space from the electric signal obtained from the pair of electrodes, are provided; and the determination of the article temperature including the food temperature, or frozen/thawed state, based on the detected capacitance when the predetermined voltage is applied to the paired electrodes, is made possible.

The voltage applied to the positive electrode is preferable to be that of high frequency of the range from 50 KHz to 1 MHz.

It is preferable that the positive sensor electrode to which the predetermined voltage is applied is so composed that a guard electrode for preventing diffusion of lines of electric force is provided around the periphery of the positive electrode with insulation spacing kept between them, the guard electrode being grounded. In this case it is preferable that the upper and lower side of the positive sensor electrode are coated with substantial electric insulating material or the positive sensor electrode is sandwiched with substantial electric insulators to be prevented from contacting with the food article and humidity which are fluctuating factors of the environment.

Simplification of the system is attained if the other electrode located opposite to the positive electrode across the said space is made of electric conductive material and constitute a part of transferring face of food articles or grounded face.

It is preferable to provide a grounded noise filter in the space above the positive electrode located on the opposite side of the space for transferring food article. In this case it is also suitable to provide the same on the opposite side of the negative electrode.

According to the present invention, measurement data at the capacitance measuring section is obtained in time sequence, and the time series data is compared with the standard data for the food article subjected to the measurement, which data is memorized in advance, to evaluate the quality of the food article such as internal deficiency and inclusion of foreign matter along with the food temperature, frozen/thawed state.

In the case the present invention is applied to a continuous freezing or unfreezing apparatus which performs continuous freezing or unfreezing of the food article transferred on the conveyor, it is preferable that at least one of the paired electrodes is an electrically conductive transfer medium which constitute a part of the food transfer conveyor and the other is an electrode or a plurality of electrodes located above and facing the former electrode across a space through or in which the food article passes or is located without contacting with the electrodes.

Further, it is preferable that the freezing/unfreezing room in which the food article is transferred by the conveyor is partitioned to a plurality of freezing/unfreezing zones, the positive electrode is provided in each zone, and on the other hand a belt-form electrode made of electric conductive material is provided on a part of the conveyor.

It is also preferable that the positive electrode of the paired electrodes is composed as multi-polar sensor electrode having poles divided in plurality and the article temperature including food temperature, or frozen/thawed state, is determined based on the signal from a selected electrode or a composite signal from combined electrodes among the plurality of the electrodes.

In this case also it is suitable that the plurality of electrodes are surrounded as a whole, with insulation spacing between them, by a grounded guard electrode for preventing lines of electric force from diffusing.

It is preferable in this case to evaluate the quality of food article such as shape and presence/absence of internal hollow by selectively combining the plurality of capacitance signals obtained through measurement in which the direction and position of the food article to be measured are changed relative to the multi-polar sensor when the food article passes by the sensor.

It is possible to arrange both the positive and negative sensor electrode (positive electrode 1a and negative one 1b) on the same plane unlike the above mentioned invention in which the positive and negative sensor electrode is disposed facing each other vertically across an article to be measured (food) in the space between the electrodes.

Particularly, this construction is preferable in the case of a continuous freezing apparatus in which the transfer table is of nonmetal or electric non-conductive belt or the belt face is considerably contaminated because the belt face acts as insulating face, and beneficial because the sensor can be used also as a noncontact sensor.

The invention of claim 13 is the one taking into consideration the point mentioned above. It is characterized in that; a substantial electric insulator, on the surface of which is disposed a food article, is provided under the lower side of the space through or in which the food article passes or placed; on the upper side of the space is provided at least a pair of electrodes serving as a capacitance sensor; a capacitance measuring section for determining the capacitance of the food article located in the said space from the electric signal obtained from the paired electrodes, is provided; and the measurement of the article temperature including the food temperature, or frozen/thawed state, based on the detected capacitance when the predetermined voltage is applied to the pair of electrodes, is made possible.

In this case also the voltage applied to the positive electrode is preferable to be that of high frequency of the range from 50 KHz to 1 MHz. Further, it is preferable that a grounded guard electrode for preventing diffusion of lines of electric force is provided around the periphery of the positive electrode with insulation spacing kept between them and further both the upper and lower face of both the positive and negative electrode are coated with substantial electric insulation material or the electrodes are sandwiched by electric insulators to be prevented from contacting with the food and humidity which are fluctuating factors of the environment.

Each of the negative electrodes located on the same plane may be grounded separately to constitute individual electrode or they may be formed to be a grounded common negative electrode corresponding to positive electrodes.

In the mean time, when a sensor is used in a freezing, unfreezing, or heating apparatus, there emerge and grow on the surface of the sensor phenomena such as dew condensation, icing, and frosting. The value of capacitance varies with the emergence and growth of these phenomena and so the accurate measurement of the capacitance of the food article is impossible. The inventions of claim 18 and 19 are those in which the air temperature in the space where capacitance sensors are located is kept a little higher (0.1° C.~10° C.) than dew point to increase saturation pressure of vapor for the prevention of dew condensation, icing, and frosting.

The invention of claim 18 is to be adapted to the invention of claim 1 and is characterized in that the device comprises; at least a pair of electrodes serving as a capacitance sensor, facing each other vertically across a space to compose a capacitance sensor, through or in which space an article food is passed or placed; a capacitance measuring section for determining the capacitance of the food article located in the space from the electric signal obtained from the paired electrodes; a means for heating the environment air in the space on the side facing the positive electrode of the paired electrodes; and that the determination of the article temperature including the food temperature, or frozen/thawed state, based on the detected capacitance, keeping the air temperature slightly higher than the dew point, is made possible.

The invention of claim 19 is to be adapted to the invention of claim 13 and is characterized in that; a substantial electric insulator on the surface of which an article of food is disposed is provided under the space through or in which the food article passes or is placed; on the upper side of the space is provided at least a pair of electrodes serving as a capacitance sensor; a capacitance measuring section for determining the capacitance of the food article located in the space from the electric signal obtained from the paired electrodes, is provided; a means for heating the environment air in the space on the side facing the positive electrode of the paired electrodes, is provided; and the determination of the article temperature including the food temperature, or frozen/thawed state, based on the detected capacitance, keeping the air temperature slightly higher than the dew point, is made possible.

A freezing/unfreezing control system using these inventions is provided with a pair of electrodes to be used as a sensor in the freezing/thawing room containing a cooling means which cools food with cooling medium and a heating means which heats food with heating medium, a non-contact article temperature measuring device having a capacitance measuring section and making it possible to detect the capacitance of the food when the predetermined voltage is applied to the paired electrodes, and a food locating means which is capable of disposing the food article without contacting with the electrodes; the capacitance measuring section being connected to an operational comparator section where the measured data from the capacitance measuring section is compared with the previously measured data of capacitance of a specific food article in the process of freezing; and further the operational comparator section is connected to an adjusting/setting section where the control of the cooling or heating medium is performed based on the result of the comparison to enable the evaluation of quality of food article.

In each of the previous inventions, the provision of a guard electrode (frame for preventing lines of electric force from diffusing) around the periphery of an electrode or surrounding electrodes with specified spacing kept between the guard electrode and the electrode or electrodes to restrain the influence due to the diffusion of lines of electric force and the provision of grounded noise filter electrodes sandwiching the paired electrodes with spacing kept between the noise filter electrodes and the paired electrodes to abate noise problems, bring about a good result.

Further, in a diversified freezing/unfreezing control system having a continuous freezing apparatus, a stainless steel belt, stainless mesh belt, and metal tray (hereinafter referred to as a belt) which are transfer medium of food are used as a negative electrode.

BRIEF DESCRIPTION OF THE DRAWINGS

FIG. 25 is a graph showing the derivative of capacitance with respect to time versus time when a hamburger is frozen.

DESCRIPTION OF THE PREFERRED EMBODIMENTS

A preferred embodiment of the present invention will now be detailed with reference to the accompanying drawings. It is intended, however, that unless particularly specified, dimensions, materials, shapes, relative positions and so forth of the constituent parts described in the embodiment shall be interpreted as illustrative only not limitative of the scope of the present invention.

Figure 1:
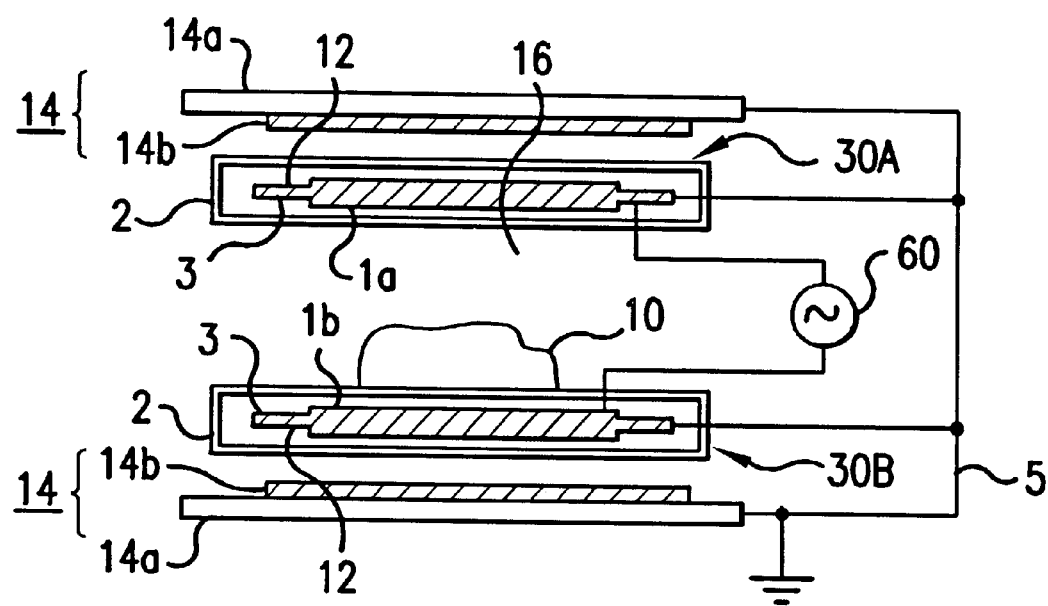
FIG. 1 is a schematic sectional view showing the basic construction of a noncontact article temperature measuring device for food according to the present invention.

FIG. 1 is a schematic sectional view showing the basic construction of a noncontact article temperature measuring device for food according to the present invention.

The noncontact article temperature measuring device for food according to the present invention is, as shown in FIG. 1 and FIG. 6, provided with a pair of sensor electrodes 30A and 30B which face vertically each other across a space 16 through or in which an article of food is passed or placed without contacting with the electrodes and constitute a noncontact capacitance sensor 30.

The upper side sensor electrode 30A is composed as positive electrode and comprises, as shown in FIG. 6 for example; a positive electrode 1a of rectangular or circular thin plate made of copper, aluminum, or other electric conductive materials; a guard electrode (frame for preventing diffusion of lines of electric force) 3 of rectangular or circular ring shape surrounding the positive electrode 1a with appropriate spacing (insulation spacing) 12; insulation sheet plates 2a, 2b for sealing and insulating wholly both the upper and lower faces with the insulation spacing 12 kept; and the signal of the detected capacitance from the positive electrode 1a is taken out by a lead wire 4 with shield covering 5.

The lower side sensor electrode 30B is composed as negative electrode and comprises, as shown in FIG. 6 for example; a negative electrode 1b of rectangular or circular thin plate made of copper, aluminum, or other electric conductive materials; a guard electrode (frame for preventing diffusion of lines of electric force) 3 of rectangular or circular ring shape surrounding the positive electrode 1b with appropriate spacing (insulation spacing) 12; insulation sheet plates 2a, 2b for sealing and insulating wholly both the upper and lower faces with the insulation spacing 12 kept; and the signal of the detected capacitance from the positive electrode 1b is taken out by a lead wire 4 with shield covering 5.

As shown in FIG. 1, noise filter 14, 14 for prevention of noise are provided above and below the sealed sensor electrodes 30A, 30B, and the two electrodes 1a, 1b are connected to a capacitance measuring section 60.

The electric capacitance sensor 30 can measure capacitance with stability by the application of high frequency voltage of about 1~50 V, 50 KHz~1 MHz. The guard electrode (frame for preventing diffusion of the line of electric force) 3 and noise filter 14, 14 are grounded for safety.

The positive electrode 1a is provided with the guard electrode 3, but the other side electrode, negative electrode, may not be provided with the same.

When one of the paired electrodes 1b is grounded, the other non-grounded electrode is provided with the guard electrode 3 and is the positive electrode 1a.

The noise filter 14 is a grounded iron member 14a with copper foil 14b affixed on it and prevents electrostatic charging from within and without, high and low frequency noise, electromagnetic wave, etc.

The shield covering 5 of lead cable 4 which shield covering is formed of copper or aluminum wire mesh is grounded to prevent measuring errs due to capacitance between cables, high and low frequency noise, electromagnetic wave, etc.

The insulation sheet plates 2a, 2b wholly envelop or sandwich the upper and lower electrode 1a, 1b and guard electrode 3 respectively to seal them so that the food 10 which is an article to be measured can be placed in a state not contacting with the electrode 1a, 1b, and 3 not destructed.

The guard electrode 3 is connected by soldering, etc. to the copper or aluminum mesh shield covering 5 (reference numeral 5 in FIG. 6) to prevent diffusion of the line of the electric force generated between the electrode 1a and 1b.

With the construction described above, when a high frequency voltage is applied between the electrode 1a and 1b via the capacitance measuring section 60, the capacitance of the condenser formed with the paired electrodes and capacitive load between the electrodes can be measured, and based on the determine capacity the balanced article temperature of the food article is computed as detailed later. Using the result, the article temperature characteristic of the food article when freezing or unfreezing can be determined, and reliable programmed control in the process of quick freezing, uniformizing freezing, deep freezing, quick unfreezing, and low temperature retaining is possible.

Next, the embodiment of the capacitance sensor shown in FIG. 1 will further be detailed with reference to FIG. 6 and FIG. 7.

FIG. 6 is a schematic illustration of a concrete form of the capacitance sensor of FIG. 1; (A) is a plan view, (B) and (C) are sections along line X—X in FIG. 1, and FIG. 7 is a side view of the assembled electrostatic capacity sensor of FIG. 1.

Figure 6A:
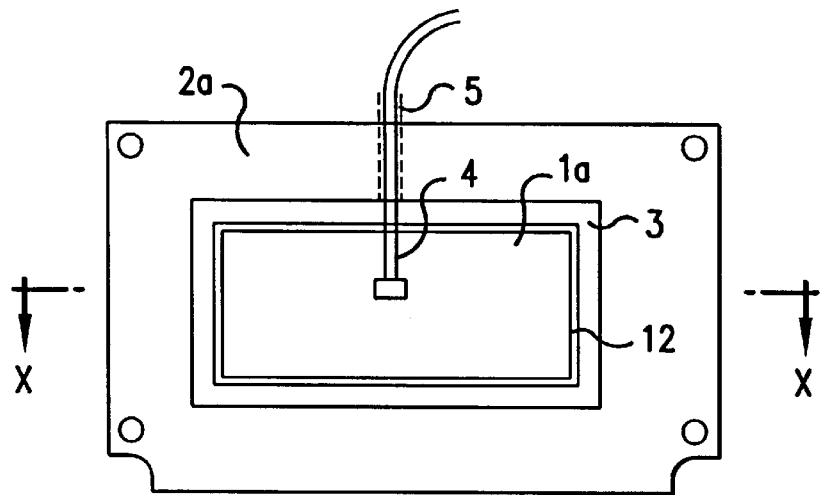
FIG. 6 is a schematic illustration of a concrete form of the capacitance sensor of FIG. 1; (A) is a plan view, (B) and (C) are sections along line X—X in FIG. 1.
Figure 6B:
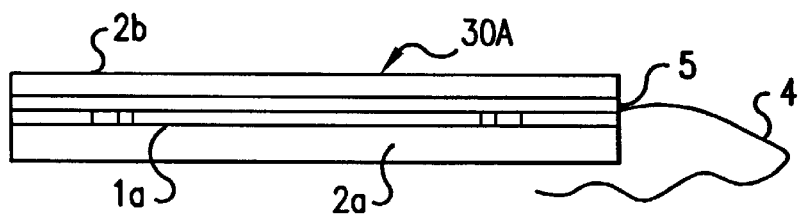

A positive sensor electrode 30A comprises an positive electrode 1a made of conductive material such as copper plate surrounded by an electric force line diffusion prevention frame 3 with a specific small spacing 12 between them, and substantial insulation plates 2a, 2b made of transparent plate of hard vinyl chloride, etc., sandwiching and fixing them to prevent lines of electric force from diffusing from the periphery of the electrode 1a. The signal corresponding to the capacitance detected at the electrode 1a is taken out by way of a lead wire 4 covered with shield covering 5 as mentioned before. Thus the capacitance sensor 30A is constructed as shown in FIG. 6(B).

The insulation plate 2a, 2b made of the same material enable the use of an adhesive which dissolve the plates to cement the both, and strong mechanical strength and good sealing are obtained.

Figure 6C:
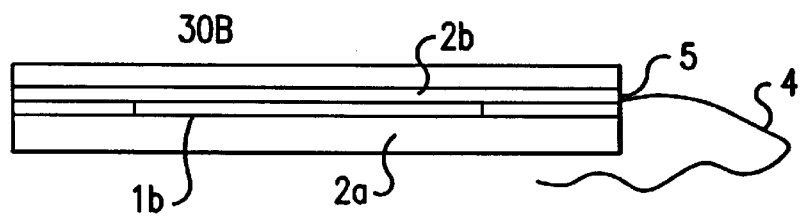

The sensor electrode 30B disposed underside is, as shown in FIG. 6(C), configured as a negative electrode (grounded electrode) and comprises; a negative electrode 1b of rectangular, thin plate made of, for example, electric conductive material such as copper, aluminum, and others; and insulation plates 2a, 2b made of transparent plate of hard vinyl chloride, etc., sandwiching the negative electrode 1b to secure sealing and insulation; and a signal corresponding to the capacitance detected at the negative electrode 1b is taken out by way of the lead wire 4 covered with the shield covering 5.

The sensor electrode 30B is composed similar to the sensor electrode 30A except that the former has no electric force line diffusion prevention frame 3. The electric force line diffusion prevention frame 3 may be provided in the sensor electrode 30B without harm.

Figure 7:
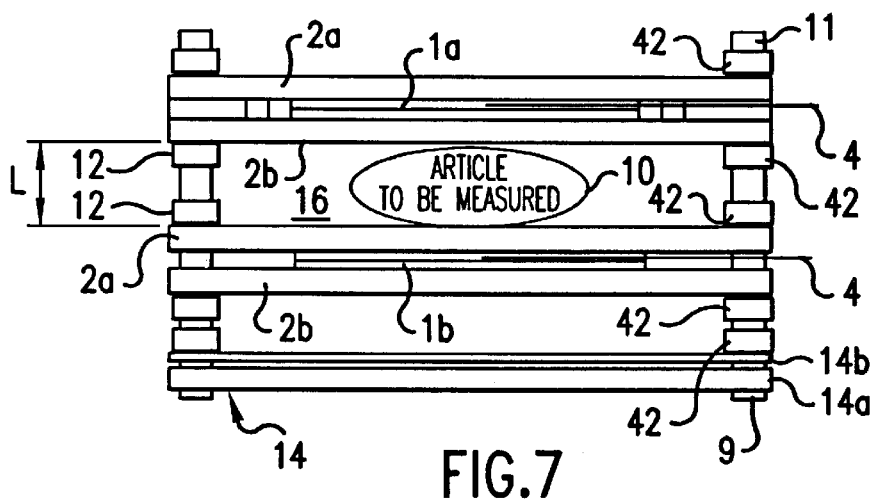
FIG. 7 is a side view of the assembled electrostatic capacity sensor of FIG. 1.

FIG. 7 is a side view of the capacitance sensor 30 used in an embodiment according to the present invention.

The two sensor electrodes 30A, 30B are disposed facing each other across a space 16 through which food, the articles to be measured, can pass without contacting with the sensor electrodes 30A, 30B, and a holder 14a of rectangular shape made of stainless steel and having the same outer dimension as the insulation plates 2a, 2b is disposed below the sensor electrode 30B. The holder 14a has screw holes 9 at the four corners.

The stainless holder 14a has a grounded copper plate 14b cemented on its upper face to constitute a noise filter 14 for shielding magnetic field, static electricity, low and high frequency electric wave, and at the same time has the thickness to support the weight of the sensor 30.

A plurality of nuts 42 are screwed on bolts 11 made of stainless steel standing upright screwed into the screw holes 9 at the four corners, and the distance L between the sensor electrode 30A and 30B is adjustable by rotating the nuts 42.

The article to be measured (food) 10 is placed in the space between the capacitance sensor electrode 30A and 30B.

Hereinbelow, apparatus A for freezing/unfreezing various kinds of foods will be described.

Figure 2:
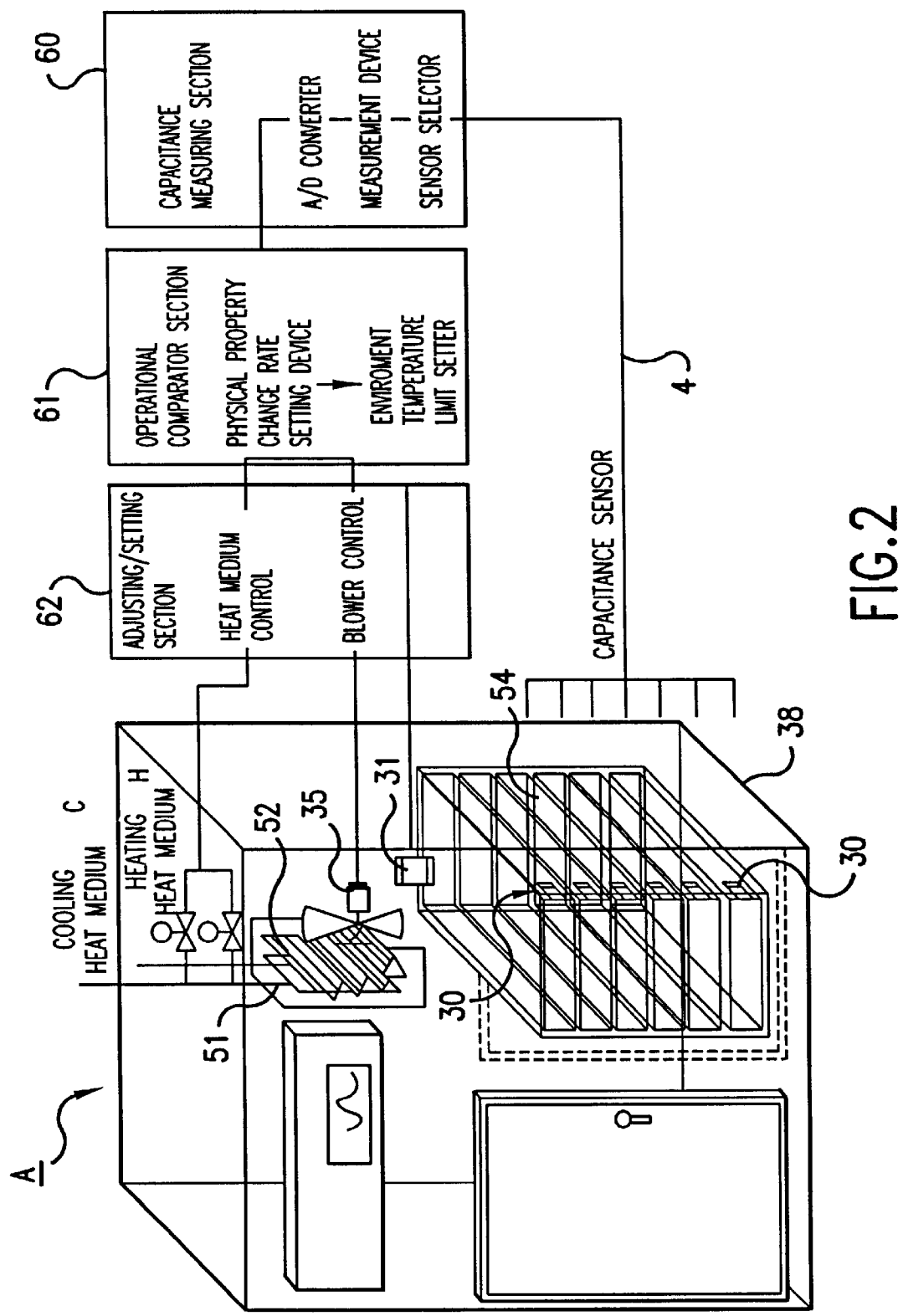
FIG. 2 is a schematic representation showing the basic configuration of a freezing/unfreezing system using a batch type freezing/unfreezing apparatus to which the device of FIG. 1 is applied.

FIG. 2 is a schematic representation showing the basic configuration of a freezing/unfreezing system using a batch type freezing/unfreezing apparatus to which the capacitance sensor shown in FIG. 1 and FIG. 7 is applied.

In the drawing, in a freezing/unfreezing room 38 are provided; a cooling means 51 comprising a heat exchanger, etc., in which cooling heat medium such as brine or refrigerant is circulated; a heating means 52 comprising heat exchanger, etc., in which heating heat medium such as heated brine is circulated; a temperature sensor 31 disposed at the upper part of a multistage container 54; the multistage container 54 in which the food article 10 to be measured are placed at the specific position on the specific stage; and a air blowing fan 35 disposed facing the cooling means 51 and heating means 52.

At each stage of the multistage container 54 which is the food laying means is located a pair of sensor electrodes 30A, 30B, each stage is arranged to keep the span so as to enable the food article 10 to be measured to be disposed without contact with the sensor electrodes 30A, 30B, and the electrostatic capacity of the food article 10 is measured by applying predetermined voltage between the sensor electrodes 30A and 30B.

The pair of electrodes 1a, 1b is connected by the lead wire 4 to the capacitance measuring section 60, and thus the noncontact article temperature measuring is possible.

The capacitance measuring section 60 comprises; a sensor selector for selecting a capacitance sensor or sensors 30 from which to take in specific data; a measurement device for measuring capacitance by applying voltage between the sensor electrodes 30A and 30B; and an A/D converter. The data measured by the capacitance measuring section 60 are sent to an operational comparator section 61, where the data is taken-in in time series by the physical property change rate setting device and the measured data of capacitance in the freezing process received from the capacitance measuring section 60 are compared with the data of capacitance of a specific food in the freezing process measured beforehand and memorized, and the comparison enables, as described later, the evaluation of the quality of the measured food article by detecting internal deficiency and inclusion of foreign matter along with the temperature and frozen state.

The quality evaluation data obtained from the operational comparator section 61 enables the control of temperature by means of controlling flow rate of the cooling heat medium (C) and the heating heat medium (H), based on the environment temperature, the standard temperature set by the limit setter, and the result of computation in the operational comparator section 61.

It is a matter of course that the freezing/unfreezing control system according to the present invention can be constituted as a combination of a freezing apparatus having freezing function only, with an unfreezing apparatus having unfreezing function only, and further with a cold storage apparatus and heating apparatus.

Figure 4:
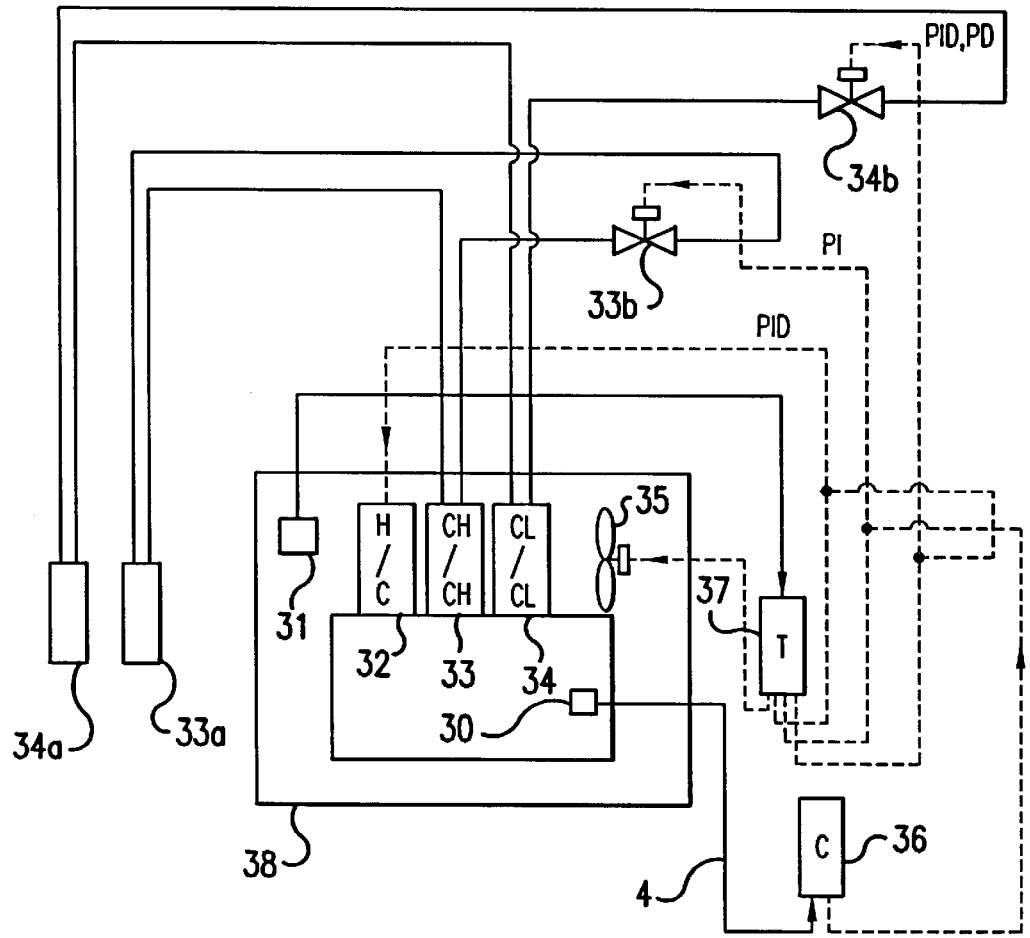
FIG. 4 is a system diagram showing the element configuration of the batch type freezing/unfreezing system.

FIG. 4 shows the configuration of elements of the batch type freezing/unfreezing system of FIG. 2. The freezing/unfreezing system includes in the freezing/unfreezing room 38 the noncontact capacity sensor 30; a temperature sensor 31 for measuring environment temperature in freezing or unfreezing; a heating source 32 comprising a heater for quick unfreezing and heat exchanger; a cooling device 33 having a single-stage compressor 33a which produces a cooling heat source for low temperature unfreezing and uniformizing freezing (cooling heat source of +20° C.~−20° C.); a cooling device 34 having a 2-stage compressor 34a which produces cooling heat source for quick freezing and deep freezing (cooling heat source of −20° C.~−60° C.); and the air blowing fan 35. The system also comprises; a main controller 36 including a CPU which performs the operational comparison 61 of the measured capacitance 60 based on the signal from the noncontact capacity sensor 30 and programmed control PI, PID; and an auxiliary controller 37 which performs the limit control of the room temperature based on the detected value of the temperature sensor 31, functioning as the temperature adjusting/setting section 62.

With large capacity of compressor any one of the single-stage compressor or the 2-stage compressor and their pertinent cooler 33 or 34 may be excluded. It is preferable to use the 2 types of compressors and coolers for stable operation and energy saving.

An example of the operation of freezing and unfreezing according to the configuration described above, is; in the case of unfreezing, in the first half of the unfreezing the maximum ice-crystal thawing zone is passed quickly by the PI control, and after the balanced article temperature of 0° C. is reached a low temperature slow unfreezing with article temperature below 10° C., possibly below 5° C. under the PI control of the cooling device 33, is performed when quick unfreezing by circulating the heating heat medium from the heating source 32; and in the case of freezing, a quick freezing with freezing temperature of under −40° C. is performed by means of the cooling device 34 under the PID control to lower the temperature at the center of the food to its freezing point, then an uniformization freezing is performed by means of the cooling apparatus 33 under the PI control to uniformize the article temperature, and after this a deep freezing for keeping a balanced temperature of −18±2° C. is performed under the PI control of the cooling device 34.

The PI, PID control of the heating source 32, cooling device 33, 34 are performed by way of a control valve 33b and a control valve 34b with corporation between the main controller 36 and the auxiliary controller 37. By the way, impacting jet streams may be used instead of the air blast from the blowing fan 35.

Figure 3:
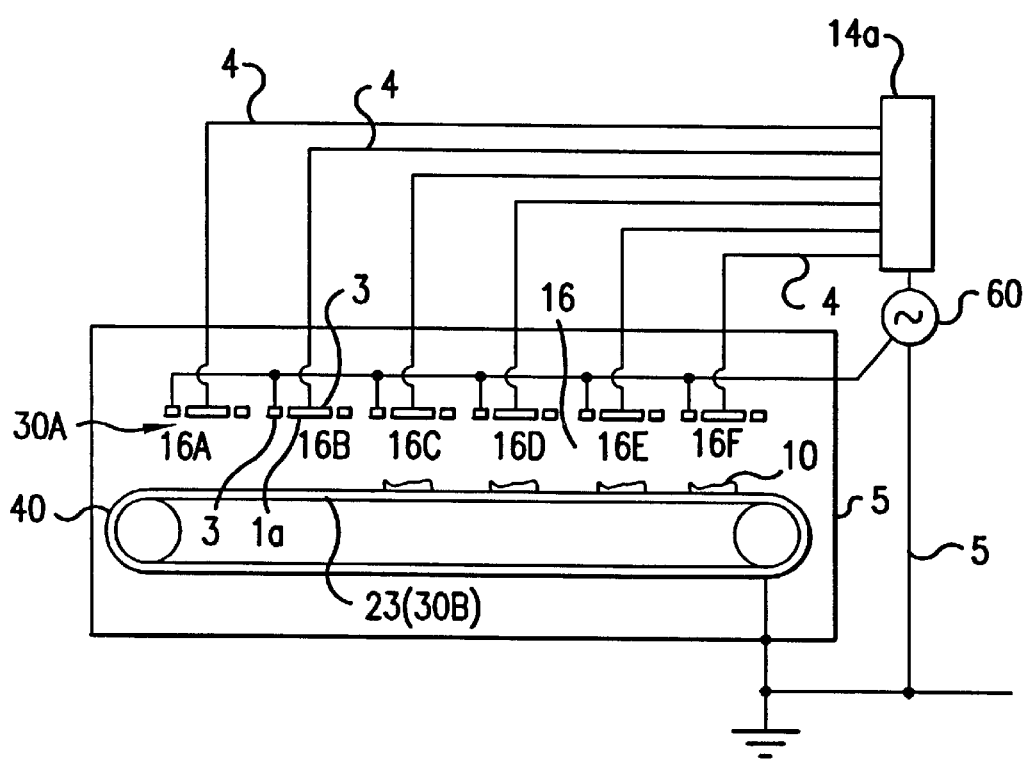
FIG. 3 is a schematic representation showing the configuration of a continuous freezing/unfreezing apparatus to which the basic construction of FIG. 1 is applied.

FIG. 3 is a schematic representation showing the configuration of a continuous freezing/unfreezing apparatus to which the construction of the capacitance detector of FIG. 1 is applied.

As shown in the drawing, the positive electrodes 1a, 1a, which are located in the upper space 16 of a conveyor 40 having electric conductivity with the same spacing to each other or located in group of several pieces at several parts necessary for measuring capacitance in freezing process and the guard electrodes 3, 3, each of which surrounds each of the positive electrodes 1a with appropriate spacing for prevention of the diffusion of lines of electric force, are sandwiched and sealed to constitute each positive sensor electrodes 30A. The noise filter 14 as shown in FIG. 1 is provided above each of the positive sensor electrodes 30A with spacing to each sensor electrode, although the noise filters are not shown in FIG. 3.

The other sensor electrode 30B is so composed that the common electrode 1b of electric conductive belt shape equipped to the conveyor 40 is covered with a substantial insulation plate 2 to constitute a negative electrode or grounded electrode. The electric conductive belt-form sensor electrode 30B and the positive sensor electrodes 30A constitute noncontact capacitance sensors 30.

The belt-form sensor electrode 30B of the conveyor 40 is grounded by way of the conveyor frame which is grounded. An earth terminal of the positive sensor electrode 30A is connected to the metal part of the frame of the conveyor which connects electrically to the electric conductive belt-form sensor electrode 30B. A plurality of the positive electrodes 1a, 1a are connected to the positive terminal of the capacitance measuring section 60 by way of a scanning device 14c which periodically makes or breaks the circuit in time sequence.

The guard electrodes 3 are provided around the positive electrodes 1a to prevent the diffusion of lines of electric force and grounded by way of a lead wire.

With the construction described above, the food articles 10 are placed on the running conveyor 40 as they are or with an insulation sheet laid between the food article 10 and the electric conductive belt-form sensor electrode 30B keeping the spacing distances corresponding to the plurality of the zone 16A~16F determined by the positive sensor electrodes 30A which are located in the upper space of the conductive belt-form sensor electrode 30B facing the same across the layer of gas such as air or refrigerant gas supplied into the apparatus, and a high frequency voltage scanned by the scanning device 14c is applied between each of the positive sensor electrodes 30A and the negative sensor electrode (electric conductive belt) to measure capacitance.

By the measurement like this the article temperature of food, completion of freezing, and the degree of freeze in the process of freezing are determined.

The noncontact sensor described above is able to measure capacitance in the case the gas layer in the space above the food is a gas other than air such as nitrogen, carbon dioxide, water vapor, or mixture of these gases.

Figure 5:
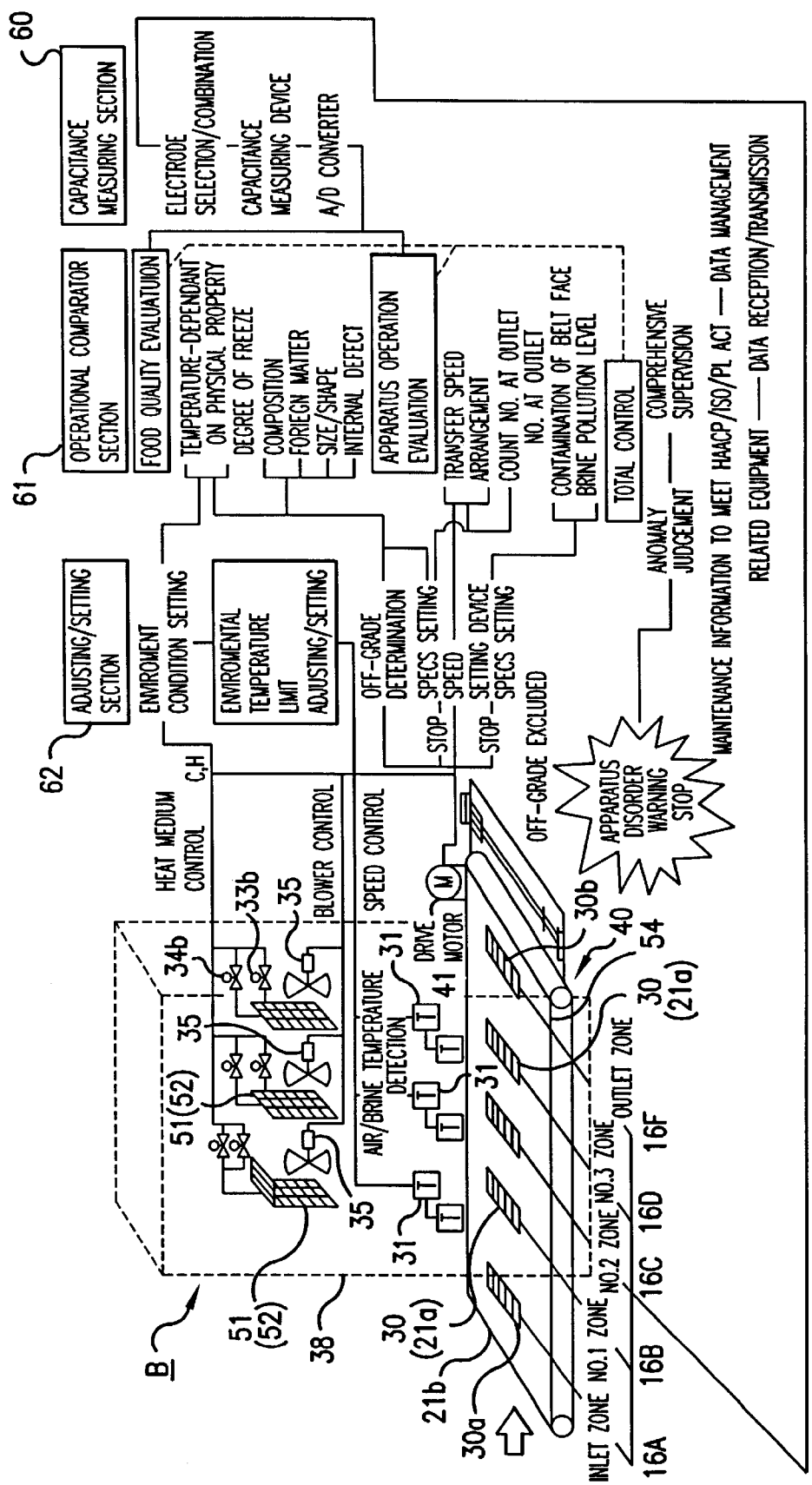
FIG. 5 is a schematic representation showing the configuration of the freezing/unfreezing system using the continuous freezing/unfreezing apparatus of FIG. 3.

FIG. 5 is a schematic representation showing a configuration of the freezing/unfreezing system in which the noncontact article temperature measuring device of FIG. 3 is applied to a continuous freezing/unfreezing apparatus B.

In the freezing/unfreezing room 38, several zones 16A~16F are formed and positive sensor electrodes 30a, 30a, are provided, each corresponding to its pertinent zone. Between the inlet zone 16A and the outlet zone 16F, three zones 16B~16C for unfreezing are provided.

Below the positive sensor electrodes 30a, 30a, is provided the conveyor 40 equipped with the belt-form sensor electrode 30B which is the grounded electrode. A drive motor 41 for driving the conveyor 40 is provided at the end side of the conveyor 40. Further, in the unfreezing zone 16B~16C are provided cooling means 51 and heating means 52 for cooling and heating by cooling heat medium and heating heat medium respectively, and temperature sensors 31, 31, for controlling the temperature of each zone.

Still further, fans 35 for blowing air are provided facing each cooling means 51, heating means 52 so as to enable the temperature control of each zone separately.

When the food enters each zone and the predetermined voltage is applied between each positive sensor electrode 30A and the belt-form sensor electrode 30B, the capacitance of each food article is possible to be measured.

The pair of the sensor electrodes 30A, 30B constituting the capacitance sensor 30 is connected to the capacitance measuring section 60 to constitute the noncontact article temperature measuring device.

The capacitance measuring section 60 comprises; a selector which selects a capacitance sensor 30 among the capacitance sensors 30 located in the zones 16A~16F for measuring; measurement device for determining the capacitance by the signal from the capacitance sensor 30; and an A/D converter.

The measured data is transferred from the capcitance measuring section 60 to the operational comparator section 61.

The operational comparater section 61 receives the measured capacitance data in the process of freezing in time series from the capacitance measuring section 60 and compares the data with the capacitance data of a specific food article in the process of freezing measured beforehand and memorized in the self-contained physical property change rate setting device, by which comparison the temperature, degree of freezing, intrusion of foreign matter are detected and the evaluation of the quality of the measured food article is performed along with the evaluation of operation such as transfer speed of the conveyor, contamination of the belt surface, pollution of the brine.

The evaluation data of quality and operation obtained from the operational comparator section 61 enables the control of temperature and operation by means of controlling flow rate of the cooling heat medium (C) and the heating heat medium (H), based on the environment temperature, the standard temperature set by the limit setter, and the result of computation in the operational comparator section 61. The food determined to be out of evaluation criteria is excluded by the excluding conveyor 43. In the case of disorder in operation, an alarm is raised and the operation is stopped.

To verify the effect of the present invention, the correlation between capacitance and temperature was investigated using the capacitance sensor 30 shown in FIG. 7.

A hamburger, a piece of shaped dough, and ethyl alcohol on the market was chosen as test pieces. Two capacitance sensors 30 shown in FIG. 7 adjacent to each other were placed in the multistage container made of plastics in the freezing/unfreezing room 38 of the batch type freezing/unfreezing apparatus A shown in FIG. 2. One of the sensors was used for measuring capacitance and the other used was not used for measuring but temperature of the test piece placed between the electrodes of the other sensor was measured directly with thermisters inserted into the test piece. The environment condition of the freezing/unfreezing room 38, that is, the temperature and air speed in the room 38 was kept constant.

(I) The Relation Between the Capacitance and Temperature in the Process of Cooling and Heating Ethyl Alcohol.

Figure 18:
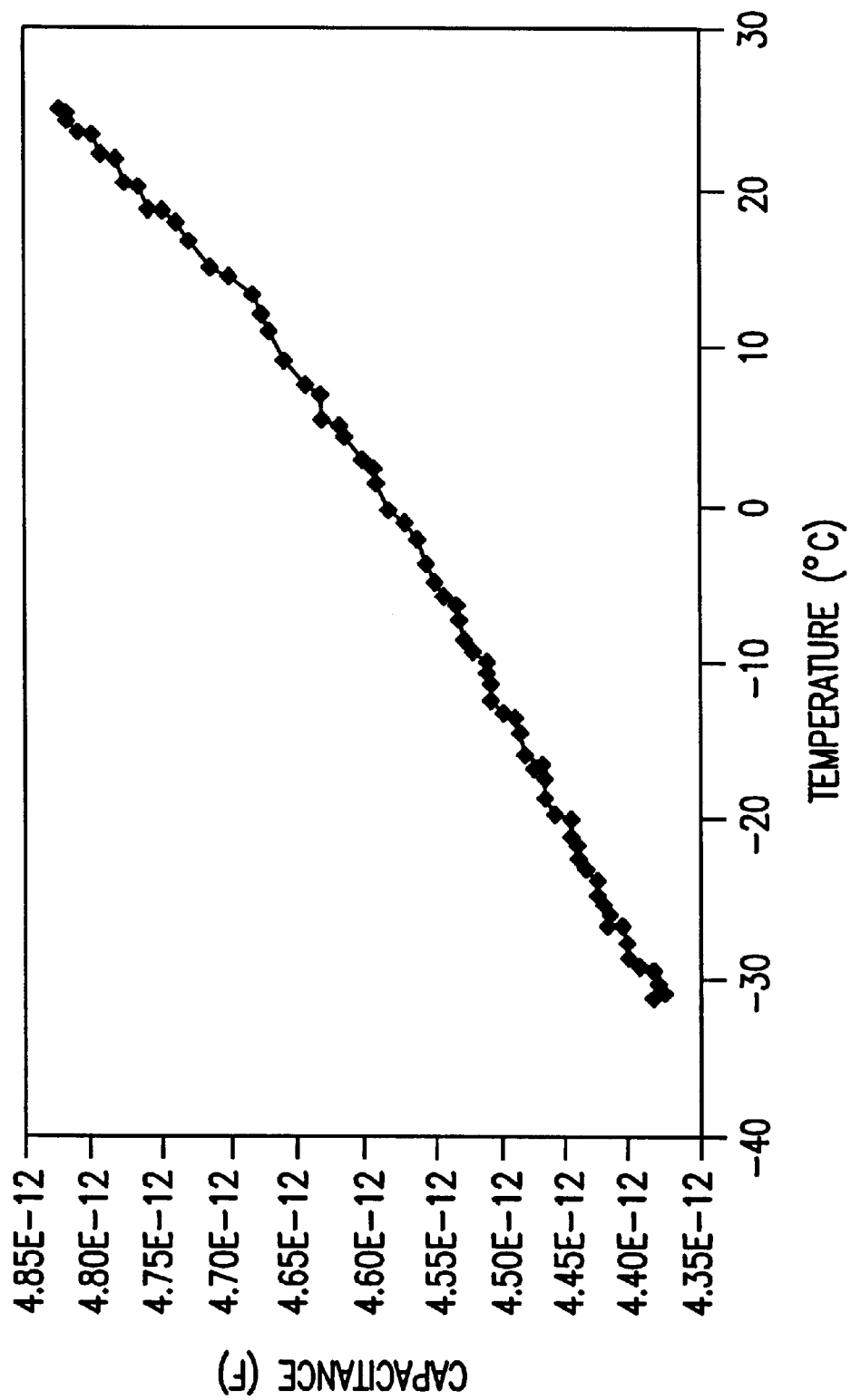
FIG. 18 is a graph showing the relation between the capacitance and temperature in cooling process in the case of ethyl alcohol.

FIG. 18 is a graph showing the relation between the capacitance and temperature in the cooling process of ethyl alcohol.

Measurement were carried out with the same sample in a cooling process from +25° C. to −32° C., in a heating process from −30° C. to +20° C., and in a re-cooling process from +20° C. to −30° C.

From FIG. 18, it is recognized that the relation between the capacity and temperature of ethyl alcohol in cooling process is nearly a straight line in the range from +25° C. to −32° C., that is, the relation can be expressed by a linear equation.

As to the heating process and re-cooling process, the relation was almost the same.

(II) The Relation Between the Capacitance and Temperature in the Process of Freezing and Unfreezing a Hamburger.

Using a hamburger on the market, which hamburger is manufactured by industrialized equipment and stable in quality, as a sample, the change of capacitance and temperature with the lapse of time was measured and the relations between the capacitance, temperature, and time were obtained.

Measurement was carried out five times with five samples.

FIG. 19~FIG. 28 are graphs showing one of the result obtained with one of the samples. As to temperature, eight temperature sensors are inserted into a hamburger at different points to the same depth. FIG. 19, FIG. 20, FIG. 23, FIG. 24, and FIG. 25 show the result of measurement in the freezing process.

Figure 19:
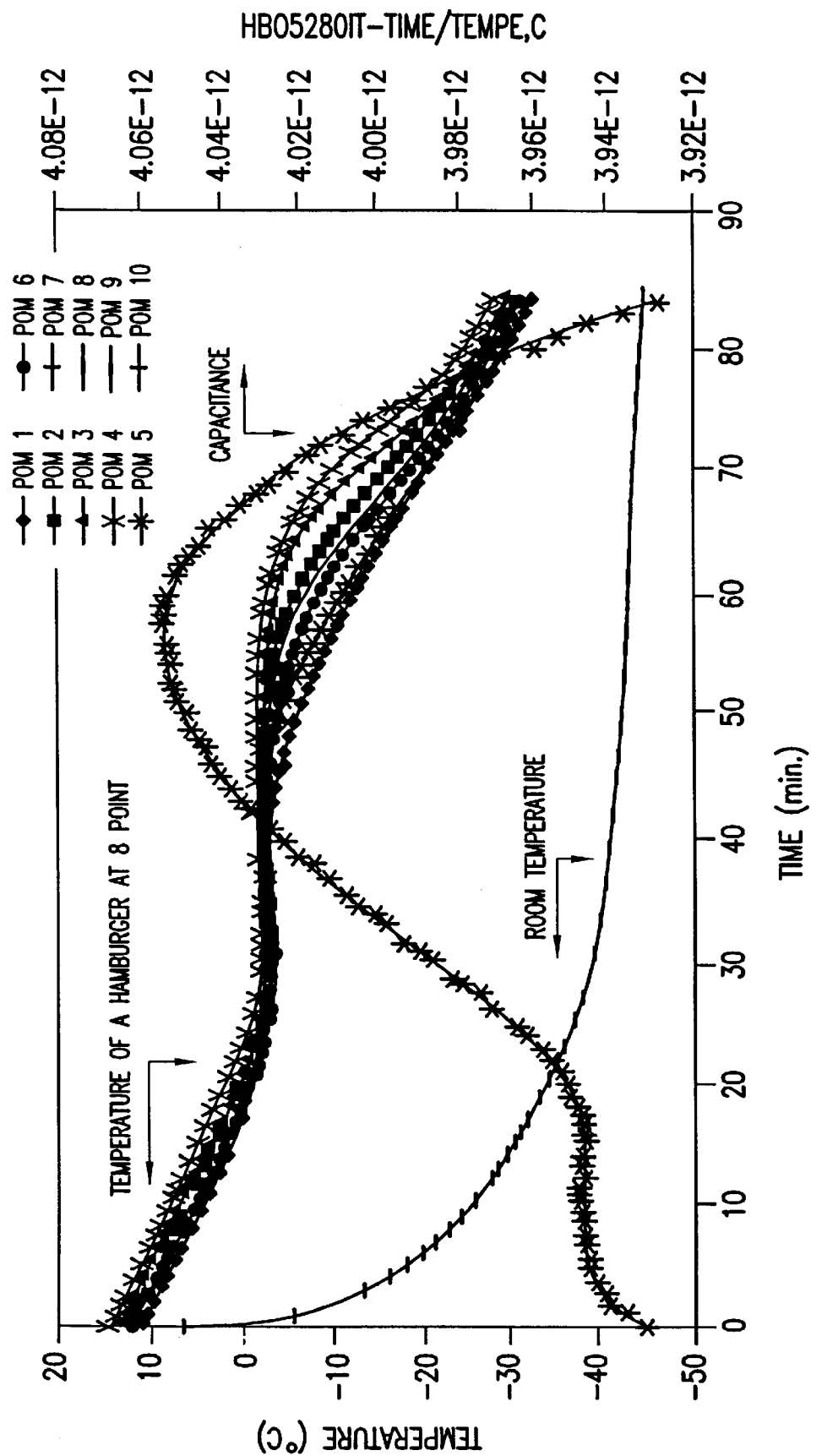
FIG. 19 is a graph showing the change of temperature and capacitance of a hamburger with the lapse of time when the same is frozen.
Figure 20:
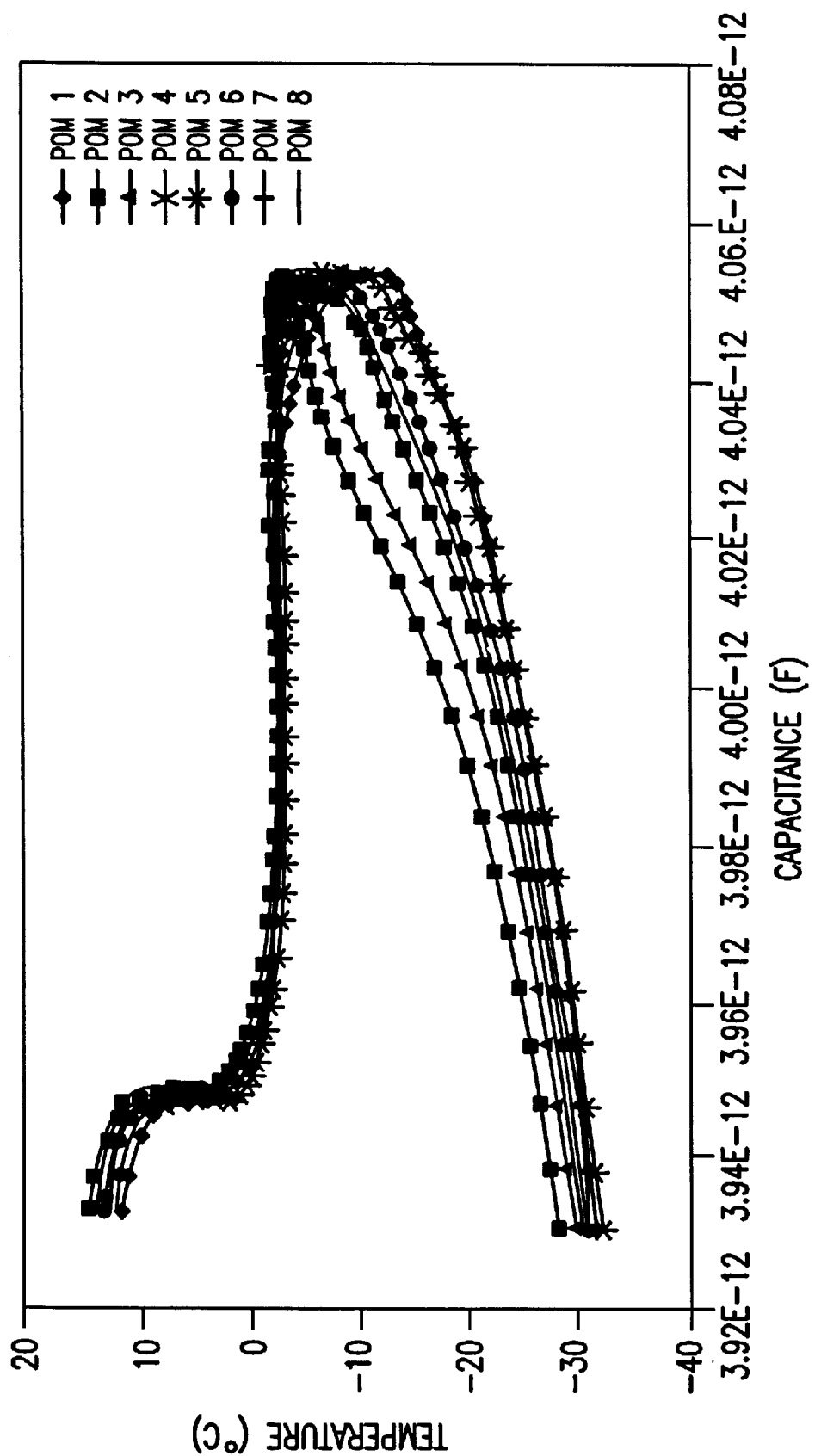
FIG. 20 is a graph showing the relation between the temperature and capacitance when a hamburger is frozen, which relation shows the change of state of freezing (frozen state).

FIG. 19 shows variations of capacitance and temperatures with the lapse of time, FIG. 20 the relation between the temperatures of the sample and the capacitance, FIG. 23 and FIG. 24 the relation between the temperature and the second derivative of the capacitance with respect to time, FIG. 25 the relation between the time and the derivative of the capacitance with respect to time.

Hereinafter, the measured values of temperature and capacitance are referred to as POM which means point of measurement. POM1~POM8 are the temperatures of the samples, POM9 is the room temperature, and POM10 is the capacitance. No. in the graphs indicates the sensor No. which measured the capacitance. The numbering is the same for other embodiments.

From FIG. 19 and FIG. 20, it is evident that the slope of the capacitance line becomes steep when a part of the hamburger reaches freezing point, and when the whole hamburger reaches freezing point the capacitance is maximum. After the freezing, the capacitance decreases with decreasing freeze temperature of the hamburger. The maximum ice-crystal formative zone for the hamburger is passed during the period between the start and completion of freezing and the ratio between frozen part and the part still not frozen can be estimated. So frozen/thawed state is estimated along with temperature.

The slight decrease in capacitance near the temperature of +10° C. is supposed to be caused by the hardening of fat, which coincides with the measurement result by DSC, Differential Scanning Calorimeter. Therefore quality evaluation of food is also possible.

FIG. 23 and FIG. 24 are graphs showing the values of the second derivative of capacitance with respect to time versus temperature in the freezing process of the hamburger measured with the sensor No.1~4, and No.5~8 respectively. The value of second derivative of capacitance changes in nearly perpendicular to the temperature when the hamburger reaches freezing point. From this, the freezing point of the hamburger is easily estimated to be $-2.7\pm0.2°$ C. The freezing point is clearly recognized by the comparative investigation of FIG. 20, FIG. 23, and FIG. 24.

FIG. 25 shows the value of the derivative of capacitance with respect to time versus time when a hamburger is frozen. The value of the abscissa when the curve of derivative dc/dt crosses the abscissa from under and from over the abscissa are the times when the capacitance is minimum and maximum respectively in FIG. 19, which show the time when the freezing started and completed respectively.

Figure 21:
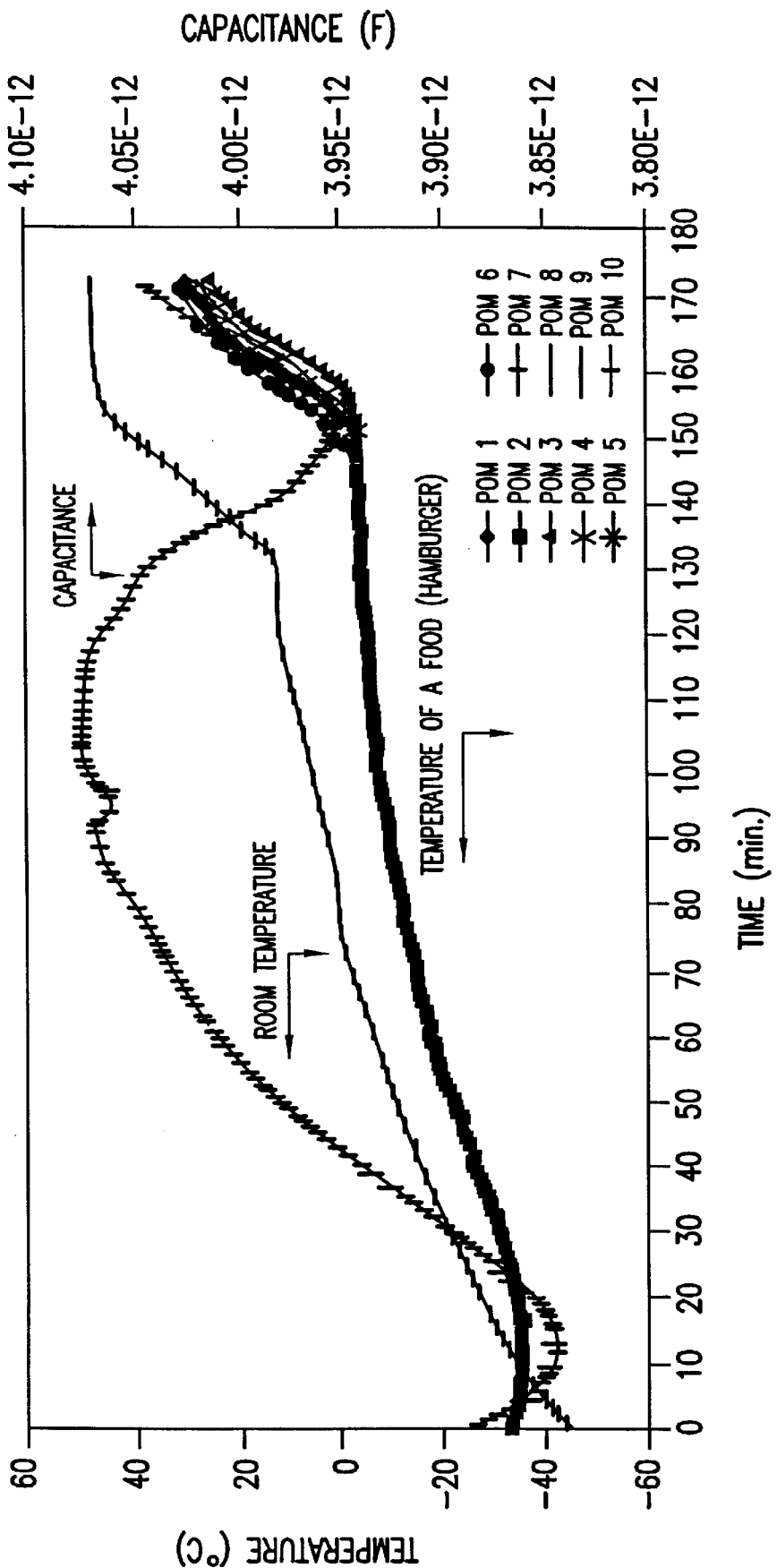
FIG. 21 is a graph showing the change of temperature and capacitance of a hamburger with the lapse of time when the same is unfrozen.

FIG. 21, FIG. 22, FIG. 26, FIG. 27, and FIG. 28 show the result of measurement in unfreezing process. FIG. 21 shows variations of capacitance and temperatures with the lapse of time, FIG. 22 the relation between the temperatures of the sample and the capacitance, FIG. 26 and FIG. 27 the relation between the temperature and the second derivative of the capacitance with respect to time, FIG. 28 the relation between the time and the derivative of the capacitance with respect to time.

Figure 22:
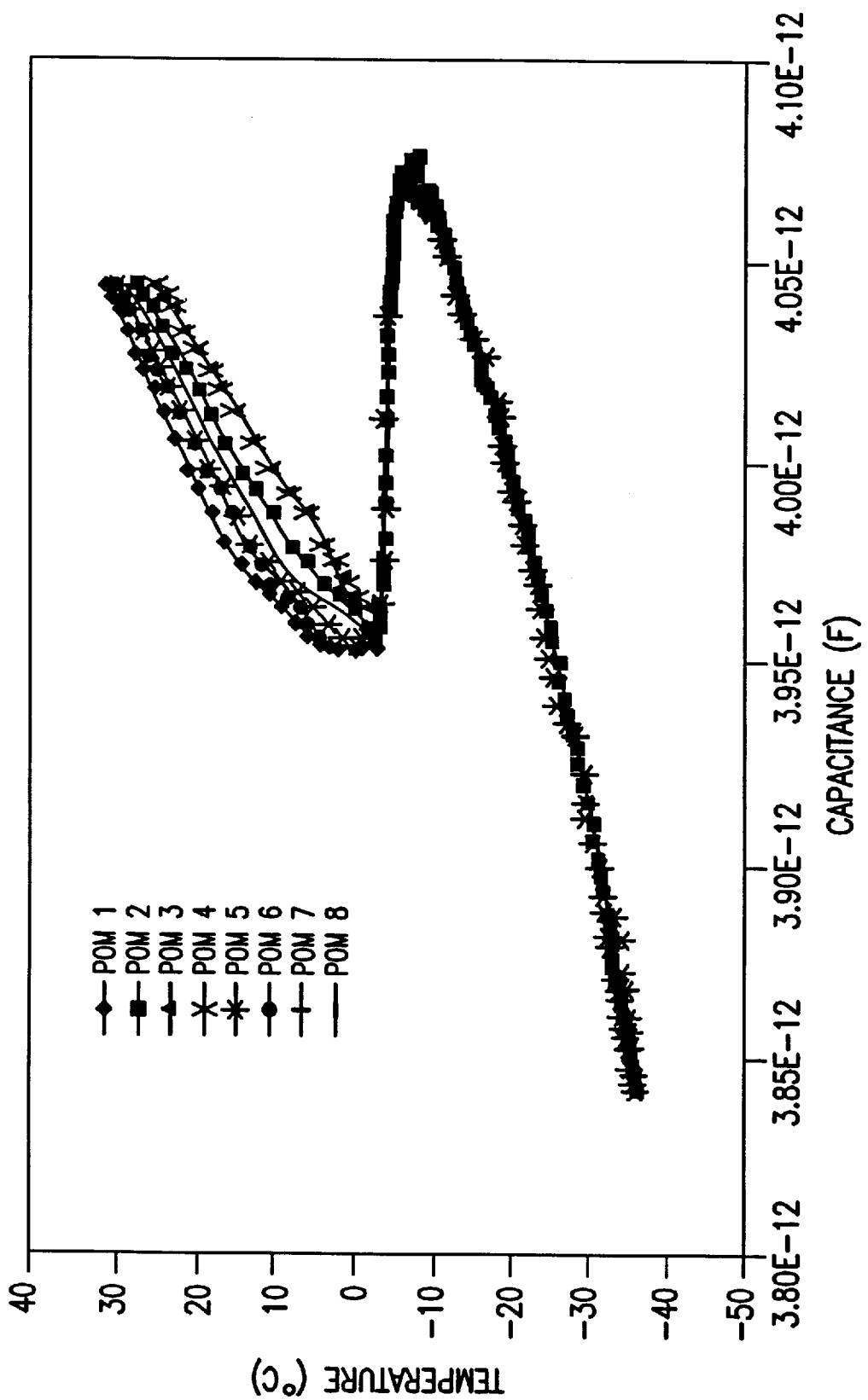
FIG. 22 is a graph showing the relation between the temperature and capacitance when a hamburger is unfrozen, which relation shows the change of state of unfreezing (thawed state).
Figure 23A:
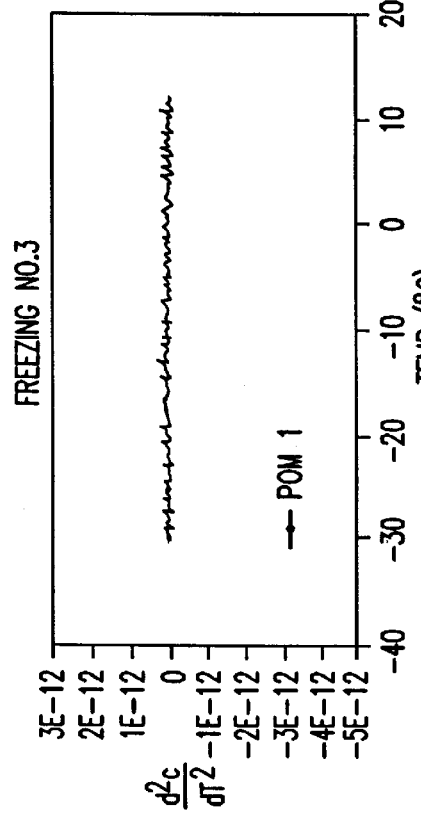
FIG. 23 are graphs showing the second derivative of capacitance with respect to time versus temperature measured with sensors of No.1~No.4 when a hamburger is frozen.
Figure 23C:
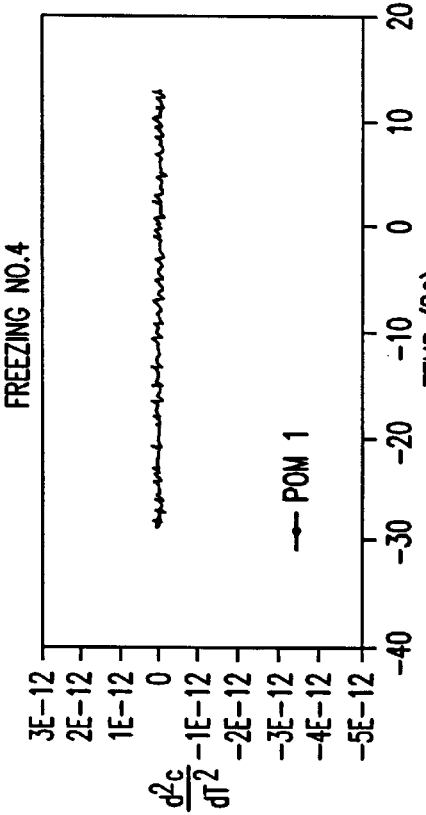
Figure 23B:
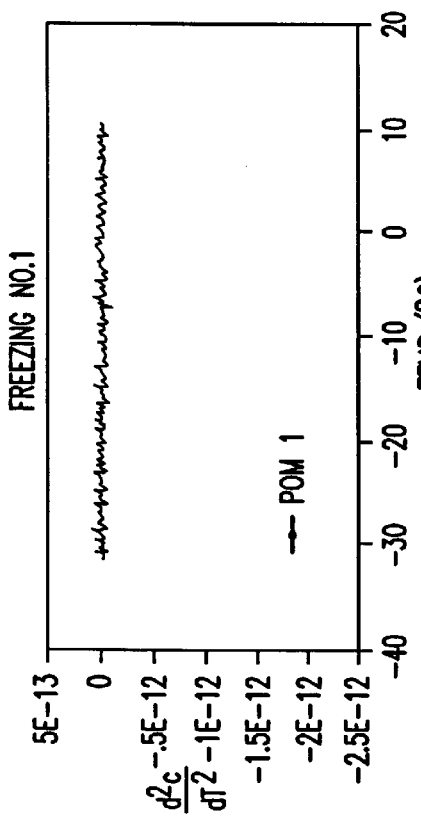
Figure 23D:
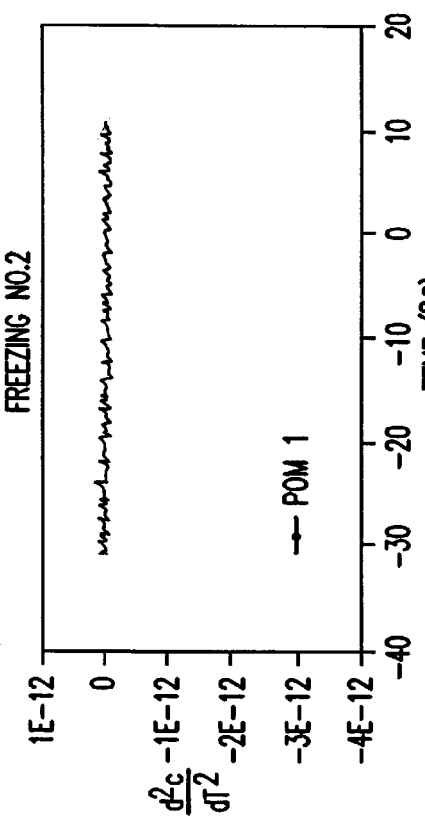
Figure 24C:
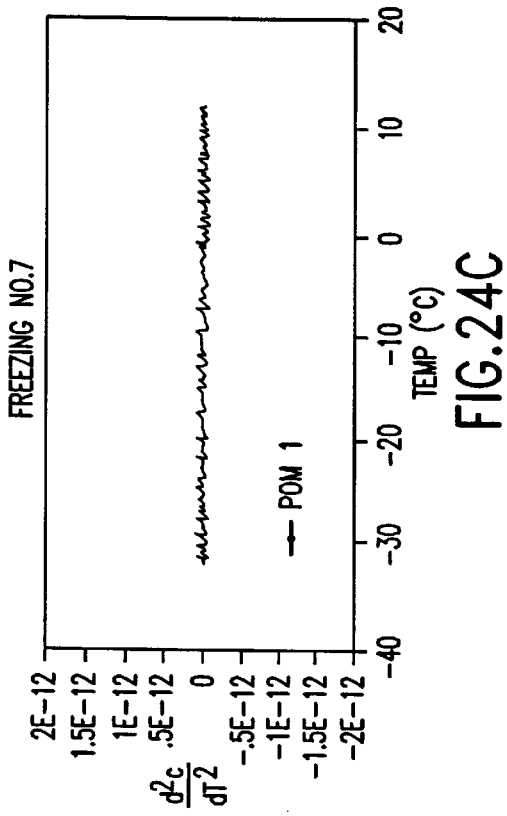
FIG. 24 are graphs showing the second derivative of capacitance with respect to time versus temperature measured with sensors of No.5~No.8 when a hamburger is frozen.
Figure 24D:
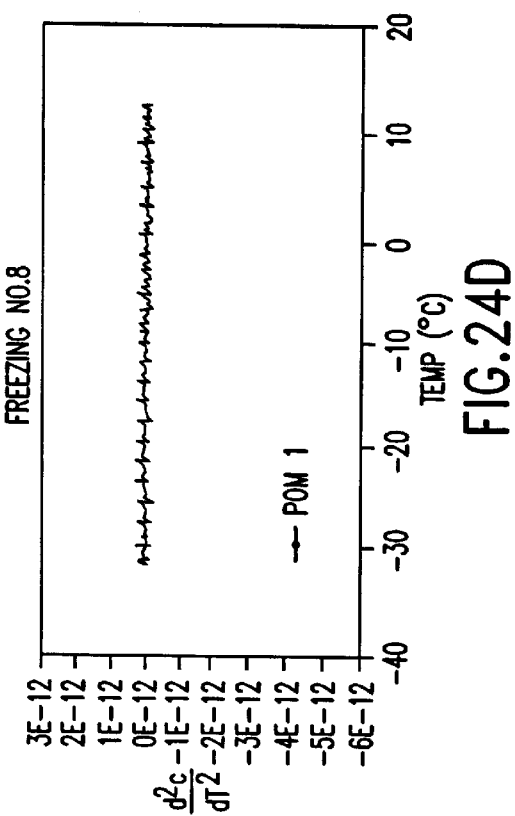
Figure 24A:
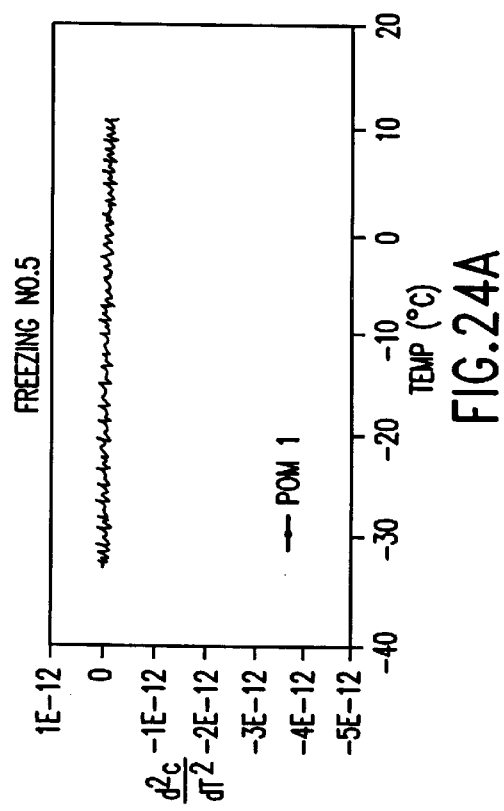
Figure 24B:
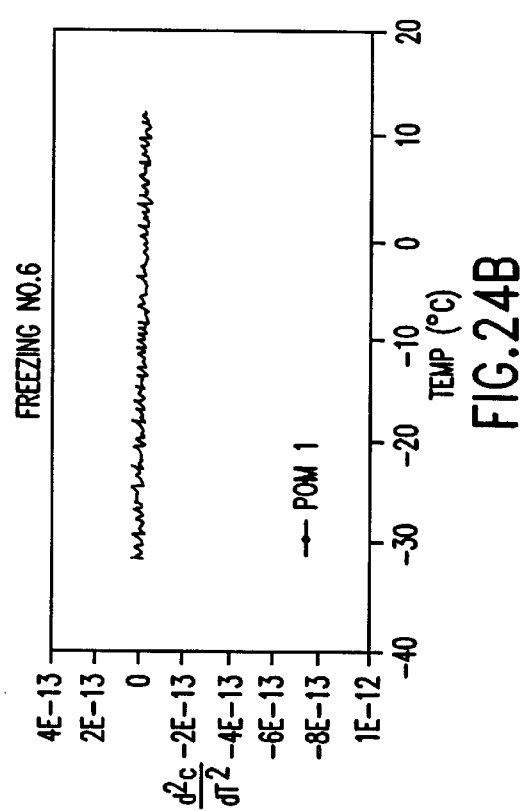
Figure 26A:
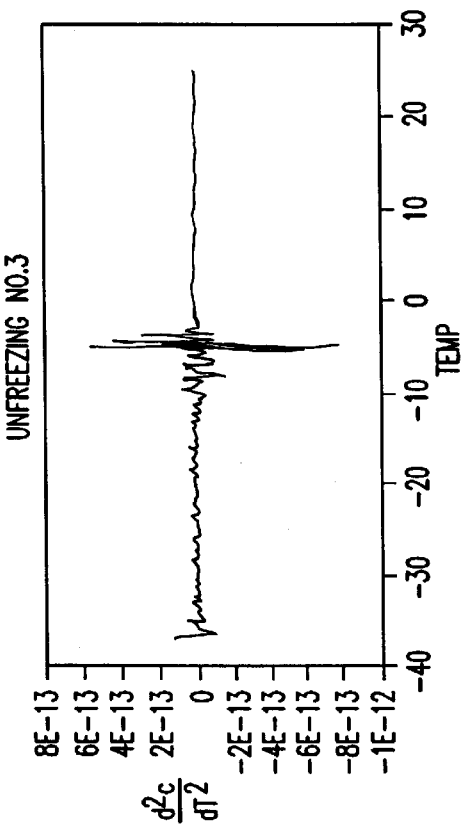
FIG. 26 are graphs showing the second derivative of capacitance with respect to time versus temperature measured with sensors of No.1~No.4 when a hamburger is unfrozen.
Figure 26C:
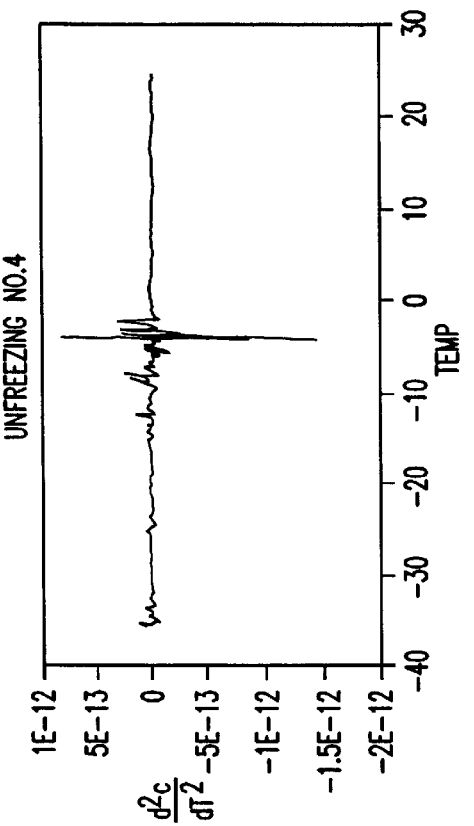
Figure 26B:
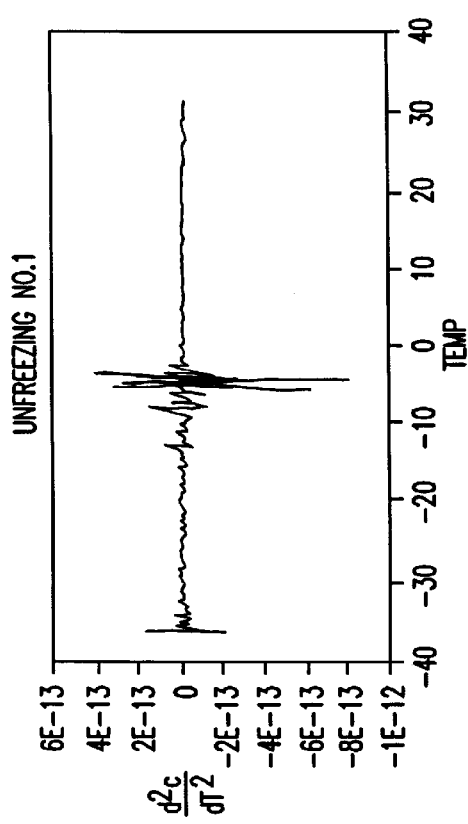
Figure 26D:
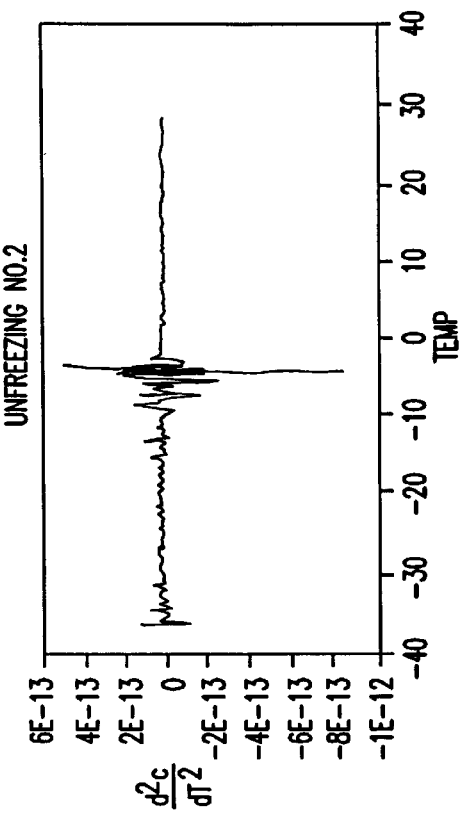
Figure 27A:
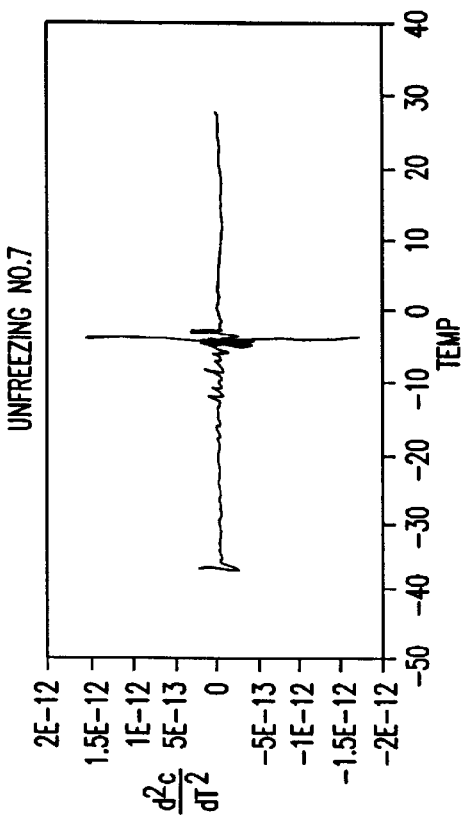
FIG. 27 are graphs showing the second derivative of capacitance with respect to time versus temperature measured with sensors of No.5~No.8 when a hamburger is unfrozen.
Figure 27B:
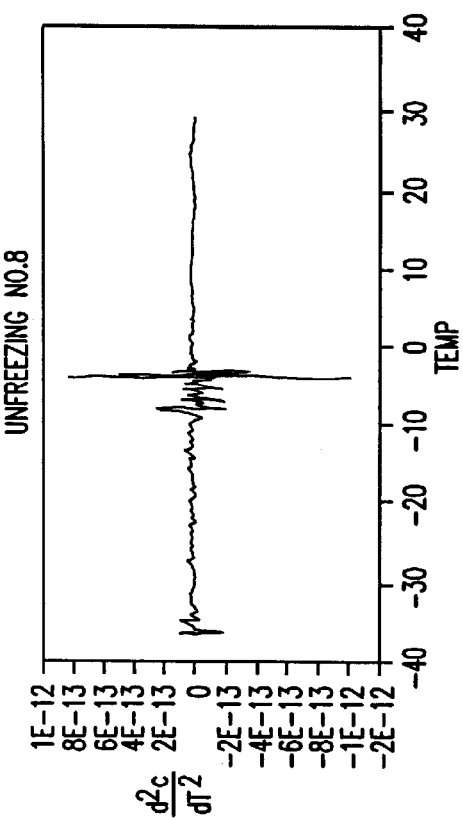
Figure 27C:
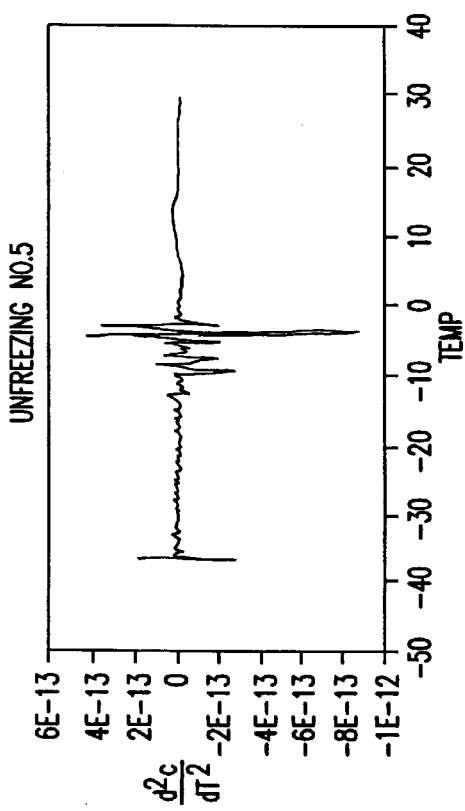
Figure 27D:
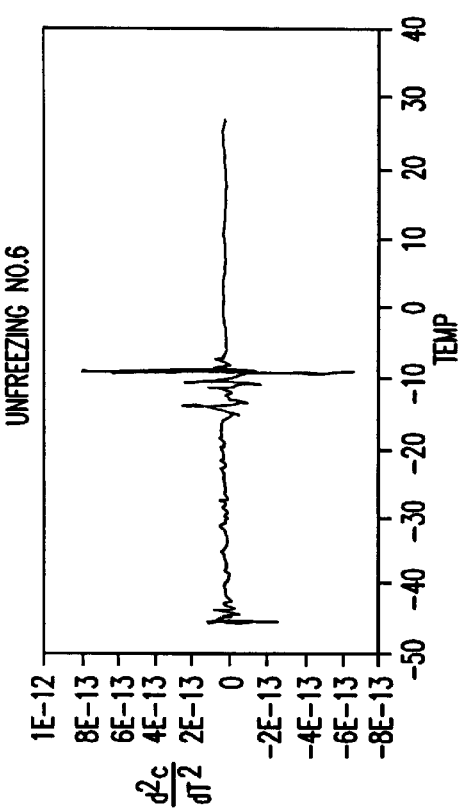

In FIG. 21 and FIG. 22, the capacitance curve becomes maximum when a part of the hamburger reaches the melting point, minimum when the whole part thawed, and after this the capacitance again increases with increasing temperature of the hamburger. The maximum ice-crystal formative zone for the hamburger is passed during the period between the maximum and minimum of the capacitance curve as is the case of freezing, and the ratio between thawed part and part remained still not-thawed part can be estimated. So frozen/thawed state is estimated along with temperature.

In FIG. 26 and FIG. 27, the second derivative of the capacitance varies nearly perpendicular to the abscissa at several points. In the case of unfreezing, differing from the case of freezing, the substance having lower freezing temperature starts thawing earlier.

When food is unfrozen, as water solutions of substances such as salts, carbohydrate, amino acid, fatty acid, etc. have various eutectic point, freezing occurs in the order of rising point of freezing and at the end the substance having higher water content thaws. For this reason, in FIG. 26 and FIG. 27, the second derivative of capacitance varies nearly perpendicular to the temperature axis at more than one point. Large variations occur near the temperature of $-10°$ C. and $-4.1\pm0.2°$ C. Through consideration of FIG. 21 together with FIG. 22, it is supposed that an ingredient of lower melting point thawed at $-10°$ C. and that of higher water content thawed at $-4.1\pm0.2°$ C.

As described above, freezing temperature in freezing process and thawing temperature in unfreezing process are different. This is supposed to be caused by the change in composition of the water solution contained in the hamburger owing to destruction of the cell membrane of the tissue of the hamburger due to freezing. The fact is supposed to have cause-and-effect relation to the experienced phenomenon that hamburger is softened at a temperature lower than the freezing point in unfreezing process and after unfreezing water solution separates from the hamburger.

Figure 28:
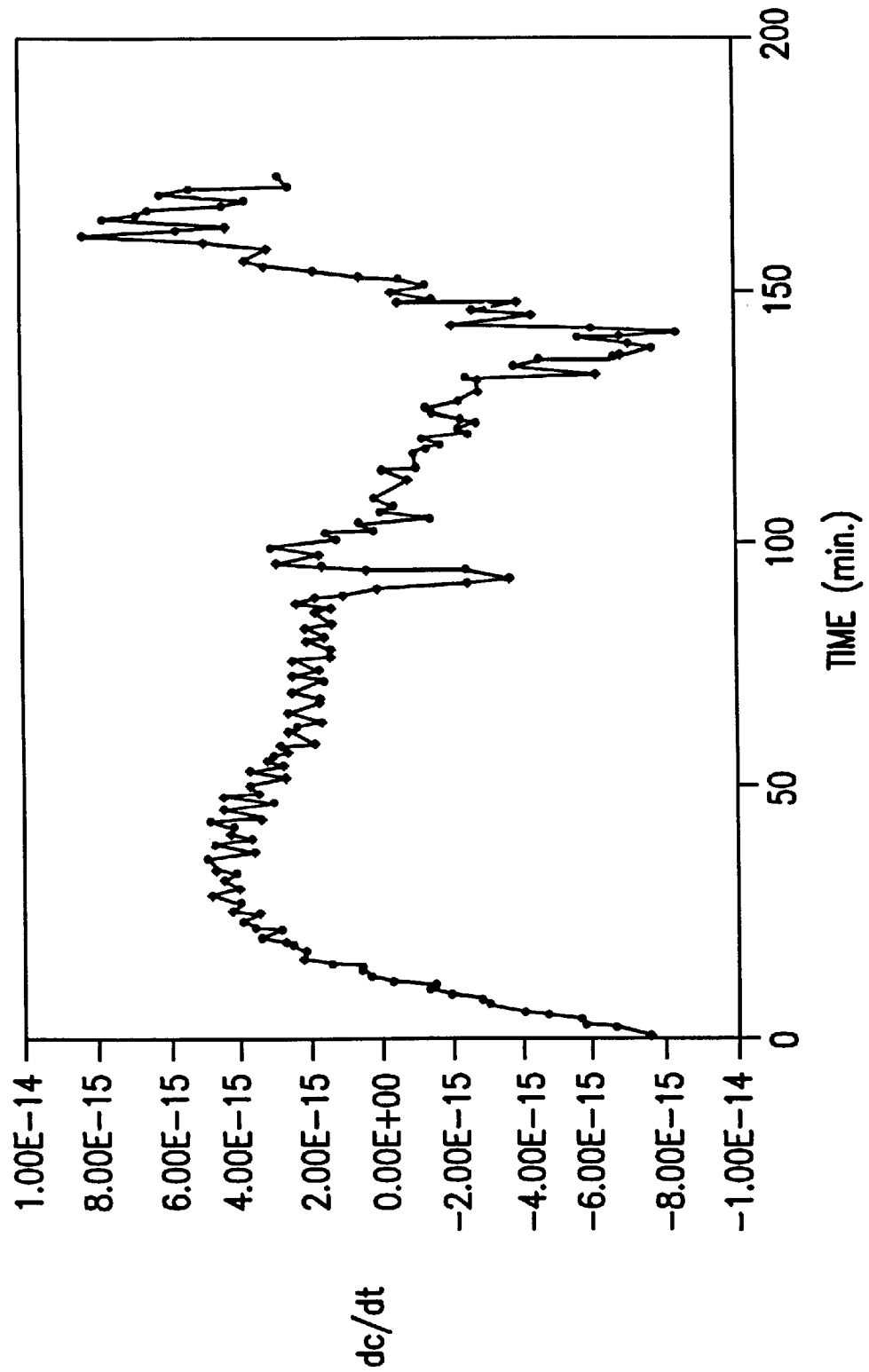
FIG. 28 is a graph showing the derivative of capacitance with respect to time versus time when a hamburger is unfrozen.

FIG. 28 shows the value of the derivative of the capacitance with respect to time versus time when a hamburger is unfrozen. The value of the abscissa when the curve of derivative dc/dt crosses the abscissa from over and from under the abscissa are the times when the capacitance is minimum and maximum respectively in FIG. 21, which show the time when the thawing started and completed respectively. Differing from the case of freezing, as described above, several eutectic point appears in accordance with the composition of the water solution contained.

Thus, the presence of the correlation between the capacitance and temperature was recognized also in the case of a hamburger.

Particularly, conspicuous change in capacitance appears at freezing point, melting point, melting completion point, from which frozen/thawed state of the food is detected.

Accordingly, by measuring the capacitance, the quality control of the measured article and the control of the apparatus can be improved.

(III) The Relation Between the Capacitance and Temperature in the Process of Freezing and Unfreezing a Piece of Dough for Bread.

As a combination food of two food material a cheese block enveloped with a piece of dough for bread was chosen as a sample.

FIG. 29~FIG. 36 are graphs showing the variation of the capacitance and temperature with the lapse of time, the relation between the temperature and capacitance, the relation between the temperature and second derivative of the capacitance with respect to time, and the relation between time and the derivative of the capacitance with respect to time in freezing and unfreezing process.

Figure 29:
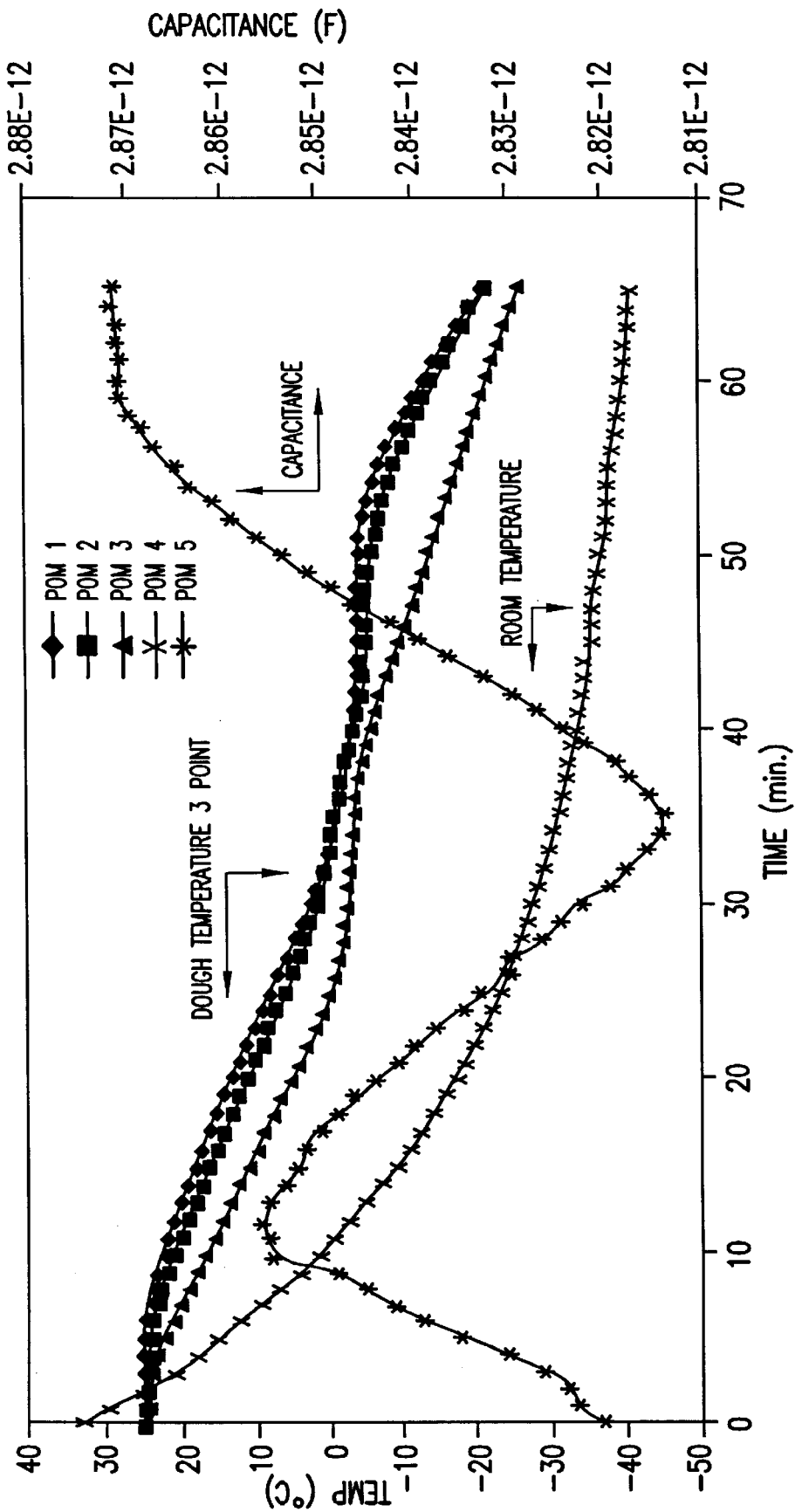
FIG. 29 is a graph showing the change of temperature and capacitance of a piece of dough with the lapse of time when the same is frozen.
Figure 30:
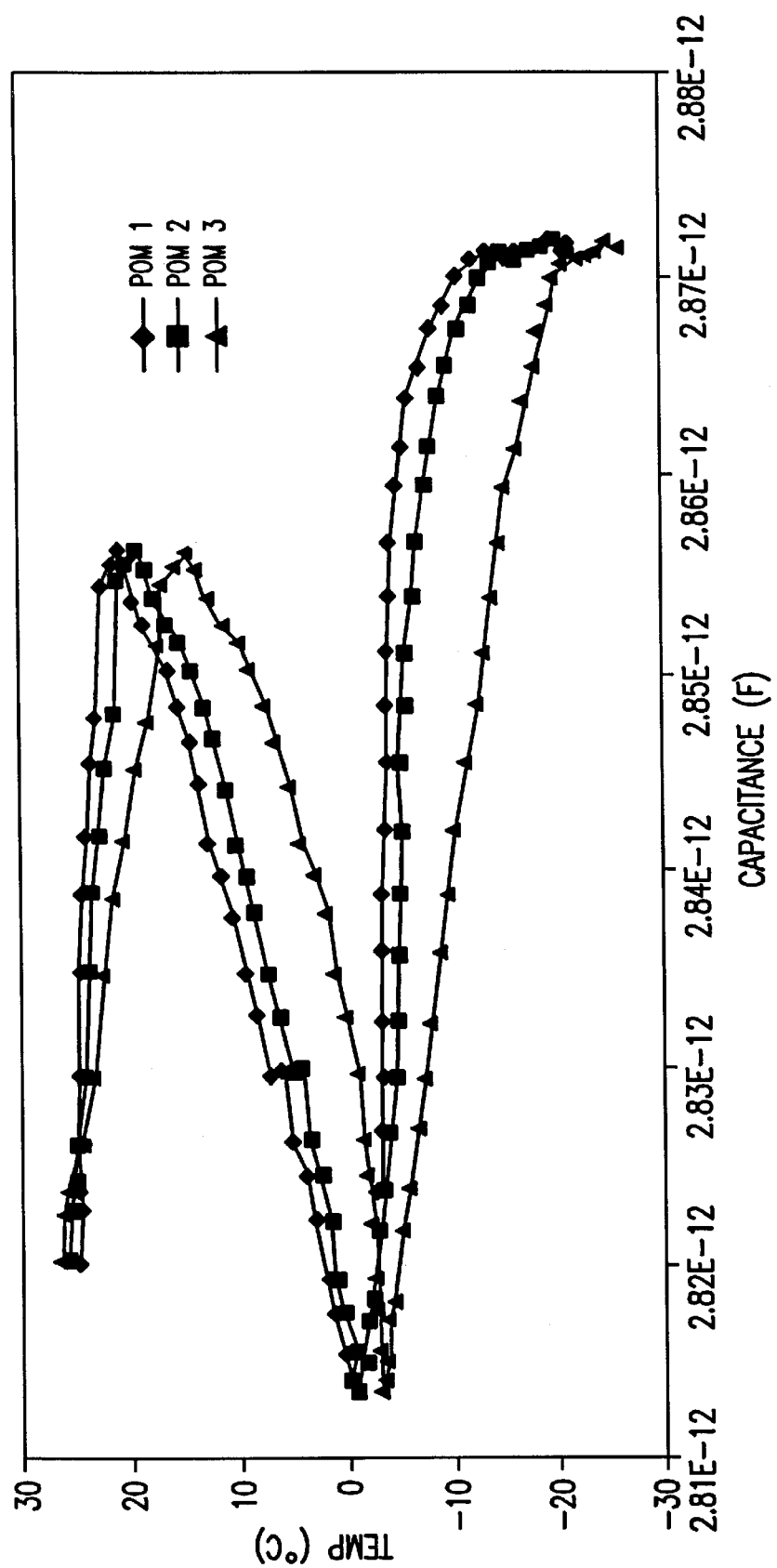
FIG. 30 is a graph showing relation between the temperature and capacitance when a piece of dough is frozen, which relation shows the change of state of freezing (frozen state).
Figure 31A:
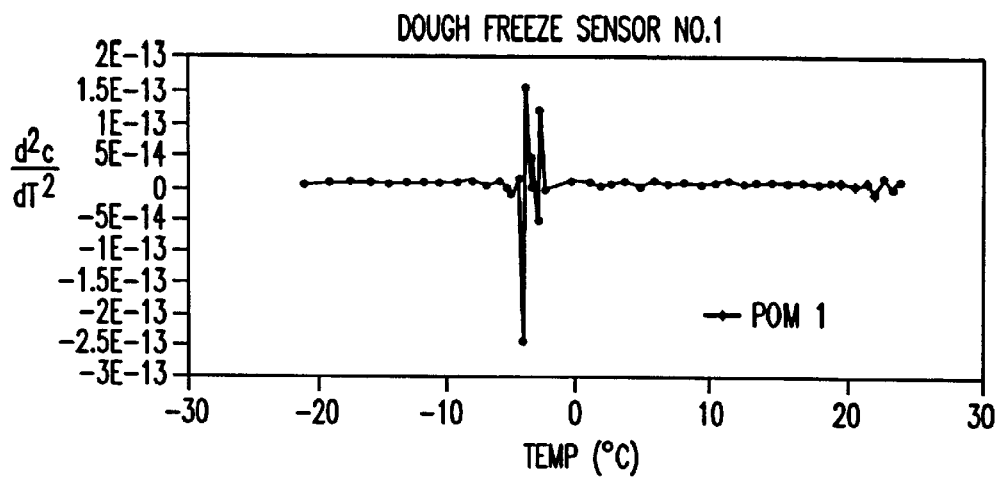
FIG. 31 are graphs showing the second derivatives of capacitance with respect to time versus temperature measured with sensors of No.1~No.3 when a piece of dough is frozen.
Figure 31B:
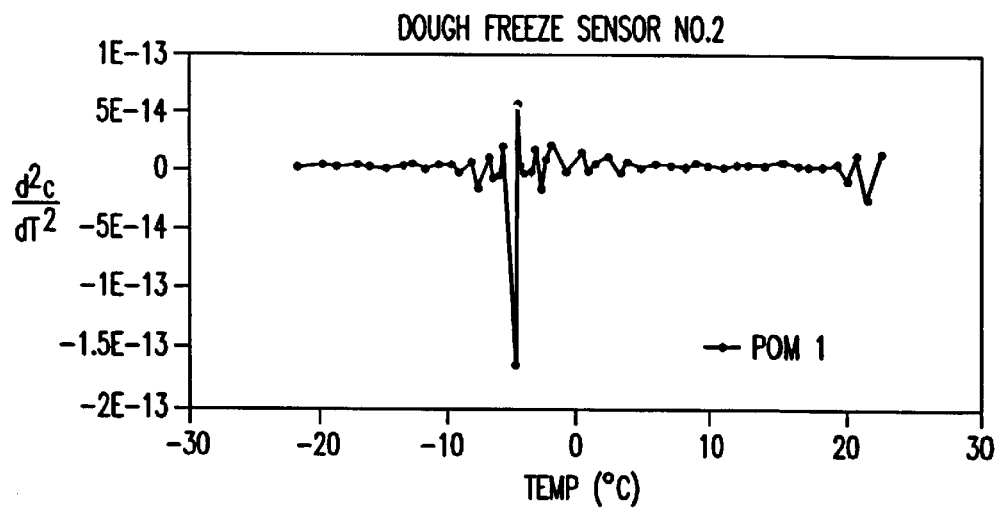
Figure 31C:
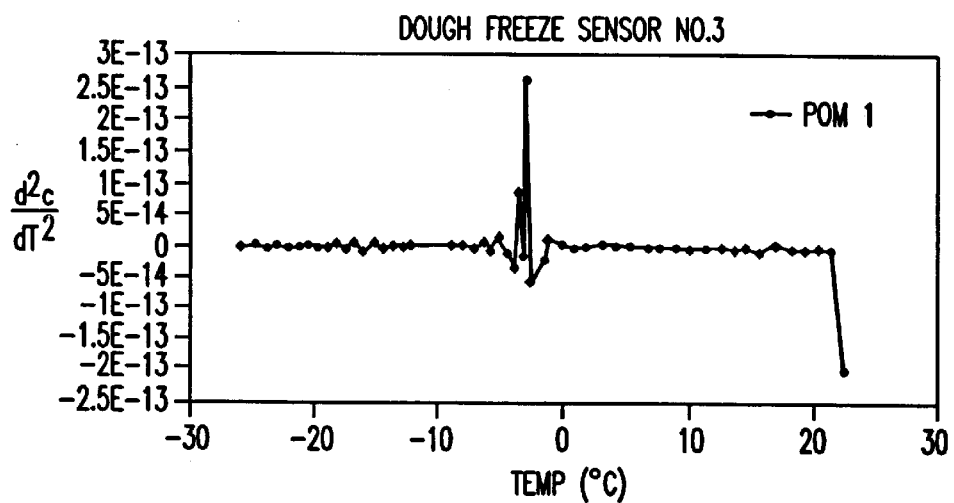

As seen in FIG. 29 and FIG. 30 showing the relations between the time, capacitance, and temperature, these relations in the freezing process are similar to the case on a hamburger during the start and completion of freezing. In the cooling process before freezing and in the temperature decreasing process after the completion of freezing, the relations show a different pattern.

In FIG. 29 and FIG. 30 the capacitance is minimum at freezing start point and maximum at freezing completion point.

Between the minimum and maximum, the ratio of freeze of the piece of dough varies. The freezing point of the piece of dough is estimated to be $-4.3\pm0.2°$ C. from FIG. 29, FIG. 30, and FIG. 31.

The freezing point and thawing point of the piece of dough and cheese enveloped with the same are different from each other, but in the case of an integrated food article like this, the freezing point and thawing point are grasped and evaluated as a total.

It is practical to be able to evaluate a combined food article as a total by capacitance measuring because practically no dough and cheese are separately frozen in food factories.

In the embodiment of the present invention, the plastics for protecting electrode, air between the sensor electrodes, and wrapper of food article influence the capacitance measurement.

When these mediums other than food exist, the measurement value of capacitance is a resultant capacitance of the food article and these mediums. The permittivity of air is assumed as that of vacuum. The capacitance due to mediums is assumed as fixed bias. The capacitance measurement varies in accordance with the dimension of electrodes, distance between the electrodes of a paired electrodes, and several other conditions, but they are treated as measuring device constant.

So the capacitance measurement to be used for controlling the quality of food article and operation of the freezing apparatus is treated as the capacitance of the food article (the capacitance measurement value is referred to as capacitance of the food article).

Figure 32:
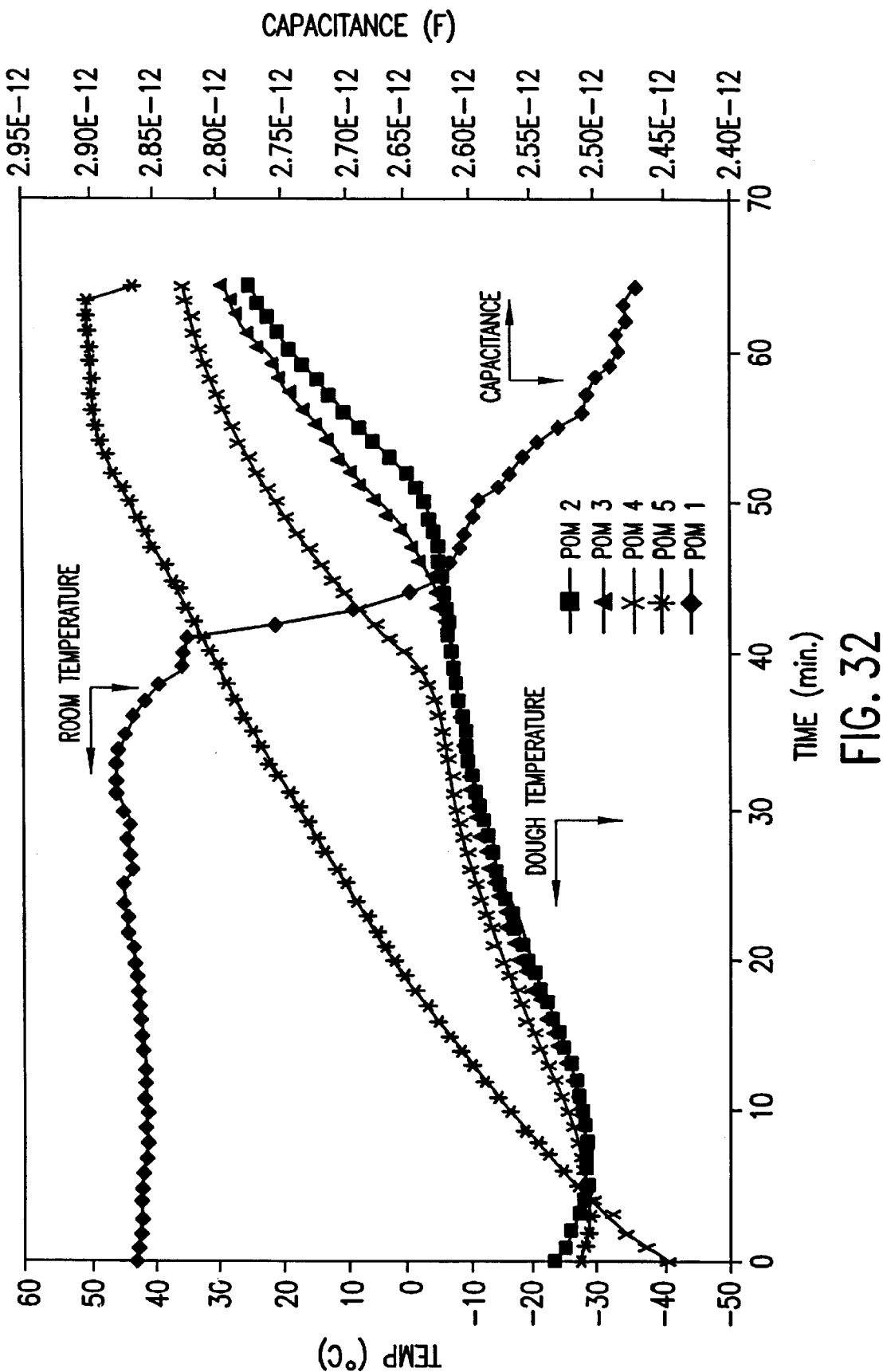
FIG. 32 is a graph showing the change of temperature and capacitance with the lapse of time when a piece of dough is unfrozen.
Figure 33:
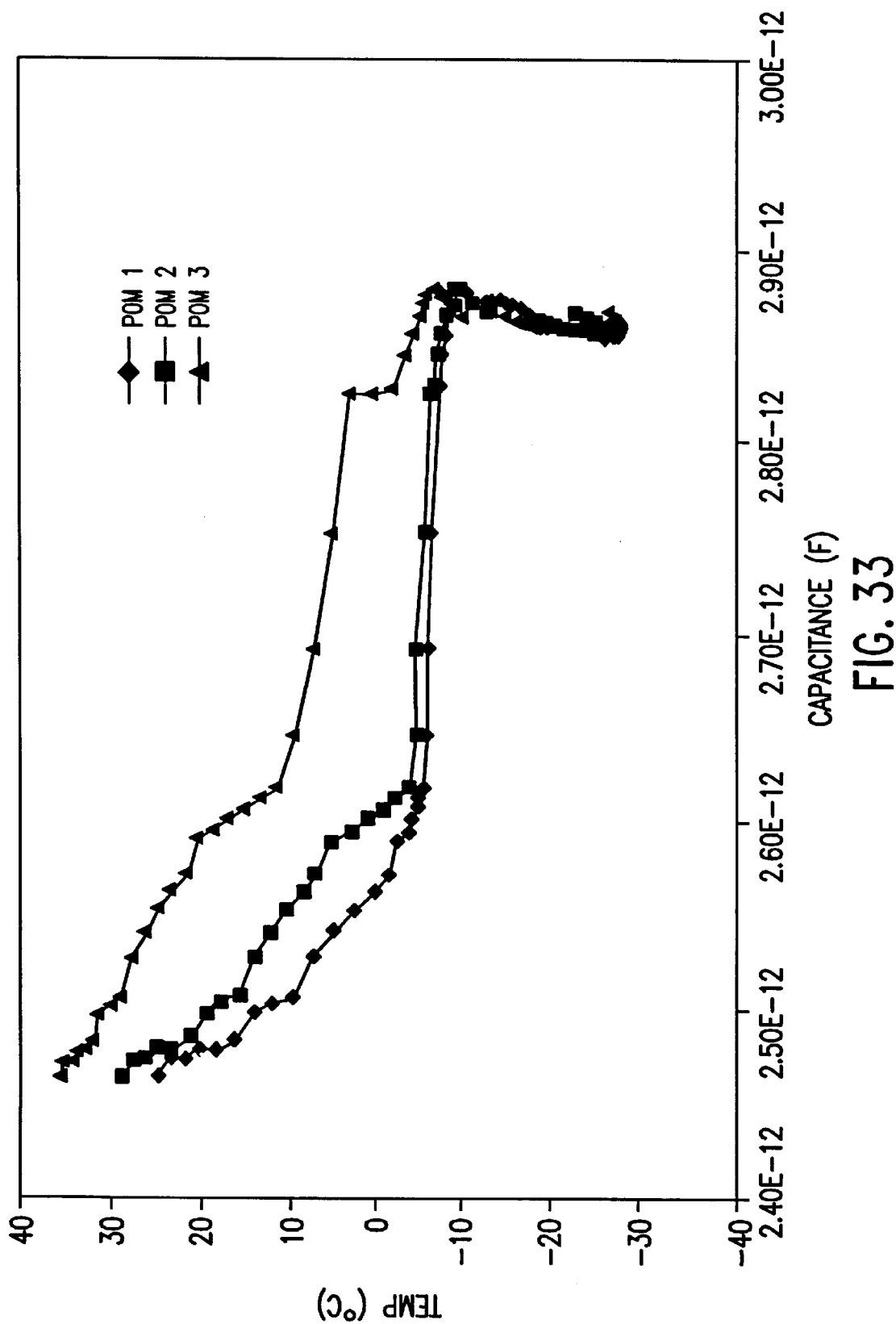
FIG. 33 is a graph showing the relation between the temperature and capacitance when a piece of dough is unfrozen, which relation shows the change of state of unfreezing (thawed state).
Figure 34A:
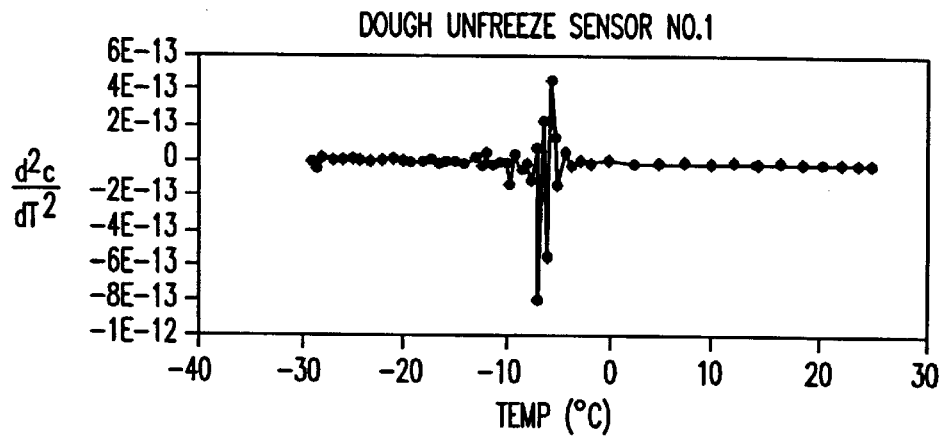
FIG. 34 are graphs showing the second derivatives of electrostatic capacity with respect to time versus temperature measured with sensors of No.1~No.3 when a piece of dough is unfrozen.
Figure 34B:
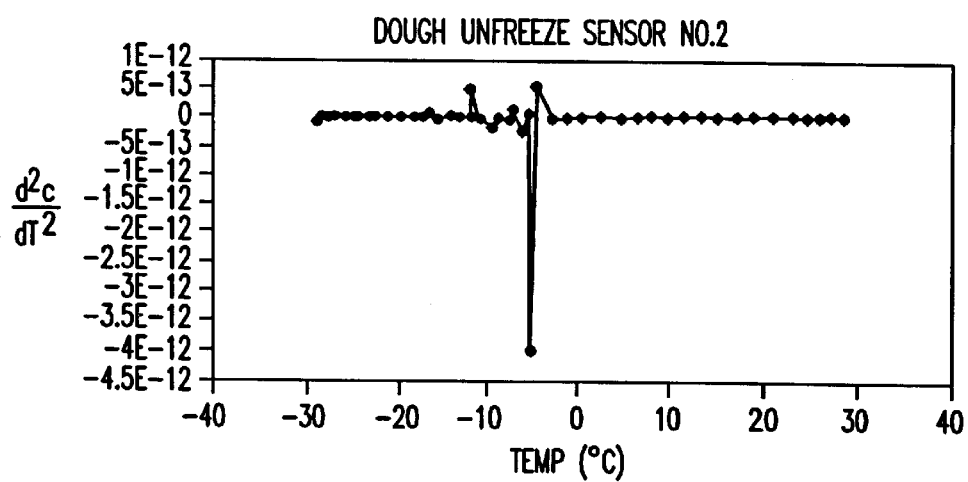
Figure 34C:
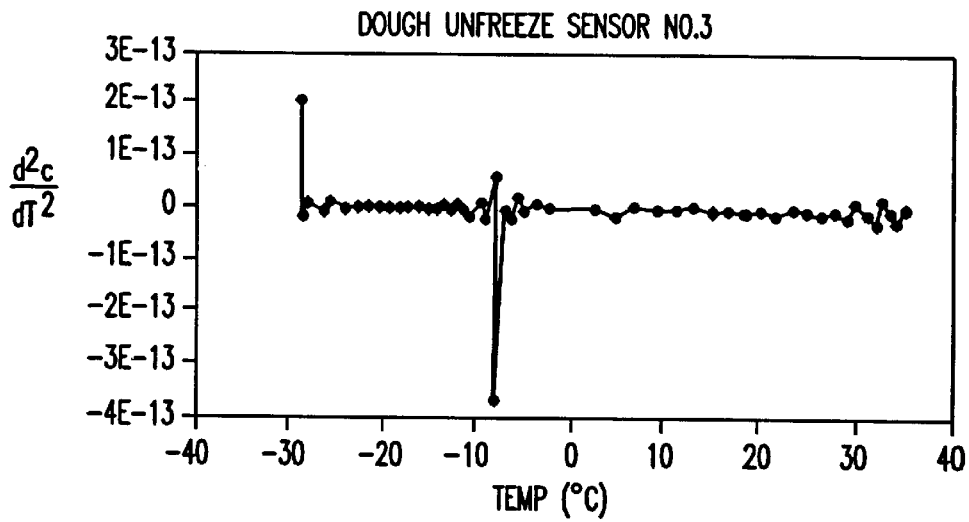

As to unfreezing, the melting point is estimated to be −5.4±0.2° C. from FIG. 32, FIG. 33, and FIG. 34, and the rate of melt of the piece of dough including cheese varies between the start and completion of thawing.

Figure 35:
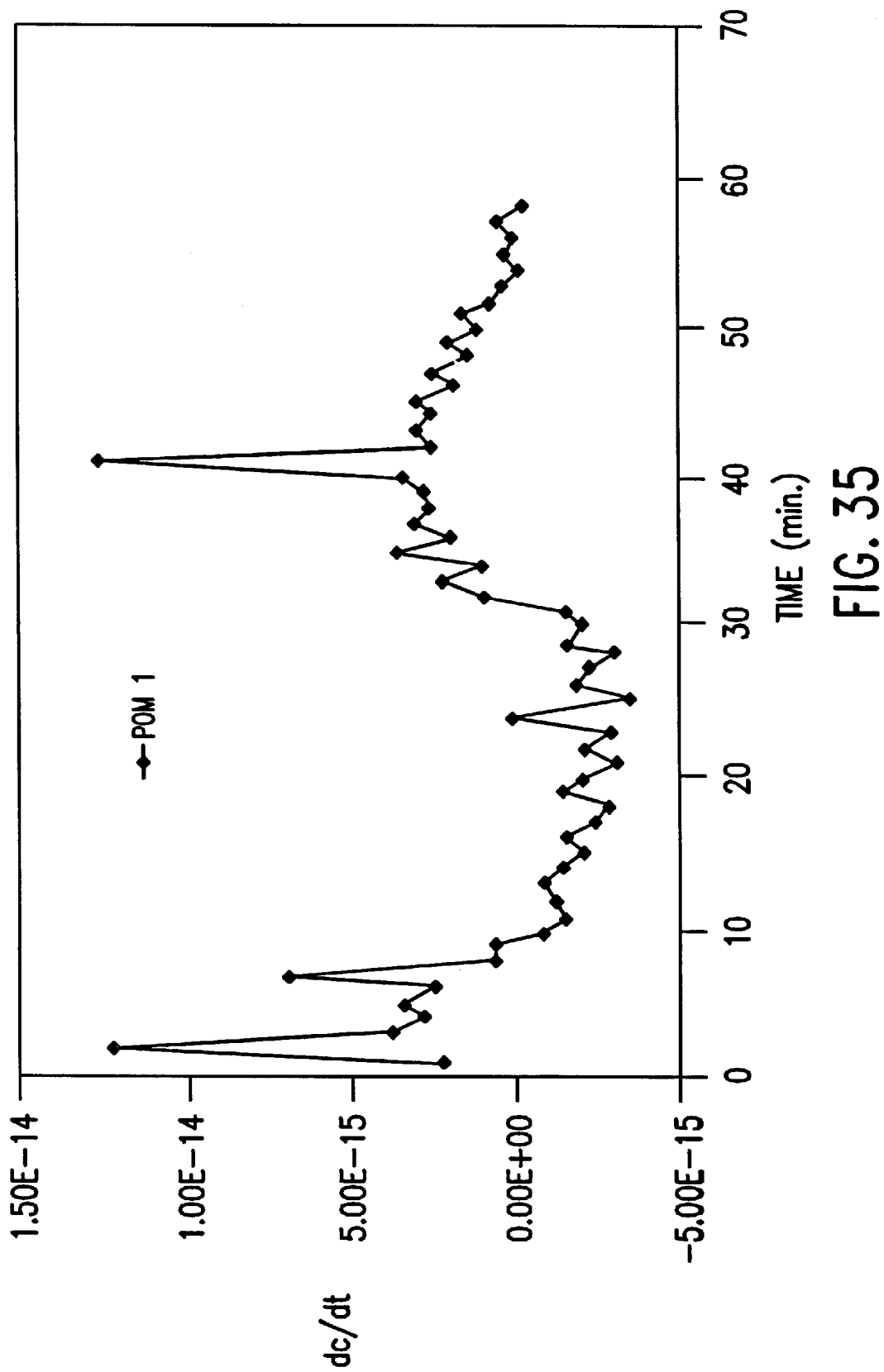
FIG. 35 is a graph showing the derivative of capacitance with respect to time versus time when a piece of dough is frozen.

FIG. 35 shows the derivative of capacitance with respect to time versus time when a piece of dough is frozen.

The values of the abscissa when the curve of the derivative dc/dt crosses the abscissa are the times when the capacitance is minimum or maximum in FIG. 29 which shows the capacitance versus time.

Therefore, in the actual freezing process of a food article, the start and completion of freezing are easily recognized by obtaining the derivative of capacitance in real time.

Figure 36:
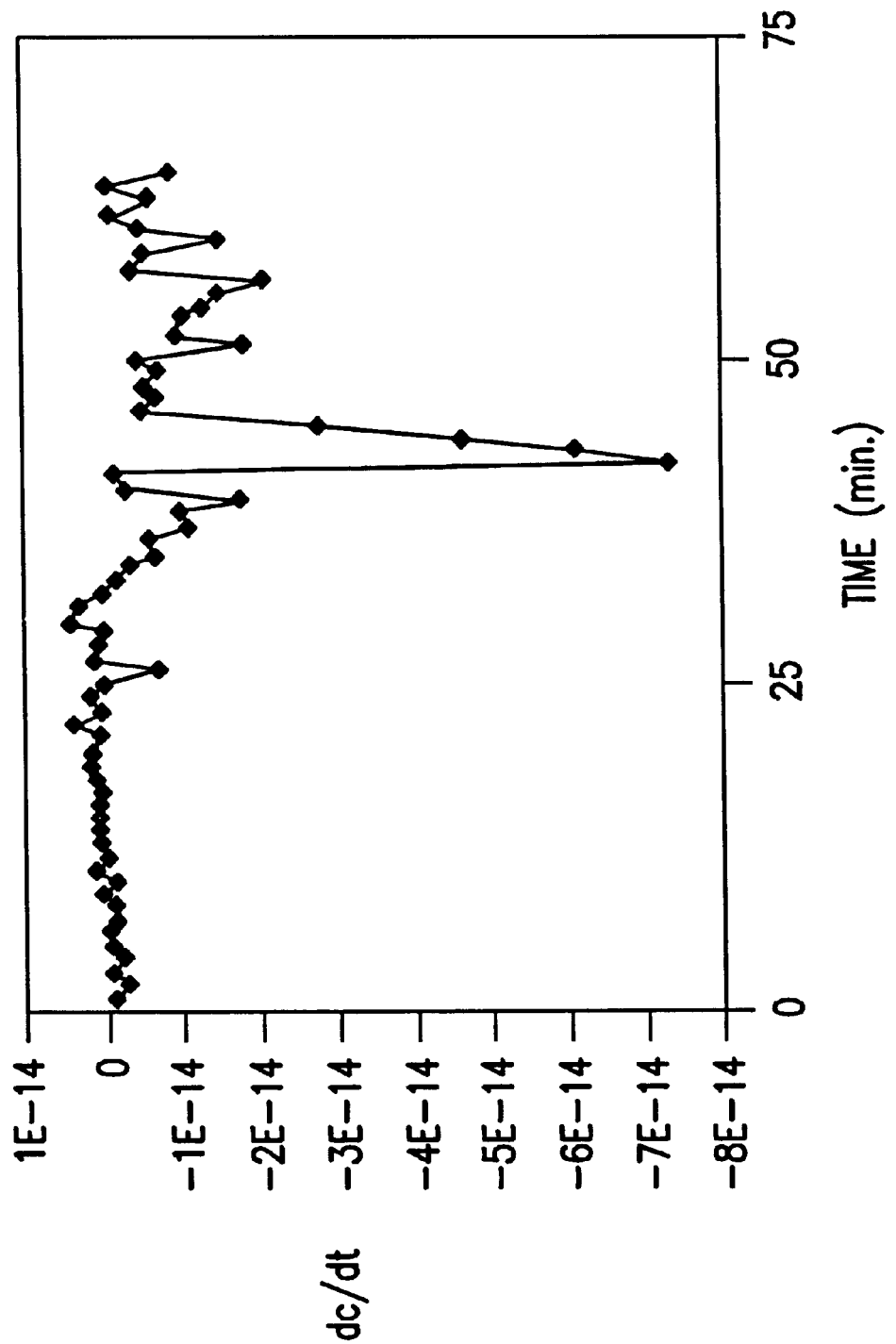
FIG. 36 is a graph showing the derivative of capacitance with respect to time versus time when a piece of dough is unfrozen.

FIG. 36 shows the derivative of capacitance with respect to time versus time when a piece of dough is unfrozen.

The values of the abscissa when the curve of the derivative dc/dt crosses the abscissa are the times when the capacitance is minimum or maximum in FIG. 32 which shows the capacitance versus time.

Therefore, in an actual freezing process of a food article, the start and completion of unfreezing are easily recognized by obtaining the derivative of capacitance in real time.

It is recognized from the description above that the capacitance largely changes at freezing and thawing point and the state of freeze/unfreeze of a food article is determined by the change of the capacitance. The pattern of the relations between the capacitance, temperature, and lapse of time is different according to the kind of food article. By the conventional method of detecting temperature a number of temperature sensors are needed for measuring temperature at a number of points, but by the noncontact capacitance measuring method according to the present invention it is possible to detect the change of temperature-dependent physical properties of food without contacting and damaging the food article.

Generally, freezing point coincides with melting point, but in this experiment melting point is lower than freezing point, which is a phenomenon often experienced in actual operations in food factories. Considering time sequence, in the process of freezing substances of higher freezing point start freezing earlier and a large portion of the food freezes in relative higher temperature zone. Contrary to this, in the unfreezing process substances of lower freezing point change from solid to liquid earlier and substances of higher freezing point thaw later. This is the reason for the difference of the starting temperature of freezing and that of unfreezing.

From FIG. 19, FIG. 21, FIG. 25, FIG. 28, FIG. 29, FIG. 32, FIG. 35, FIG. 36 which show the variation of the capacitance and derivative of the capacitance with respect to time with the lapse of time, what state the food is in can be grasped.

As described above, existence of a correlation between the capacitance and temperature of a food article and ethyl alcohol was recognized. Particularly, in the case of food, the pattern of change in capacitance and their derivatives in freezing and unfreezing process are different according to the kind of food article, and from these measurement data the state of freeze and unfreeze is determined, which enables the improvement in the control of quality of a food article and control of operation of a freezing/unfreezing apparatus by detecting the capacitance of food article.

(IV) Detection of Inclusion of Foreign Matter.

A food including foreign matter is not clean and sanitary and a food with a hollow in it is low in value as merchandise.

Therefore, the detection of presence/absence of foreign matter and a hollow is also important. The possibility of detection of foreign matter and a hollow in a food article by capacitance measurement was investigated. Rice cake and hamburger was used as test samples and paper clip as foreign matter.

Figure 8A:
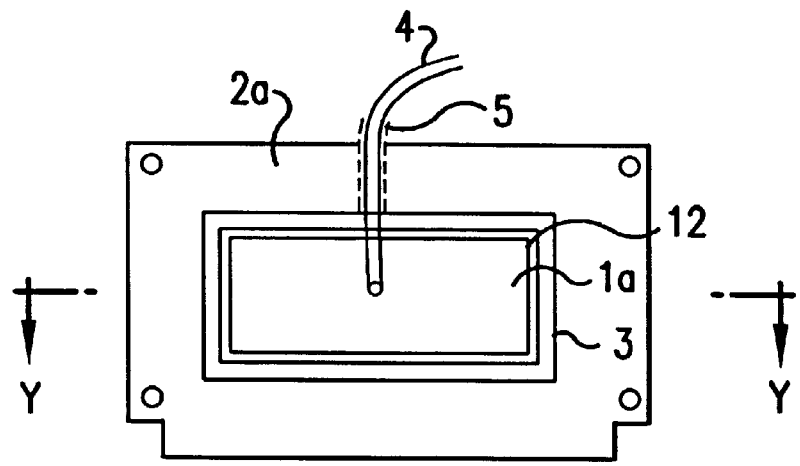
FIG. 8 is a schematic representation showing a concrete form of a positive electrode of an embodiment of a capacitance sensor according to the present invention; (A) is a plan view, (B) is a side view.
Figure 8B:
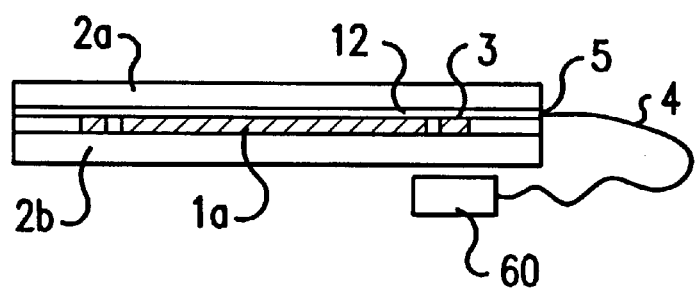

FIG. 8 is an embodiment of a capacitance sensor of single-polar/grounded type; (A) is a plan view, (B) is a sectional view along line Y—Y.

Figure 9:
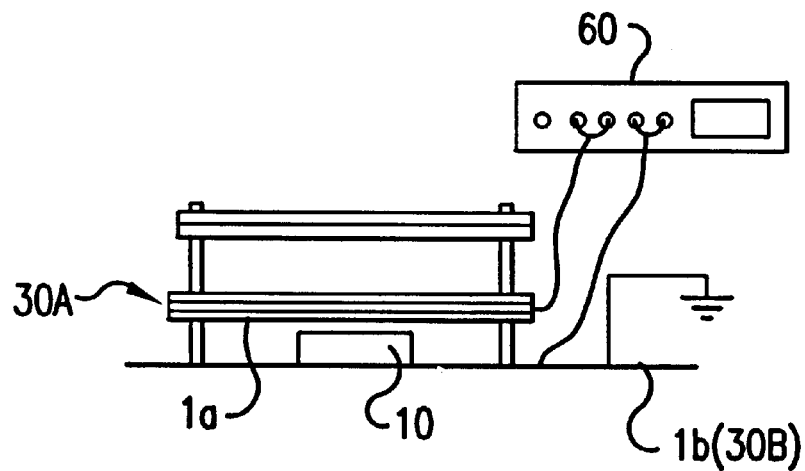
FIG. 9 is a side view showing an embodiment in which a capacitance sensor composed of the positive electrode of FIG. 8 and a grounded electrode is used for detecting inclusion of foreign matter.

FIG. 9 is an embodiment in which the capacitance sensor of one-polar/grounded type is used for detecting inclusion of foreign matter. In FIG. 8 and FIG. 9 is used the same reference numeral as that of FIG. 6 for the same component. Of a pair of electrodes 30A and 30B, a positive sensor electrode 30A provided with the electric force line diffusion prevention frame 3 as shown in FIG. 6(A) and FIG. 6(B) is used as the positive sensor electrode 30A and as the negative sensor electrode 30B is used an electrode 1b made of a copper plate of width of 1000 mm, length 1500 mm, and thickness 0.2 mm, which is grounded.

In the case the capacitance of a food article is measured with a pair of sensor electrodes 30A and 30B, of which the grounded electrode 30B has an almost finite area compared to that of the electrode 30A, the capacitance measurement shows apparent difference between the case with air layer only in the space between the electrodes and the case with air layer and a food article as shown below in TABLE 1 and TABLE 2.

TABLE 1

| Article measured | capacitance |
| --- | --- |
| Air | 4.0402 pF |
| Rice cake(1 piece) | 5.1171 pF |
| Rice cake(2 pieces) | 5.8875 pF |
| Rice cake(2 pieces) + paper clip(1 piece) | 5.1242 pF |
| Rice cake(2 pieces) + paper clip(2 pieces) | 5.1279 pF |
| Rice cake(2 pieces) + paper clip(3 pieces) | 5.1350 pF |

TABLE 2

| Article measured | capacitance |
| --- | --- |
| Air | 4.0370 pF |
| Hamburger | 6.4616 pF |
| Hamburger + paper clip(1 piece) | 6.4799 pF |
| Hamburger + paper clip(2 pieces) | 6.4983 pF |
| Hamburger + paper clip(3 pieces) | 6.5165 pF |

It is confirmed from the experiment that the capacitance between the electrodes differs in accordance with the area of the food article under the projected area of the non-grounded electrode. It is clarified that, as the value of capacitance varies when foreign matter is included in the food article, the inclusion of foreign matter is determined from the capacitance.

(V) Measurement in the Case of a Continuous Freezing Apparatus.

Figure 10A:
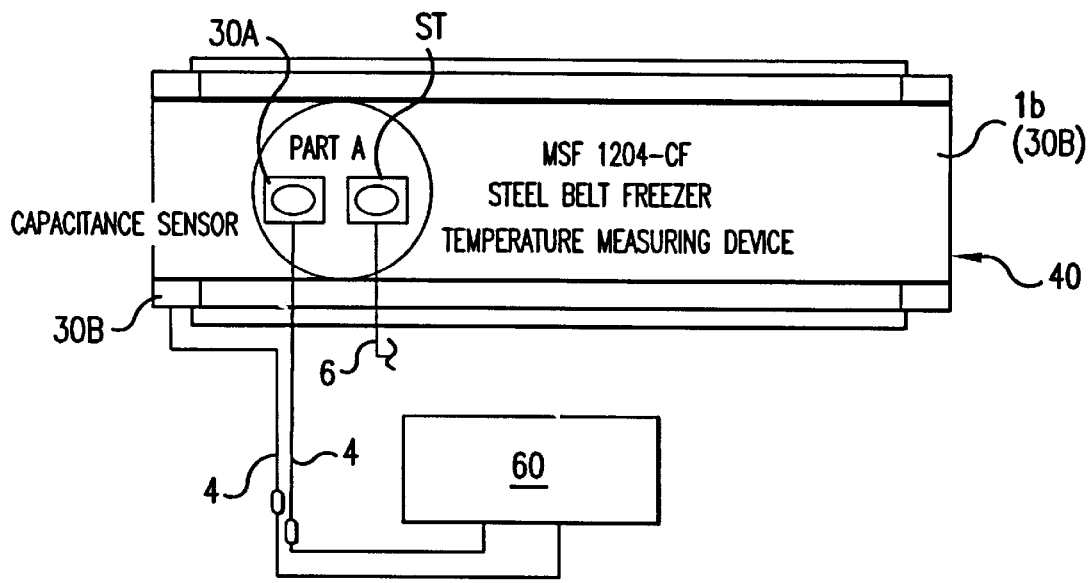
FIG. 10 is a schematic representation of the principal part of an embodiment in which an embodiment of a capacitance sensor according to the present invention is applied to a continuous freezing apparatus; (A) is a plan view, (B) is a vertical sectional view.
Figure 10B:
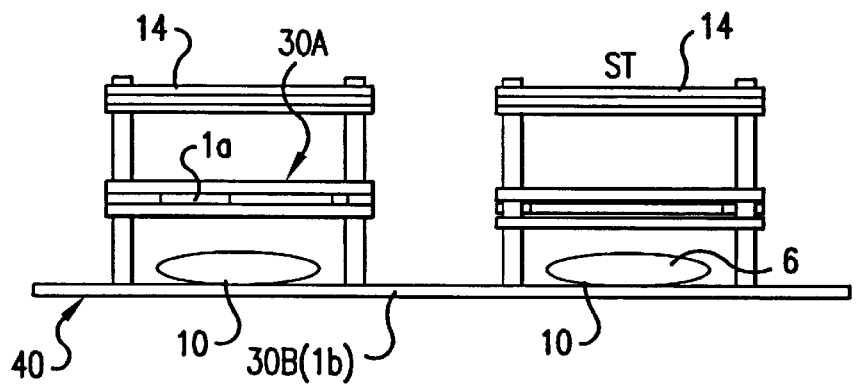

Detection possibility was investigated in the case where the noncontact capacitance sensor 30 is disposed facing the steel belt-form sensor electrode 30B which is the electric conductive belt of the continuous freezing apparatus B of FIG. 5. As shown in FIG. 10, the one end of the lead cable is connected to the earth terminal and fastened together with the screw on the cover of the terminal frame. The temperature of a food article was measured with a direct type temperature sensor such as thermocouple or thermistor inderting into the food article to the center.

FIG. 10 is a schematic sketch of an embodiment in which the capacitance sensor 30 is applied to a continuous freezing apparatus. The electric conductive steel belt is used as the sensor electrode 30B which is continuously transferred in longitudinal direction by a motor (not shown). A mesh belt may be used instead of the steel belt.

The capacitance sensor 30 and a dummy sensor ST having the same size and construction as the capacitance sensor 30 were placed adjacent to each other on the steel belt-form sensor electrode 30B. The locations was near the outlet door of the freezing/unfreezing room 38 where change of test samples was possible. The test samples (food articles) 10 were placed on the steel belt-form sensor electrode 30B directly underneath the sensor electrode 30 and dummy sensor ST respectively, and temperature and capacitance variation with the lapse of time in freezing process were measured. The temperature was measured by inserting the tip of a thermocouple to the center of the food placed under the dummy sensor ST.

In the case the grounded metal belt of the steel belt-form electrode is used for the electrode 1b, it causes complication of the apparatus to connect an earth cable to the transferring belt all the time and is not preferable from a sanitary point of view. So the measurement was performed, fastening one end of the earth cable and lead cable together with a screw on the stainless steel terminal cover which is not moving part located at the drive side. The result was, the same capacitance value was obtained as when the earth cable was connected to the belt, and so in the experiment the earth cable and lead cable were connected to the stainless steel terminal cover located at the drive side. The connection may be done at any part where electric connection with the steel belt-form (or mesh belt-form) sensor electrode 30B exists by metal contact or connection.

The relations between the lapse of time, temperature, and capacitance were investigated in the process of freezing a hamburger by the apparatus described above.

Figure 37:
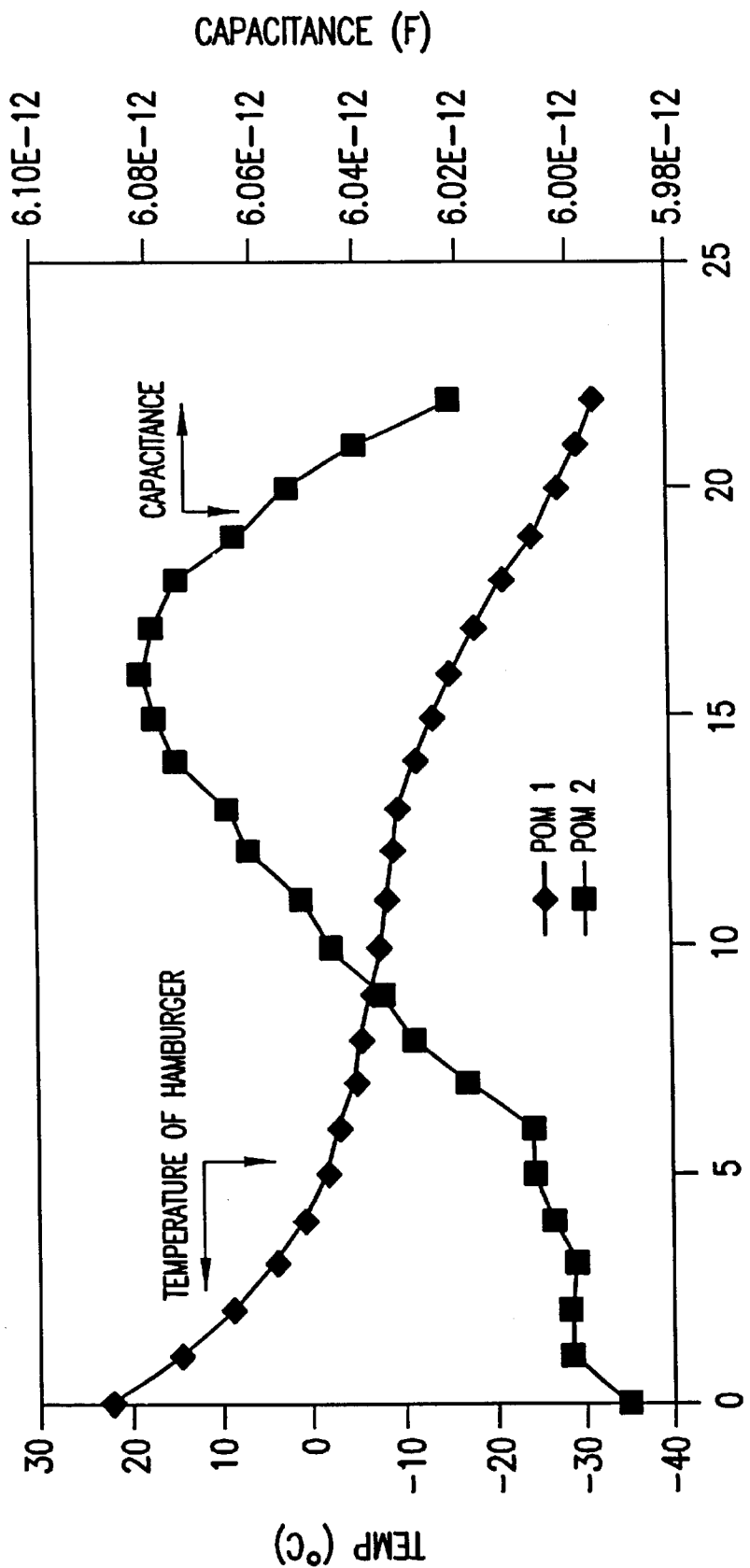
FIG. 37 is a graph showing the change of temperature and capacitance of a hamburger with respect to time series when the same is under quick freezing in a continuous freezing apparatus.
Figure 38:
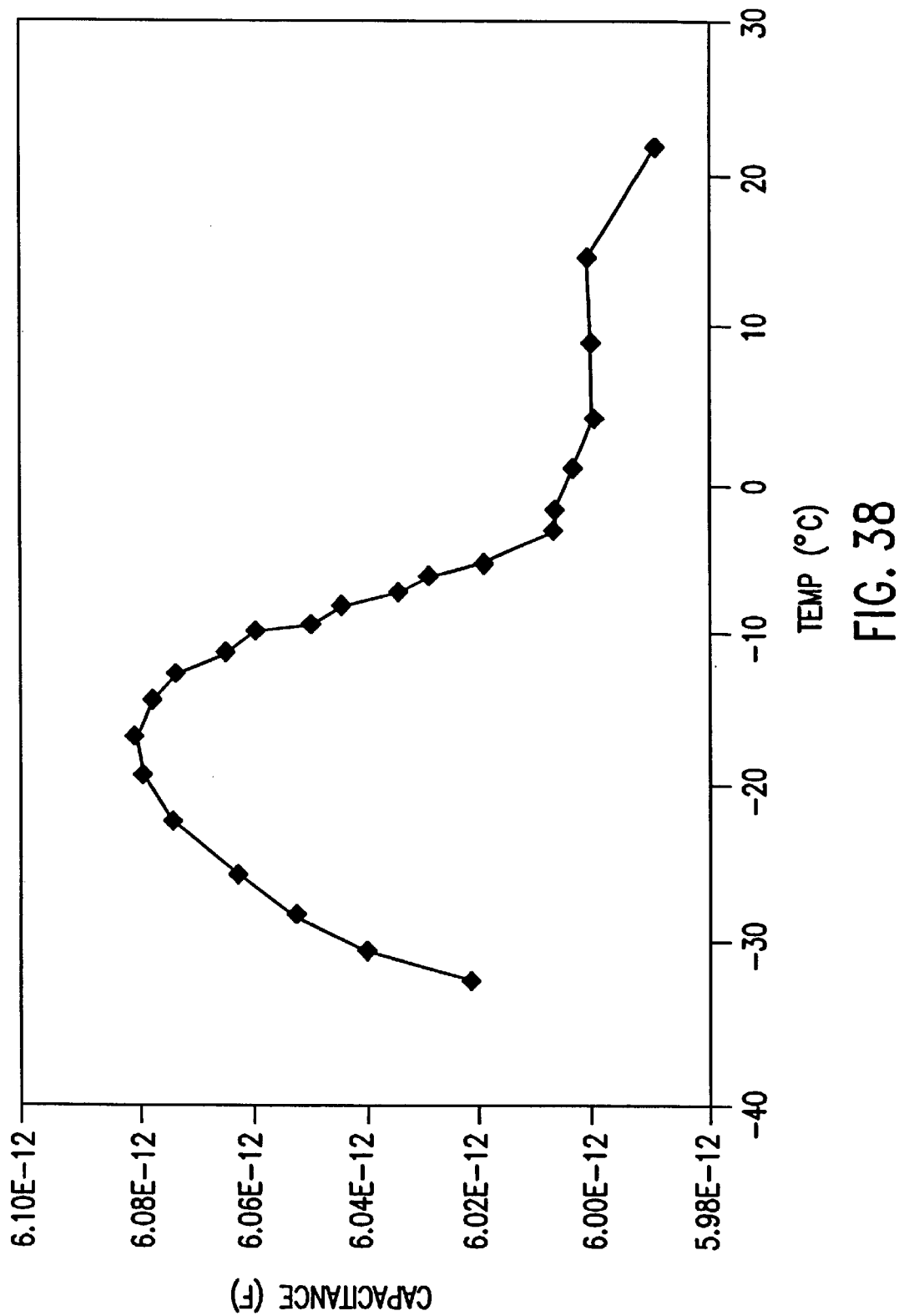
FIG. 38 is a graph showing the relation between temperature and capacitance of a hamburger when the same is under quick freezing, which relation shows the change of state of freezing (frozen state).

The temperature at the center of the hamburger is estimated to be −2.7±0.2° C. at the start of freezing and −14.8° C. when the freezing of all part of the hamburger is completed, from FIG. 37 which shows the change of temperature and capacitance with the lapse of time and FIG. 38 which shows capacitance vs. temperature.

In the case of freezing in which heat is taken away uniformly from the periphery of the food article with considerable expenditure of time, as the temperature difference, or temperature gradient in the food article is small and the whole of the food article freezes nearly at the same time or in a short period, the temperature when freezing of the whole of the food article is completed, i.e. the temperature when the value of second derivative of the capacitance shows peak is nearly the same to that of freezing point.

In this experiment, as the hamburger was quick frozen with the lower face kept contact with the stainless steel plate of −40° C. and the upper face with the air of −35° C., the temperature gradient in the hamburger was large and frozen part coexist with not-frozen part in the food article. As freezing proceeds from the periphery to the interior, there is a large difference between the temperature measured at the center of the food and that when freezing of all part of the food is completed. In both cases, the value of capacitance rises with the start of freezing of the hamburger 10, regardless of its portion, and reaches the maximum when the whole of it completes freezing. Also, the capacitance changes in accordance with the rate of freezing.

As described above, a correlation between the change of capacitance and the change of physical property of the hamburger was recognized.

Figure 42:
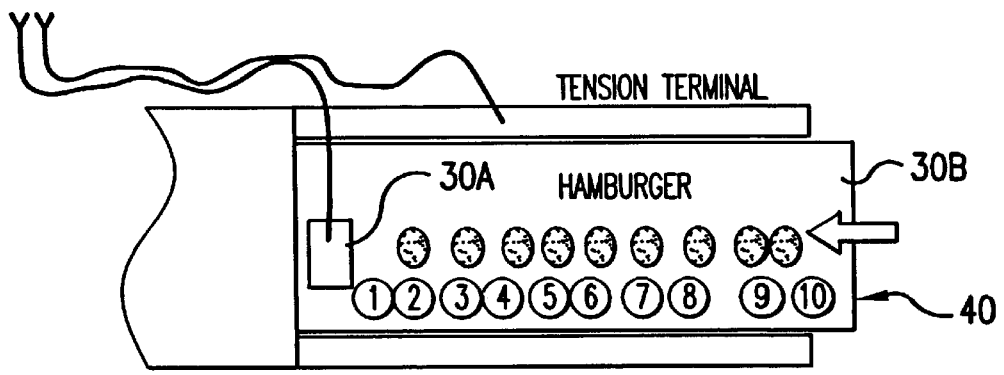
FIG. 42 is a schematic plan view showing the situation of measurement by a capacitance sensor, in which hamburgers ①~⑩ disposed on the conveyor at the tension terminal part of a continuous freezing apparatus are passing by the capacitance sensor.
Figure 43:
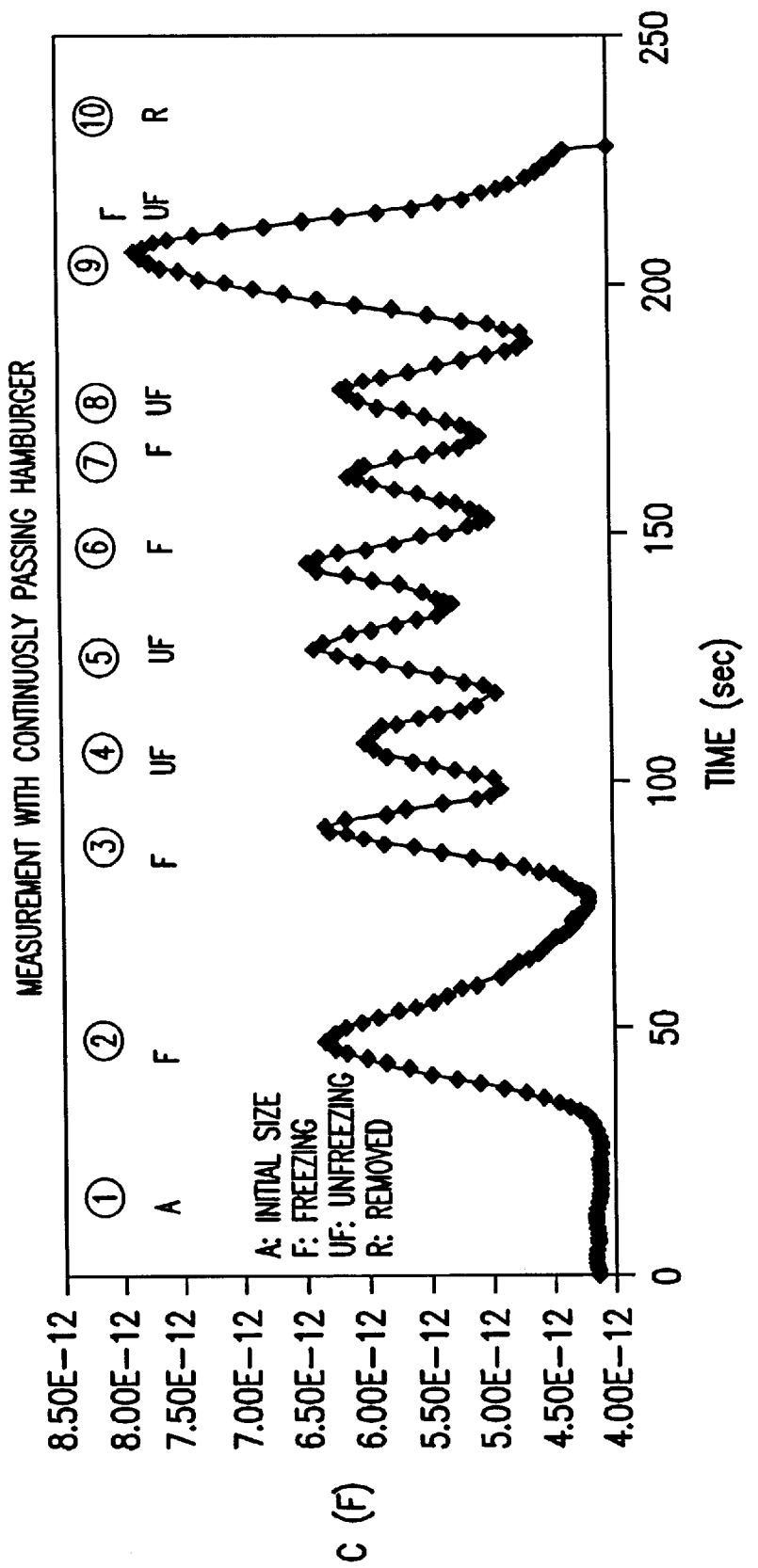
FIG. 43 is a graph showing the change of capacitance of the hamburgers ①~⑩ measured by the way shown in FIG. 42.

It was recognized from FIG. 42, TABLE 3, and FIG. 43 that, when food articles arranged on the transferring belt-form sensor electrode 30B with arbitrary spacing distance pass by the capacitance sensor located at a fixed position, the value of capacitance is proportional to the area of an article measured crossing the lines of electric force and changes in accordance with the change in physical property of the article measured.

Figure 44:
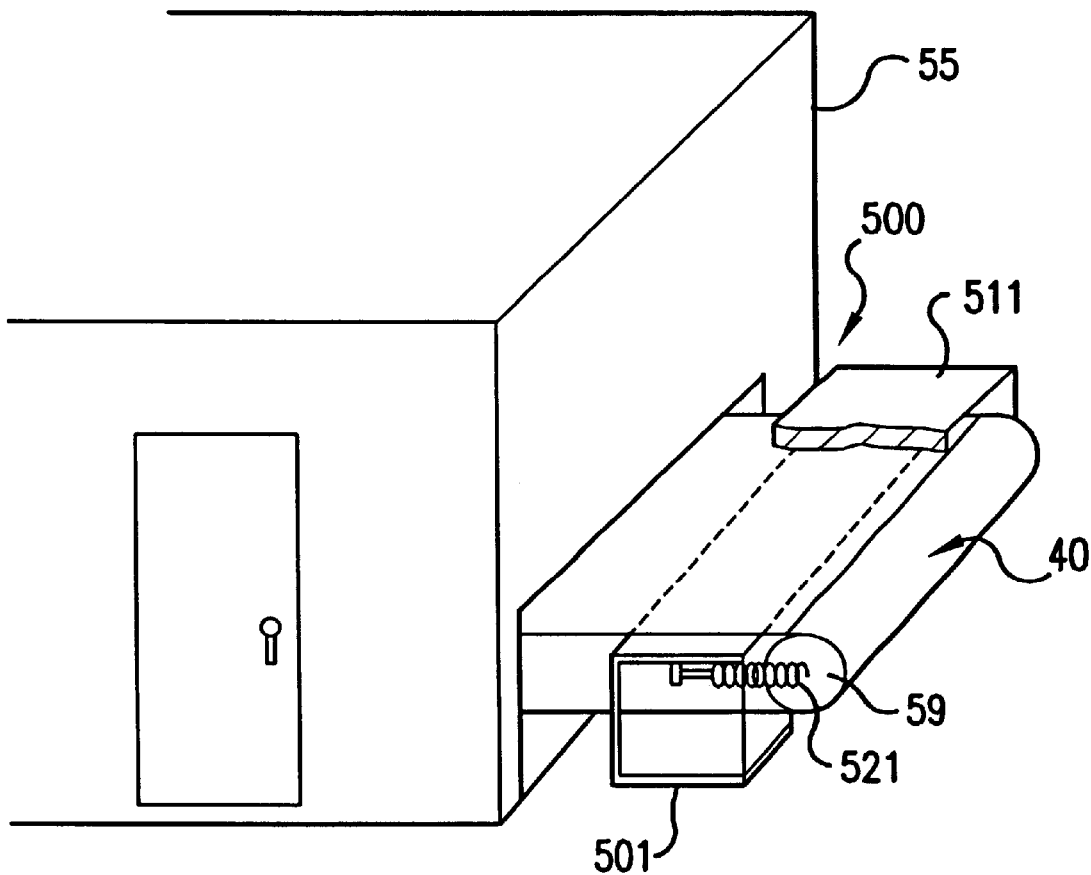
FIG. 44 is a fragmentary perspective view showing the construction of the tension terminal side of a steel belt freezer.

By the way, the construction of the tension terminal 500 of the steel belt freezer is shown in FIG. 44. The tension terminal 500 is the part where a rotating drum 59 is pushed by way of a tension spring 521 to give tension to the belt 40 for the prevention of bending of the belt 40 by the weight of food articles transferred on it. A drive terminal (not shown) for driving the belt 40 is provided at the other side of the tension terminal 500. A terminal frame 511 surrounds the belt crosswise with a stainless steel cover 511 on it.

TABLE 3

Continuous measuring of frozen, unfrozen hamburger on steel transfer belt.

| Sample order | Sample pass time (sec.) | | State of Sample | Remarks |
| --- | --- | --- | --- | --- |
| | entered | passed | | |
| 1 | 0 | 33 | air | |
| 2 | 34 | 70 | frozen | −35° C.~−30° C. |
| 3 | 71 | 98 | frozen | −35° C.~−30° C. |
| 4 | 99 | 117 | unfrozen | 18° C.~22° C. |
| 5 | 118 | 135 | unfrozen | 18° C.~22° C. |
| 6 | 136 | 153 | frozen | −35° C.~−30° C. |
| 7 | 154 | 171 | frozen | −35° C.~−30° C. |
| 8 | 172 | 198 | unfrozen | 18° C.~22° C. |
| 9 | 199 | 227 | frozen unfrozen | introduced in the order written in left |
| 10 | 228 | 236 | air | sensor removed |

Because of hand held sensor, capacitance fluctuated due to the fluctuation of the sensor.

(VI) Multi-polar Type Capacitance Sensor.

Figure 11A:
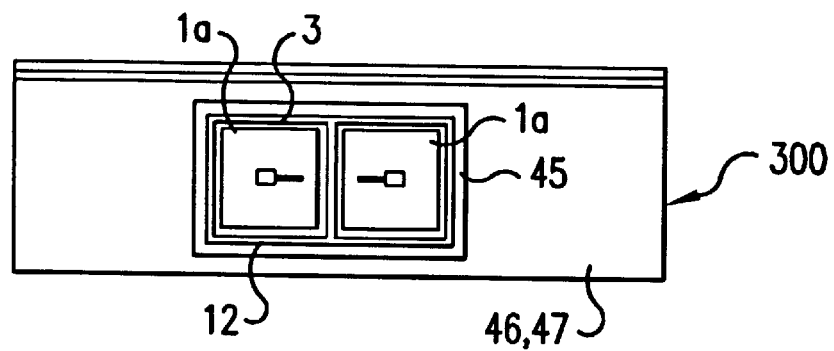
FIG. 11 is a schematic representation of the principal part of an embodiment of a multi-polar sensor according to the present invention; (A) is a plan view, (B) is a vertical sectional view.
Figure 11B:
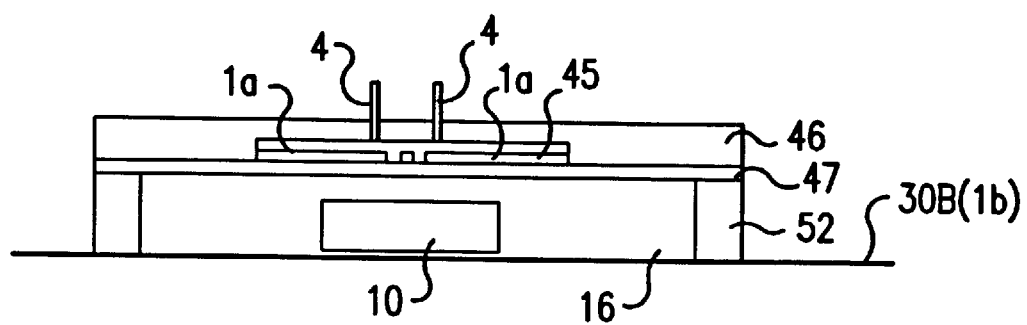

FIG. 11 is a schematic sketch of the principal part of an embodiment of multi-polar type capacitance sensor according to the present invention; (A) is a plan view, (B) is a sectional view.

Figure 16:
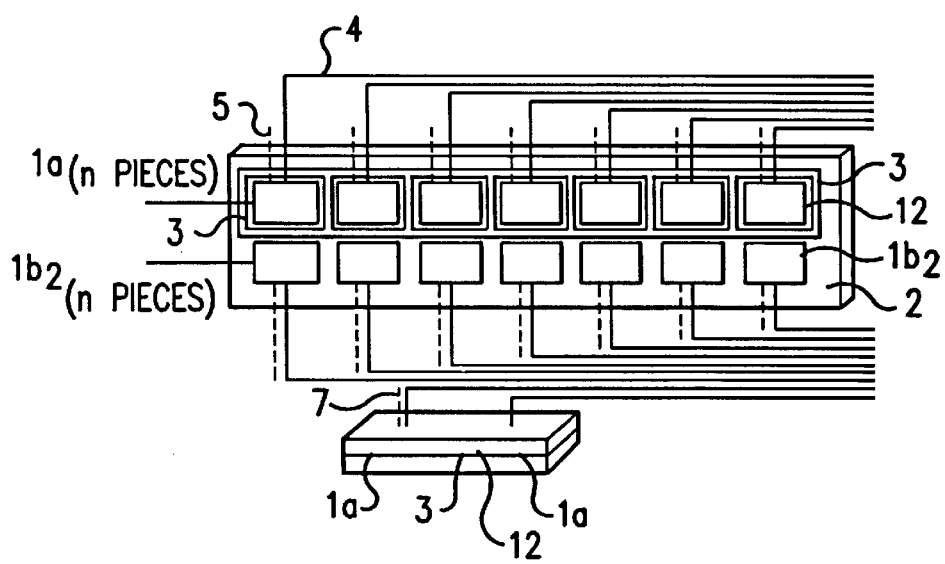
FIG. 16 is a top perspective view of an another embodiment of a capacitance sensor composed of a number of positive electrodes and a number of negative electrodes (individual electrode plates) corresponding to each of the positive electrodes disposed on the same plane according to the present invention and a side perspective view of its principal part.

In the embodiment, the number of the electrode 1a composing the sensor electrode 30A (300) which is one of the two sensor electrodes 30A and 30B facing each other across the space 16 as shown in FIG. 16, is greater than or equal to 2. Here, two electrode 1a, 1a were adopted for the purpose of clarifying the relation between the separation/combination of electrodes and capacitance.

The shielding mesh of the shield, coaxial cable 4 connected to the electrodes 1a, 1a is soldered to the electric force line diffusion prevention frame 3. The positive sensor electrode 30A (300) comprises electrodes 1a, 1a and the electric force line diffusion prevention frame 3 surrounding the electrodes 1a, 1a with a proper spacing 12 to evade metal contact with each other are disposed on the acrylic fiber plate 45 in similar way as shown in FIG. 6. The electrode plate 300 composing positive sensor electrode 30A is composed by sandwiching and fixing the electrodes 1a, 1a and the electric force line diffusion prevention frame 3 on the acrylic fiber plate 45 with the acrylic fiber plates 46, 47 which have enough area for covering the electric force line diffusion prevention frame 3. The multi-polar electrode plate 300 is supported on spacers 52 to keep a distance from the other electrode plate 1b (30B) to secure the space 16.

(VII) Determination of an Internal Hollow, Composition by Multi-polar Sensor.

Capacitance was measured using a single multi-polar sensor 300 or two multi-polar sensors connected in parallel and changing the direction and position of a rice cake, an article to be measured, relative to the multi-polar sensor.

Figure 12:
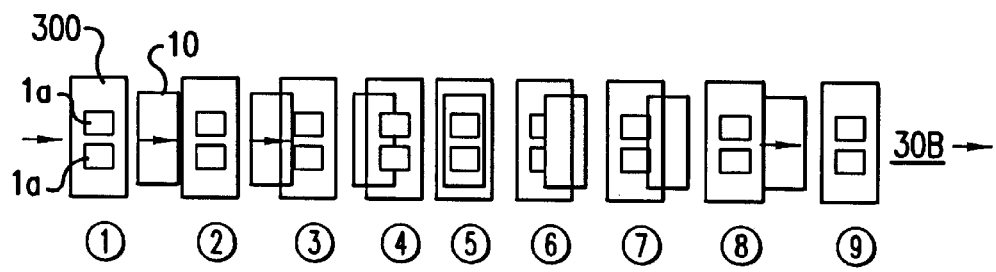
FIG. 12 is a schematic representation showing the shift position of a rice cake of rectangular shape, an article to be measured, relative to a multi-positive-polar sensor electrode in the sequence of ①~⑨ in the case the rice cake is transferred on a conveyor in an attitude parallel to the longitudinal direction of the sensor electrode (longitudinal disposition).

FIG. 12 is a schematic representation showing the relative position of a rice cake of rectangular shape, an article to be measured, to the multi-positive-polar electrode sensor in the sequence of ①~⑨ in the case the rice cake is transferred on the conveyor in an attitude parallel to the longitudinal direction of the sensor electrode (hereafter referred to as longitudinal disposition).

Figure 13:
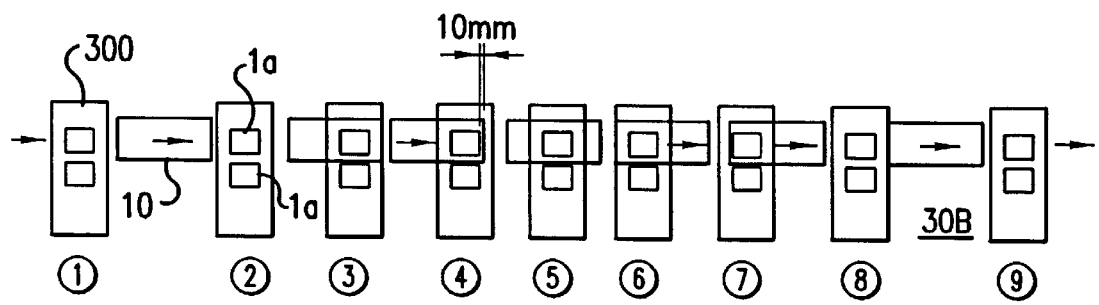
FIG. 13 is a schematic representation showing the shift of position of a rice cake of rectangular shape, an article to be measured, relative to a multi-positive-polar sensor electrode in the sequence of ①~⑨ in the case the rice cake is transferred on a conveyor in an attitude perpendicular to the longitudinal direction of the sensor electrode (lateral disposition).

FIG. 13 is a schematic representation showing the relative position of a rice cake of rectangular shape, an article to be measured to the multi-positive-polar electrode sensor in the sequence of ①~⑨ in the case the rice cake is transferred in an attitude perpendicular to the longitudinal direction of the sensor electrode (hereafter referred to as lateral disposition).

Capacitance was measured when the position of the rice cake was ①~⑨ in the case of longitudinal disposition and lateral disposition.

Figure 39:
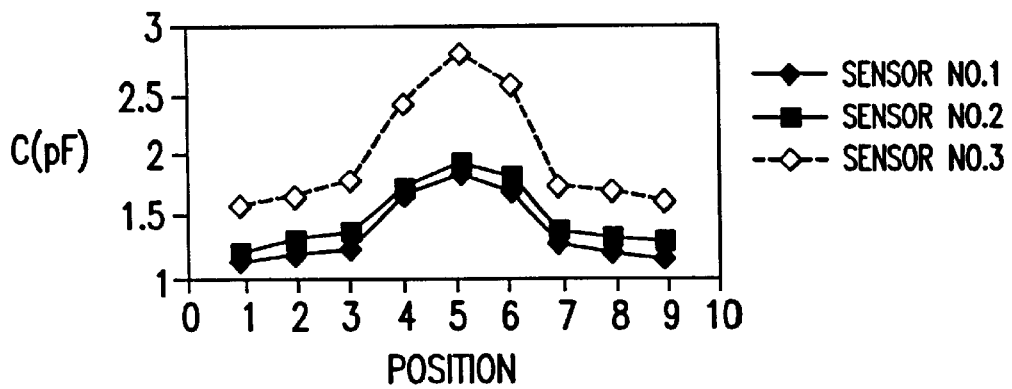
FIG. 39 is a graph showing the capacitance versus the position of a rice cake when the rice cake is transferred disposed in an attitude parallel to the longitudinal direction of the sensor electrode (longitudinal disposition) corresponding to FIG. 12.
Figure 40:
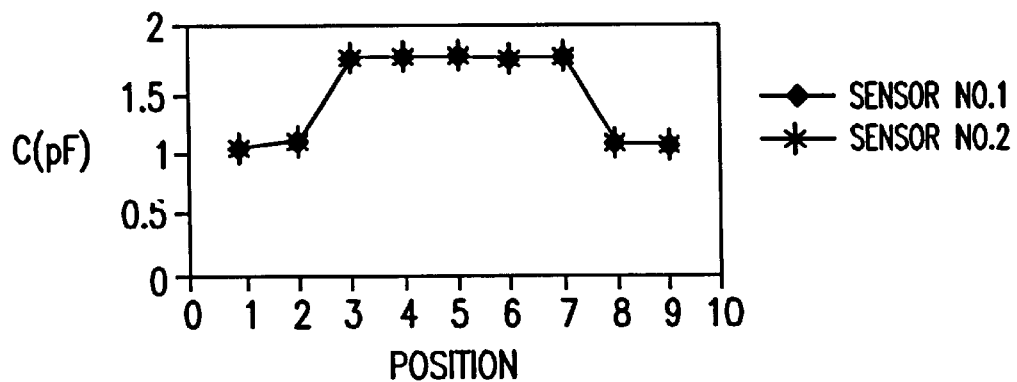
FIG. 40 is a graph showing the capacitance versus the position of a rice cake when the rice cake is transferred disposed in an attitude perpendicular to the longitudinal direction of the sensor electrode (lateral disposition) corresponding to FIG. 13.

The results of measurement are shown in TABLE 4 and TABLE 5 below and in FIG. 39 and FIG. 40. It is recognized that the measured capacitance is proportional to the number of the electrodes used and the area of the rice cake covered by the projection of the electrode of the sensor. The capacitance is maximum when all of the projected area of the electrode or electrodes cover the rice cake in either case of longitudinal and lateral disposition. Further, the changing pattern of capacitance differs according to the attitude of the rice cake relative to electrode. This indicates that various information can be obtained with the same article measured according to the combination of electrodes. In the case of FIG. 12 passage or existence of an article is recognized and in the case of FIG. 13 more detailed information of an article along the transfer direction can be obtained. Therefore, by the combination of FIG. 12 and FIG. 13 or TABLE 4 and TABLE 5, and further from the resultant of the capacitance measured by the electrode 1a, 1a, more accurate evaluation of an article is possible, including the shape.

TABLE 4

| Position | Electrode No. | | |
|---|---|---|---|
| | 1 | 2 | 1 + 2 |
| 1 | 1.0948 E-12 | 1.1696 E-12 | 1.6114 E-12 |
| 2 | 1.2083 E-12 | 1.2563 E-12 | 1.6882 E-12 |
| 3 | 1.2261 E-12 | 1.3009 E-12 | 1.7594 E-12 |
| 4 | 1.6378 E-12 | 1.7254 E-12 | 2.4464 E-12 |
| 5 | 1.8507 E-12 | 1.9169 E-12 | 2.8858 E-12 |
| 6 | 1.6869 E-12 | 1.7641 E-12 | 2.5814 E-12 |
| 7 | 1.2387 E-12 | 1.2962 E-12 | 1.7557 E-12 |
| 8 | 1.1985 E-12 | 1.2254 E-12 | 1.6868 E-12 |
| 9 | 1.0948 E-12 | 1.1696 E-12 | 1.6114 E-12 |

TABLE 5

| Position | Electrode No. | |
|---|---|---|
| | 1 | 2 |
| 1 | 1.0905 E-12 | 1.1026 E-12 |
| 2 | 1.1409 E-12 | 1.1485 E-12 |
| 3 | 1.8195 E-12 | 1.8218 E-12 |
| 4 | 1.8278 E-12 | 1.8388 E-12 |
| 5 | 1.8317 E-12 | 1.8377 E-12 |
| 6 | 1.8275 E-12 | 1.8304 E-12 |
| 7 | 1.8184 E-12 | 1.8214 E-12 |
| 8 | 1.1405 E-12 | 1.1435 E-12 |
| 9 | 1.0905 E-12 | 1.1026 E-12 |

The determination whether internal hollow is present or absent is important together with whether a rice cake meets the spec.

Figure 14:
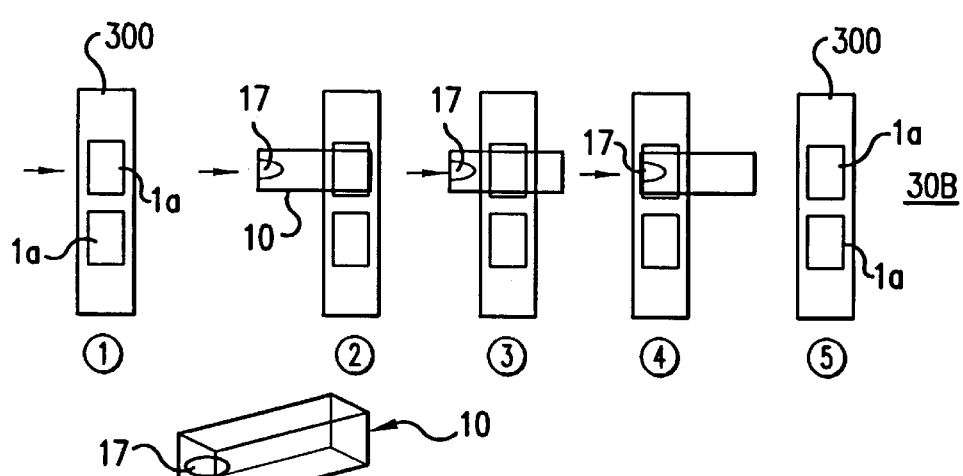
FIG. 14 is a schematic representation showing shift of position of a rice cake having a hollow in it relative to a multi-positive-polar sensor electrode in the sequence of ①~⑤ in the case the rice cake is transferred on a conveyor in an attitude parallel to the longitudinal direction of the sensor electrode (lateral disposition).

FIG. 14 is a schematic representation showing the relative position of a rectangular-shaped rice cake, an article to be measured, to the multi-positive-polar sensor in the sequence of ①~⑤ in the case the rice cake is transferred on the conveyor in an attitude perpendicular to the longitudinal direction of the sensor electrode (lateral disposition).

Figure 41:
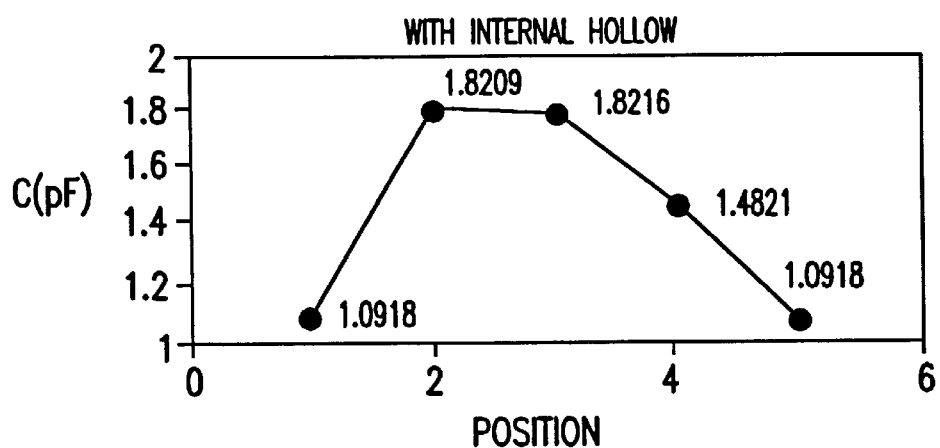
FIG. 41 is a graph showing the capacitance versus position of a rice cake when the rice cake having a hollow in it is transferred disposed in an attitude parallel to the longitudinal direction of the sensor electrode (longitudinal disposition) corresponding to FIG. 14.

In the case there is a hollow 17 in the rice cake as shown in FIG. 14, the capacitance decreased when the hollow is under the sensor as shown in TABLE 6 and FIG. 41, from which the presence/absence of internal deficiency can be determined.

If a number of bubbles are included in a rice cake, the capacitance decreases in accordance of the volume of the bubbles and if the quantity of bubbles is within the spec. or not is effectively determined.

TABLE 6

| Position | Capacitance |
|---|---|
| 1 | 1.0918 E-12 |
| 2 | 1.8209 E-12 |
| 3 | 1.8216 E-12 |
| 4 | 1.4812 E-12 |
| 5 | 1.0918 E-12 |

The difference of the position of the article to be measured relative to the multi-polar electrodes sensor corresponds to the change of the position of the article to be measured passing by under the fixed capacitance sensor 30 in the continuous freezing/unfreezing apparatus B shown in FIG. 5. Therefore, by measuring the capacitance with single or combined positive electrode plate 1a, 1a properly selected, in consideration of the transfer direction and shape of the article to be measured, from among the capacitance sensors 30 in a continuous freezing/unfreezing apparatus, information such as internal defect, size, the number, transfer pitch, transfer speed, etc. of the articles to be measured can be obtained as necessary.

The measured value of permittivity (or impedance, capacitance) and its pattern of change with the lapse of time is different in accordance with the shape of the positive electrode plates $1a$, $1a$.

In food industries, it is rare that a continuous freezing/unfreezing apparatus is used for one kind of food article but plural kinds of food article are treated at the same time. The most suitable electrode for the kind of food article, item of quality evaluation, and item of evaluation and control of the apparatus, can be composed by forming single-polar sensor, double-polar sensor, or multi-polar electrode sensor through using selected positive sensors from among the positive sensors $1a$, $1a$, individually, or combining in parallel.

Although capacitance is output in the form of permittivity, impedance, or resultant impedance according as the processing of the measurement, these have linear relation to capacitance and can be treated the same as capacitance.

(VIII) Multi-polar Capacitance Sensor on the Same Plane.

A configuration in which the positive sensor electrode 30A and the negative sensor electrode 30B (positive electrode $1a$ and negative electrode $1b$) are disposed on the same plane in contrast to that in which the positive sensor electrode 30A is disposed facing the negative sensor electrode 30B across the space 16, is possible. This type is particularly preferable in the case where the transfer table is of nonmetal, nonconductive belt, or contamination of the belt surface is severe, because in this type a substantially dielectric belt face is adopted and beneficial because it can be applied to the batch type shown in FIG. 2 as in the case with the previously described noncontact sensor in which the food is placed between the electrodes.

Figure 15:
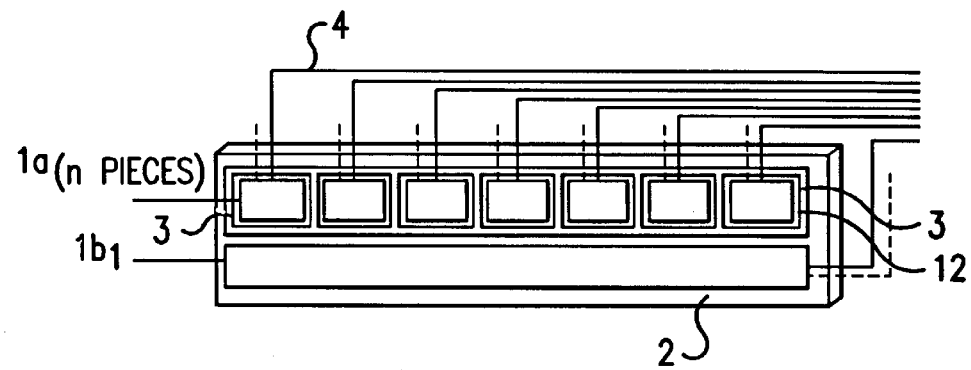
FIG. 15 is a top perspective view of an another embodiment of a capacitance sensor composed of a number of positive electrodes and a negative electrode (common electrode plate) disposed on the same plane according to the present invention.

FIG. 15 is a schematic representation of the principal part of an embodiment of a multi-polar capacitance sensor on the same plane (common electrode plate) according to the present invention, and the negative sensor electrode 30B is formed as common electrode $1b_1$. The number of n of positive electrodes $1a$, $1a$, each of which is surrounded by an electric force line diffusion prevention frame 3 with a spacing 12, and a common negative electrode $1b$ of band shape, are arranged on an insulation plate 2 made of acrylic fiber plate or the like. Each lead cable 4 is connected to each positive electrode $1a$, and the common electrode $1b$ and the electric force line diffusion prevention frame 3 are connected to the shield meshes 5 of the lead cables.

FIG. 16 is a schematic representation of the principal part of an embodiment of a multi-polar capacitance sensor on the same plane (individual electrode plate). In FIG. 15 the negative electrode is a common electrode $1b_1$, but in FIG. 16 the number n of negative electrodes $1b_2$, $1b_2$, are corresponded to the number n of the positive electrode $1a$, $1a$.

Figure 45:
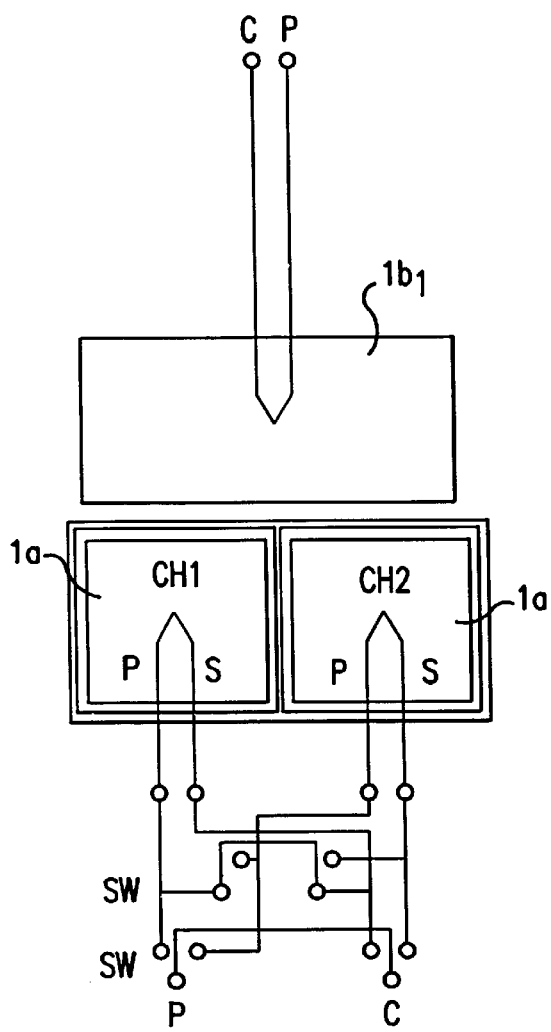
FIG. 45 is a circuit diagram of a capacitance sensor corresponding to FIG. 15, the capacitance sensor being composed of a pair of positive electrodes and a negative electrode (common electrode plate) disposed on the same plane (hereinafter this type of sensor is referred to as multi-double-polar/common electrode sensor).

FIG. 45 is a circuit diagram of the capacitance sensor corresponding to FIG. 15 showing the selection of each electrode and switch board circuit of a multi-polar capacitance sensor with a common electrode on the same plane in the case of two positive electrodes $1a$.

Figure 46:
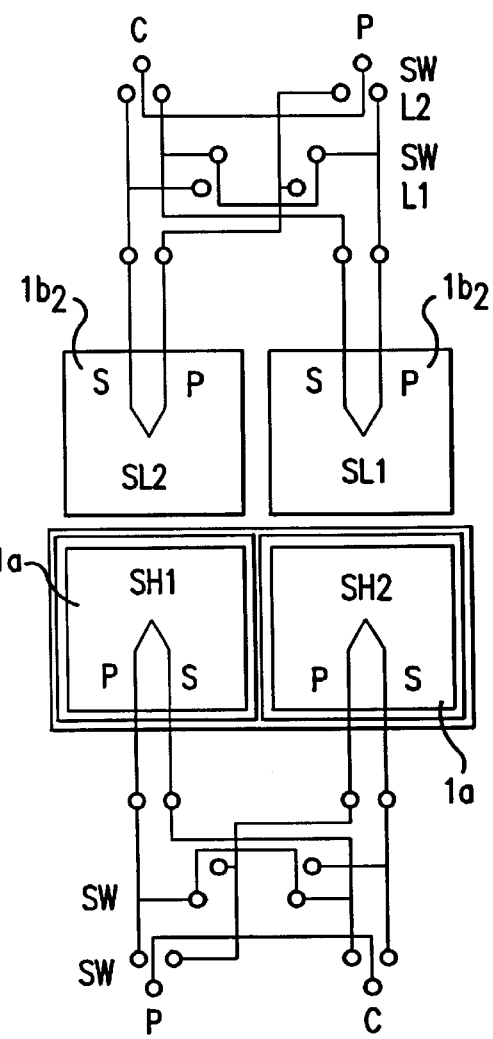
FIG. 46 is a circuit diagram of an electrostatic capacity sensor corresponding to FIG. 16, the electrostatic capacity sensor being composed of a pair of positive electrodes and a pair of negative electrodes (individual electrode plates) disposed on the same plane (hereinafter this type of sensor is referred to as multi-double-polar/individual electrode sensor).

FIG. 46 is a circuit diagram of the capacitance sensor corresponding to FIG. 16 showing the selection of each electrode and switch board circuit of a multi-polar capacitance sensor with individual electrodes on the same plane in the case of two positive electrodes $1a$.

In FIG. 45 and FIG. 46, the individual positive electrode $1a$ (CH1, CH2, SH1, SH2) and the individual negative electrode $1b$ (SL1, SL2) are copper foils of 25 mm square, and the common negative electrode $1b_1$, (C) is a copper foil of 25×55 mm.

Figure 51:
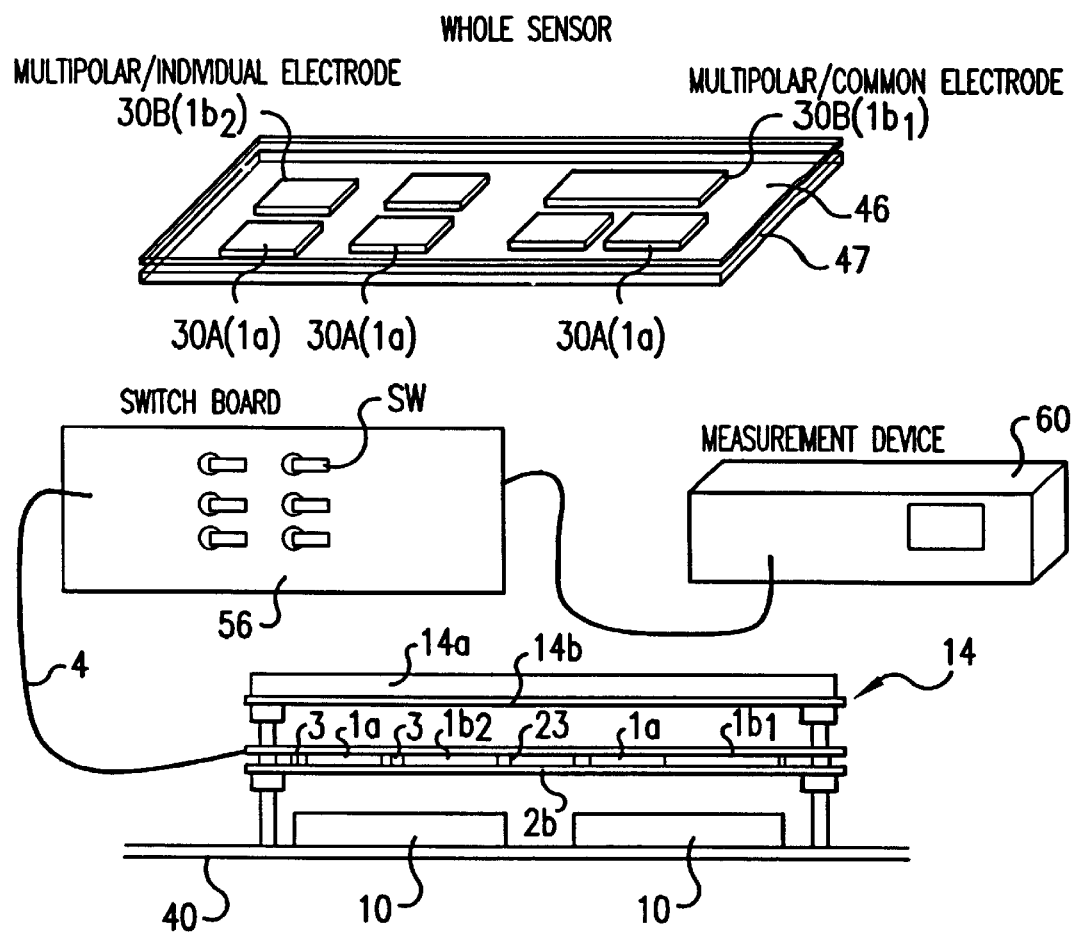
FIG. 51 is a schematic representation showing a measuring apparatus of the rice cake measuring with the multi-double-polar/common electrode sensor and the multi-double-polar/individual electrode sensor.

FIG. 51 is a schematic representation showing a measuring apparatus for measuring the rice cake transferring on the conveyor 40 in two rows with the multi-polar/individual electrode sensor on the same plane and the multi-polar/common electrode sensor on the same plane are sandwiched between the insulation plates 46 and 47, and selection and combining of each electrode is possible. The capacitance measurement section 60 is also shown.

Figure 47:
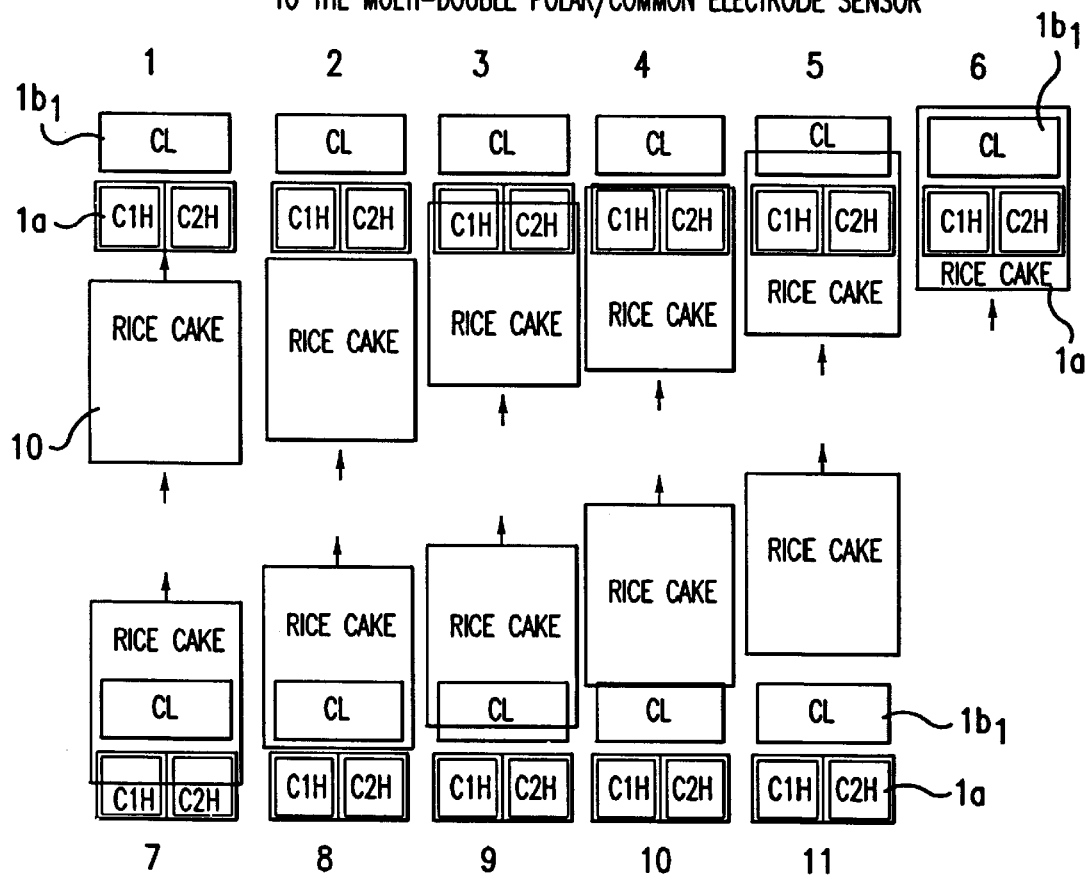
FIG. 47 is a schematic representation showing the shift of position of a rectangular rice cake, an article to be measured, relative to a multi-double-polar/common electrode sensor which corresponds to the sensor of FIG. 45, in which the rice cake is transferred on the conveyor below the sensor, in the order from ① to ⑪.

FIG. 47 shows eleven positions of the rice cake relative to the multi-polar/common electrode sensor on the same plane of FIG. 45. The measurement was performed for each of the eleven positions with single electrode C1H, C2H, and combined electrode of C1H and C2H combined by means of a switch SW. Measurement result is shown in TABLE 7 and represented in the graph in FIG. 48.

Figure 49:
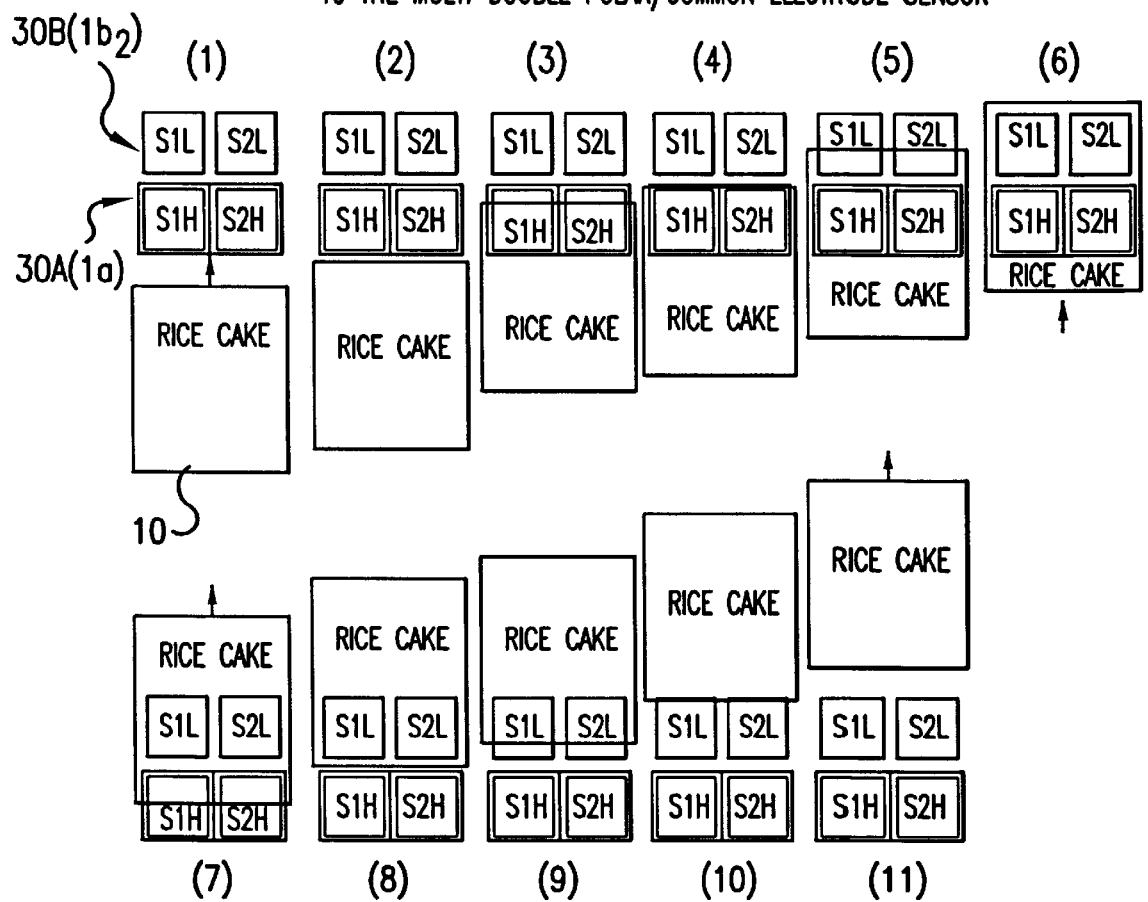
FIG. 49 is a schematic representation showing the shift of position of a rectangular rice cake, an article to be measured, relative to a multi-double-polar/individual electrode sensor which corresponds to the sensor of FIG. 46, in which the rice cake is transferred on the conveyor below the sensor, in the order from ① to ⑪.

FIG. 49 shows eleven position of the rice cake relative to the multi-polar/individual electrode sensor on the same plane of FIG. 46. The measurement was performed for each of the eleven position with single electrode S1H/S1L, S2H/S2L, and combined electrode of S1H/S1L and S2H/S2L combined by means of the switch SW. Measurement result is shown in TABLE 8 and represented in the graph in FIG. 50.

TABLE 7

| Position | Electrode No. | | |
| --- | --- | --- | --- |
| | C1 | C2 | C1 + C2 |
| 1 | 4.40 E-13 | 4.46 E-13 | 6.59 E-13 |
| 2 | 4.39 E-13 | 4.45 E-13 | 6.58 E-13 |
| 3 | 4.18 E-13 | 4.19 E-13 | 6.11 E-13 |
| 4 | 4.11 E-13 | 4.17 E-13 | 6.04 E-13 |
| 5 | 4.58 E-13 | 4.69 E-13 | 7.00 E-13 |
| 6 | 5.03 E-13 | 5.14 E-13 | 7.84 E-13 |
| 7 | 4.51 E-13 | 4.54 E-13 | 6.76 E-13 |
| 8 | 4.02 E-13 | 4.05 E-13 | 5.88 E-13 |
| 9 | 4.14 E-13 | 4.21 E-13 | 6.09 E-13 |
| 10 | 4.38 E-13 | 4.43 E-13 | 6.56 E-13 |
| 11 | 4.38 E-13 | 4.45 E-13 | 6.57 E-13 |

TABLE 8

| Position | Electrode No. | | |
| --- | --- | --- | --- |
| | S1 | S2 | S1 + S2 |
| 1 | 4.63 E-13 | 4.58 E-13 | 7.91 E-13 |
| 2 | 4.63 E-13 | 4.48 E-13 | 7.90 E-13 |
| 3 | 4.47 E-13 | 4.41 E-13 | 7.56 E-13 |
| 4 | 4.29 E-13 | 4.23 E-13 | 7.27 E-13 |
| 5 | 4.53 E-13 | 4.41 E-13 | 8.20 E-13 |
| 6 | 4.85 E-13 | 4.63 E-13 | 9.22 E-13 |
| 7 | 4.57 E-13 | 4.38 E-13 | 8.23 E-13 |
| 8 | 4.25 E-13 | 4.18 E-13 | 7.22 E-13 |
| 9 | 4.50 E-13 | 4.44 E-13 | 7.64 E-13 |
| 10 | 4.63 E-13 | 4.58 E-13 | 7.90 E-13 |
| 11 | 4.63 E-13 | 4.58 E-13 | 7.91 E-13 |

The following was clarified by the experiment:
(1) The value of capacitance in this embodiment decreases to about 25% of the value measured with the sensor used in (VI).
(2) When the article is under the projection plane of one of the two pairs of electrodes and the projection plane of the other pair of electrodes does not cover the article, the value of capacitance is smaller than when only air layer exists and decreases in proportion to the area the article is covered by the projection plane.
(3) When the article is under the projection plane of the two pairs of electrodes and all of the projection plane of one of two pairs covers the article, the value of the capacitance increases in proportion to the area the other pair of electrodes covers the article.

Figure 48:
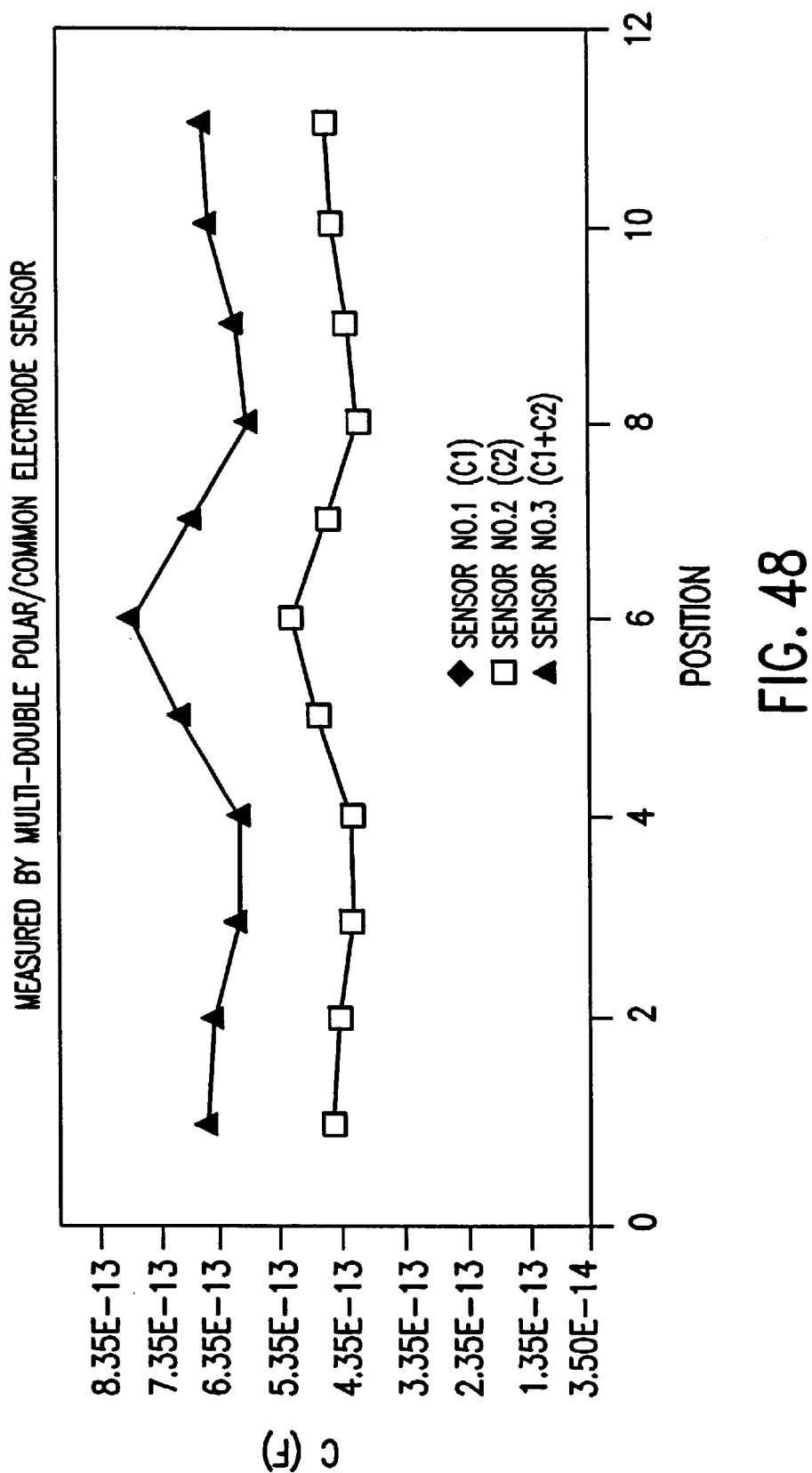
FIG. 48 is a graph showing the individual and resultant total capacitance measured with the multi-double-polar/common electrode sensor versus position of the rice cake corresponding to FIG. 47.
Figure 50:
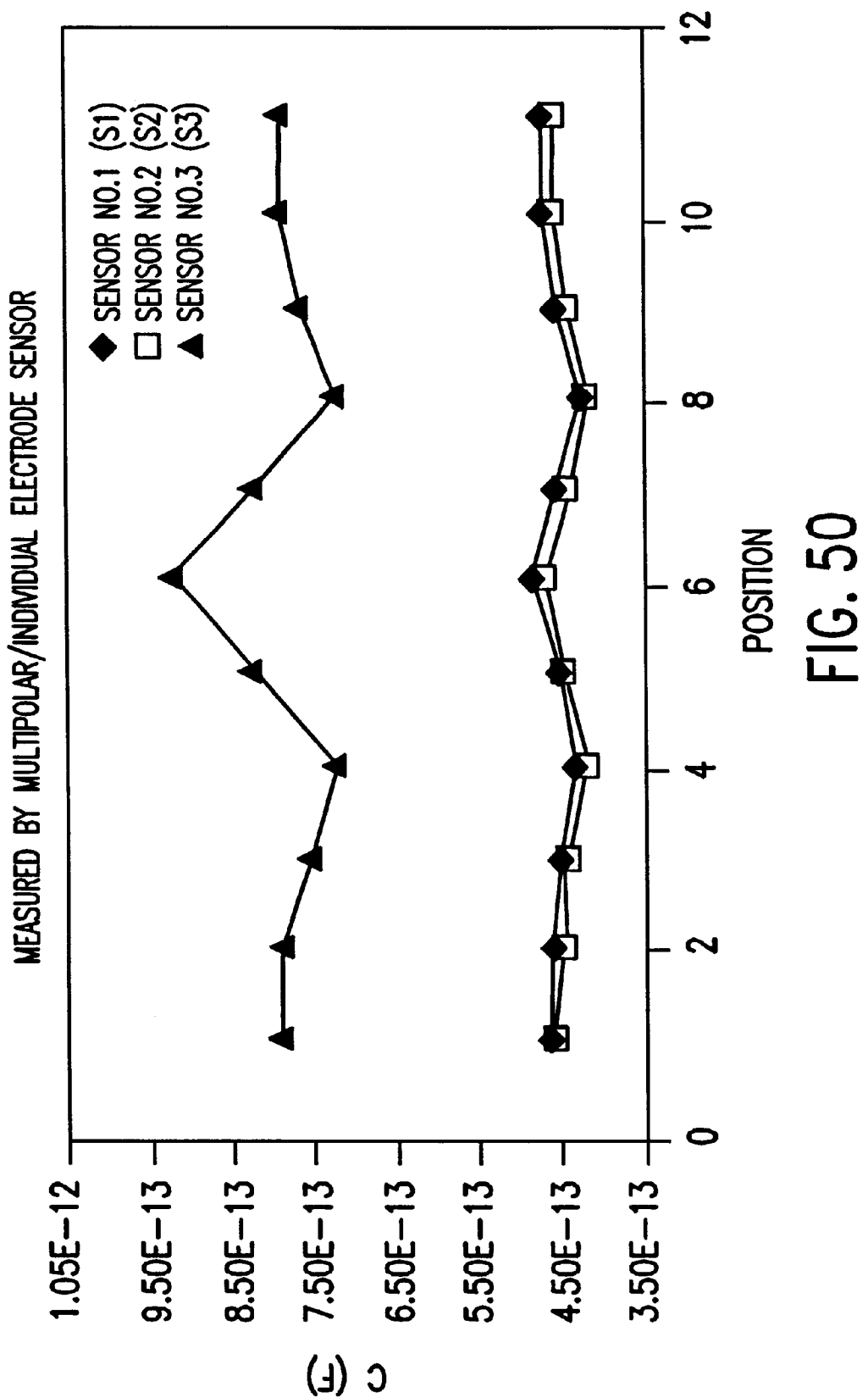
FIG. 50 is a graph showing the individual and resultant total capacitance measured with the multi-double-polar/individual electrode sensor versus position of the rice cake corresponding to FIG. 48.

(4) When the values measured with each pair of electrodes are added in the circuit, the resultant is added value of the individual value of capacitance (TABLE7, TABLE8, FIG. 48, FIG. 50).

The difference of the double-polar capacitance sensor on the same plane from the facing type sensor is that, in the former, a phenomenon that series/parallel circuit is formed between the electrode and the air layer and between the air and the article, is observed, when air layer exists under the projection plane of the electrodes. The former is supposed to effectively used for counting the number of articles and for controlling disarray of the same.

(IX) Capacitance Sensor with Anti-Dewing Device.

Phenomena such as dewing, icing, and frosting occurs on the surface of a sensor when used in a freezing/unfreezing apparatus. As the value of capacitance varies in response to these phenomena, proper measurement of capacitance of a food article is not possible. Here, the effect of addition of a heating device was verified. If a capacitance sensor is kept at temperature of about 0.1° C.~10° C., slightly higher than the dew point of environment air, dewing, icing or frosting is prevented.

Figure 17A:
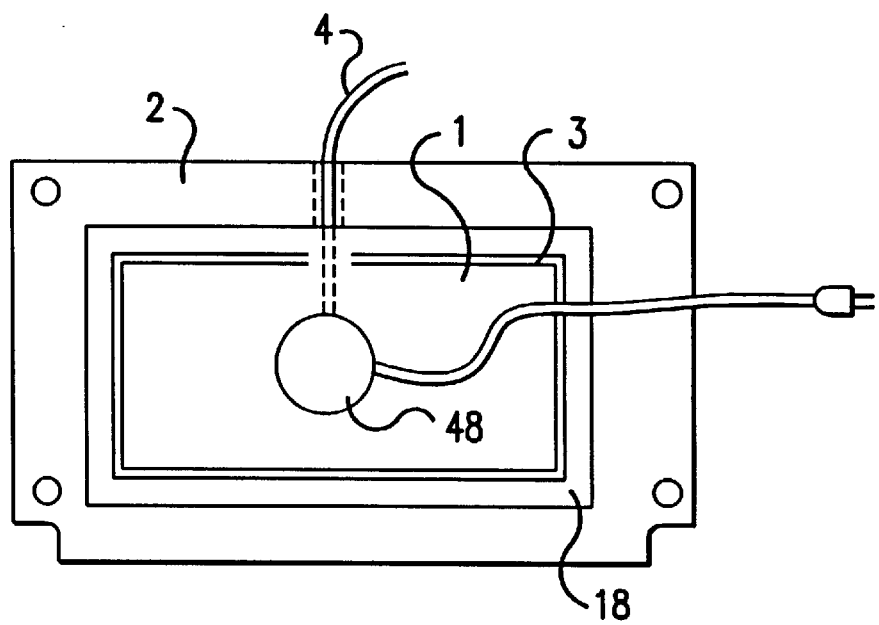
FIG. 17 is a schematic representation of the principal part of the positive electrode of an embodiment of a capacitance sensor with anti-dewing device according to the present invention; (A) is a plan view, (B) is a central vertical sectional view.
Figure 17B:
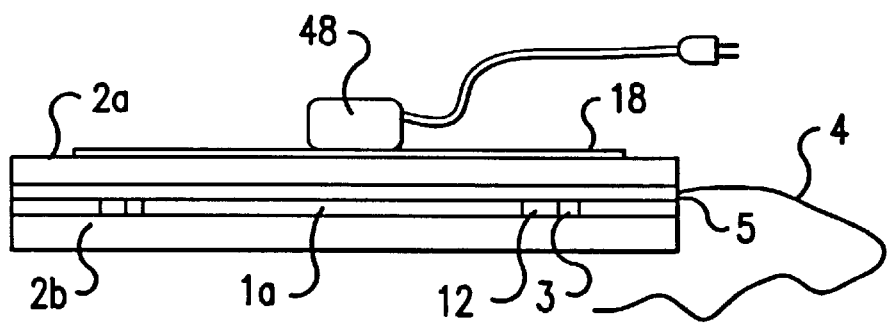

FIG. 17 is a schematic sketch of an embodiment of a capacitance sensor with anti-dewing device according to the present invention. An electric heater 48 is placed on the insulation plate 2a by the medium of a copper plate 18 for heating by commercial power source.

It is preferable to mount the electric heater 48 by the medium of the copper plate larger than the electrode plate 1 for prevention of low frequency electric noise and partial heating.

The copper plate 18 is provided on the surface contrary to the surface which faces the article to be measured of the capacitance sensor and the electric heater 48 is cemented thereto. Aluminum, stainless steel, copper plate may be used individually or in combination according to the kind of disturbance by the electric heater 48. To verify the effect of the device, measurement was carried away using a rice cake.

The method of measurement was as follows:

(1) Measurement with the sensor without the electric heater 48 and without icing in both cases a rice cake and air exist and only air exists.
(2) Measurement with the sensor provided with the electric heater 48 and without icing in both cases a rice cake and air exist and only air exists.
(3) Measurement with the sensor used in (2) iced and in two cases the power source of the heater is off and on.
(4) Measurement with the sensor used in (2) iced and placed in a refrigerator (−30° C.) where power was applied to the heater 48 for 21 minutes to sublimate the ice adhered to the sensor; the temperature of the sensor after sublimation of the ice was −28° C.

Result of Measurement.

(a) Apparent capacitance increases when the anti-icing device is mounted (TABLE 9). The increment is smaller when power is applied to the heater than when not supplied. In both cases the measurement was stable without fluctuations due to external electric disturbance. The difference of the capacitance between the case of air layer plus rice cake and air layer only is the same regardless of presence or absence of the anti-icing device, or supply or shut-off of power to the heater, when ice, dew, or frost is not adhered to the sensor. Accordingly, the increment in capacity can be treated as a bias or apparatus constant.

TABLE 9

| W or W/O Rice Cake | | Air Layer Only | Air Layer and Rice Cake |
|---|---|---|---|
| W or W/O Heater | Sensor Icing | Heat Power | |
| | | Off | On | Off | On |
| W/O Heater | Non-Iced | 4.120 | | 5.910 | |
| | | 10.8660 | 10.5270 | 12.2460 | 11.9050 |
| With Heater | Ice Crystal Adhered | 11.6600 | 11.3050 | | 12.1890 |
| | Ice Crystal Sublimated | 10.8620 | 10.5240 | | 11.9060 |

When dewing, icing, or frosting occurred on the sensor, the measurement value is influenced by the dewing, icing, or frosting regardless of whether the anti-frost device is powered or not. When the dew, ice or frost is removed by means of anti-icing device, the measurement value is recovered to that when dewing, icing, or frosting have not occurred.

When the anti-icing device is provided, the apparatus constant changes according to whether the device is powered or not. Therefore, it is necessary that apparatus constant is kept constant by using a self temperature-control type heater which is powered all the time during operation or the operational comparator section 61 (see FIG. 2 and FIG. 5) which adjust apparatus constant according to on or off of the heater power source, is provided.

(b) when adhered quantity of ice, dew, or frost is small, the measurement value of capacitance increases. According to another experiment, when the insulation between the metal part of the sensor support, article to be measured, and adjacent electrode is impaired owing to the adherence of grown ice, dew, or frost, the value decreases.

(c) In the case of a continuous freezing apparatus B, as the metal transfer surface works as other side electrode, the heater is not able to be mounted, and so change in capacitance is supposed if icing, dewing, or frosting occurs on the transfer surface. It is possible, in this case, to obtain the capacitance of the article (food) to be measured by subtracting the capacitance at the part where the article does not exist from the measured value at the part where the article exists. Also, contamination, icing, or dewing of the transfer surface can be detected by the change of capacitance.

From the above description it is clear that the sensor with anti-icing device is effective as a means for accurate measurement of capacitance under an environment in which icing, dewing, or frosting occurs.

Therefore, by the freezing/unfreezing system using a noncontact article temperature measuring device for food according to the present invention, it is possible to maintain the temperature of the environment gas (air, nitrogen, carbon dioxide, etc.) and its flow velocity in the freezing/unfreezing room 38 in the state most desirable in the process of freezing and unfreezing, through controlling the flow rate of heat medium, direction and rotation speed of the fan by means of the adjusting/setting section 62 (see FIG. 2 and FIG. 5) based on processed data in the operational comparator section 61 in which the capacitance of a food article measured with the noncontact capacitance sensor is compared with the most proper value and the change of capacitance with the lapse of time and the derivative of capacitance obtained beforehand about the food belonging to the same group as the food article to be measured.

When inclusion of foreign matter or existence of hollow is detected, proper control such as suspend of operation and exclusion of inadequate food article is carried out.

When applied to a continuous freezing/unfreezing apparatus, by information obtained from a plurality of the capacitance sensors disposed in each zone, control of the speed of motors in accordance with the transferring state and transfer speed of the food article is performed and proper operation control of the apparatus is achieved.

In the present invention, the principle that permittivity of food is one of physical quantity and that in an alternating current circuit with R, L, and C, when R and C are constant and for C is applied the capacitance of a food article as a dielectric material, the impedance of the circuit is determined by the permittivity of the food article. The capacitance of a food article is determined by the shape of the food article, i.e. its area facing the electrode and thickness, together with its permittivity, so the change in capacitance of the food article of the same shape is related to the permittivity. Impedance of the circuit is determined by resistance R, inductance L, capacitance C, and frequency of the voltage applied to the sensor. The output from the capacitance measuring section 61 can be taken out as capacitance, impedance, or permitivity, and any of them may be used for the evaluation of food.

Industrial Applicability

Through the use of the noncontact article temperature measuring device for food according to the present invention, the following will be realized:

(1) The internal state of an article to be measured can be determined without contact with and destruction of the article with high accuracy through the detection of the capacitance of the article and comparison of the detected capacitance with the beforehand measured correlation between the capacitance and temperature of the article of the same kind as the article to be measured, and hygienic, effective, and versatile control can effectively be performed in the process of freezing and unfreezing food.

(2) The whole apparatus is constructed small as the space required for mounting the sensor is small.

(3) The evaluation of quality such as the shape and temperature of the article on the steel belt of the continuous freezing/unfreezing apparatus, etc., and the evaluation of speed, etc. are performed with a single sensor at the same time; and the single sensor can deal with a number of measurement items to simplify the construction of the apparatus.

(4) The article to be measured is not damaged, as the measurement is performed without contact with and destruction of the article, differing from the conventional method of temperature measurement.

(5) Improvements in accuracy in freezing food, in manufacturing food, in quality control, in sanitary control of the apparatus are realized.

(6) The presence or absence of the internal hollow in the article is detected by the change in capacitance, enabling the quality control of the article.

(7) Improvement in the control of quality and sanitation is realized, as the inclusion of foreign matter is detected by the change in capacitance.

(8) Improvement in measurement accuracy is realized by using the capacitance sensor with anti-icing device, as, although the apparent capacity increases when measured with the sensor with anti-freezing device, the measurement value is stable uninfluenced by external disturbance and the increment of the capacitance can be treated as bias or apparatus constant.

(9) When the multi-polar sensor is used, particularly in a continuous freezing/unfreezing apparatus with electric conductive transferring member, the change of capacitance according to the size, pitch of disposition, and transfer speed of the food is grasped and proper control is possible according to these data.

What is claimed is:

1. A noncontact article temperature measuring device for food characterized in that; at least a pair of electrodes serving as a capacitance sensor, facing each other vertically across a space to compose a capacitance sensor, through or in which space an article of food is passed or placed in a noncontact state with the electrodes, and a capacitance measuring section for determining the capacitance of the food article located in the said space from the electric signal obtained from the pair of electrodes, are provided; and the determination of the article temperature including the food temperature, or frozen/thawed state, based on the detected capacitance when the predetermined voltage is applied to the paired electrodes, is made possible.

2. A noncontact article temperature measuring device for food according to claim 1, wherein the voltage applied to the positive electrode is that of high frequency of the range from 50 KHz to 1 MHz.

3. A noncontact article temperature measuring device for food according to claim 1, wherein a positive sensor electrode to which the predetermined voltage is applied is so composed that a guard electrode for preventing the diffusion of lines of electric force is provided around the periphery of the positive electrode with insulation spacing kept between them, the guard electrode being grounded.

4. A noncontact article temperature measuring device for food according to claim 1, wherein both the upper and lower faces of the positive sensor electrode are coated with substantial electric insulation material or the same is sandwiched with substantial electric insulators to be prevented from contacting with the food and humidity which are fluctuating factors of the environment.

5. A noncontact article temperature measuring device for food according to claim 3, wherein a counter electrode facing the positive sensor electrode across said space is formed of electric conductive material and constitute a part of food transferring face.

6. A noncontact article temperature measuring device for food according to claim 3, wherein a grounded noise filter is provided in the space above the positive sensor electrode located on the opposite side of the space for transferring food article.

7. A noncontact article temperature measuring device for food according to claim 1, wherein the evaluation of quality of food article such as presence/absence of internal deficiency and inclusion of foreign matter along with the evaluation of temperature, frozen/thawed state, through comparing the measurement data obtained in time sequence and processed in the capacitance measuring section with the standard data for the food article to be measured memorized in advance.

8. A noncontact article temperature measuring device for food according to claim 1, wherein, in the noncontact article temperature measuring device according to claim 1 applied to a continuous freezing/unfreezing apparatus in which an article of food is placed on a conveyor and frozen or unfrozen continuously, at least one side electrode of the pair of electrodes is a electric conductive transfer member constituting a part of the food transfer conveyor, the other side electrode is an electrode or a plurality of electrodes disposed above the former electrode across the space where the food article passes or is placed without contacting with the electrodes.

9. A noncontact article temperature measuring device for food according to claim 8, wherein a freezing/unfreezing room in which food is transferred by a conveyor is divided into a plurality of freezing/unfreezing zone, each zone is provided with a positive electrode, and the conveyor or a part of the conveyor is provided with a grounded electrode formed of belt shaped electric conductive material.

10. A noncontact article temperature measuring device for food according to claim 1, wherein the positive electrode of the pair of electrodes is a multi-polar sensor electrode composed of a plurality of electrodes, and the determination of article temperature including food temperature, or frozen/thawed state, is possible based on the signal from a selected electrode or a composite signal from combined electrodes among the plurality of the electrodes.

11. A noncontact article temperature measuring device for food according to claim 10, wherein the plurality of the electrodes are surrounded as a whole by a grounded guard electrode with insulation spacing between them for preventing the diffusion of lines of electric force.

12. A noncontact article temperature measuring device for food according to claim 10, wherein the evaluation of quality of food article such as shape and presence/absence of internal hollow is performed by selectively combining a plurality of capacitance signals obtained through measurement in which the direction and position of the food article to be measured are changed relative to the multi-polar sensor when the food passes by the sensor.

13. A noncontact article temperature measuring device for food characterized in that; a substantial electric insulator, on the surface of which a food article is disposed, is provided under the lower side of the space through or in which the food article passes or is placed in a noncontact state with the electrodes; on the upper side of the space is provided at least a pair of electrodes serving as a capacitance sensor; a capacitance measuring section for determining the capacitance of the food article located in said space from the electric signal obtained from the paired electrodes, is provided; and the measurement of the article temperature including the food temperature, or frozen/thawed state, based on the detected capacitance when the predetermined voltage is applied to the pair of electrodes, is made possible.

14. A noncontact article temperature measuring device for food according to claim 13, wherein the voltage applied to the pair of electrodes is that of high frequency of the range from 50 KHz to 1 MHz.

15. A noncontact article temperature measuring device for food according to claim 13, wherein the positive electrode to which the predetermined voltage is applied is so composed that a guard electrode for preventing diffusion of lines of electric force is provided around the positive electrode with insulation spacing kept between them, the guard electrode being grounded.

16. A noncontact article temperature measuring device for food according to claim 13, wherein both the upper and lower faces of the positive and negative electrodes arranged on the same plane are coated with substantial electric insulation material or the same are sandwiched with substantial electric insulators to be prevented from contacting with food and humidity which are fluctuating factors of the environment.

17. A noncontact article temperature measuring device for food according to claim 13, wherein the negative electrode on the said same plane is a common electrode which pairs up with the positive electrodes, the common electrode being grounded.

18. A noncontact article temperature measuring device for food characterized in that the device comprises; at least a pair of electrodes serving as a capacitance sensor, facing each other vertically across a space to compose a capacitance sensor, through or in which space an article of food is passed or placed in noncontact state with the electrodes; a capacitance measuring section for determining the capacitance of the food article located in the said space from the electric signal obtained from the paired electrodes; a means for heating the environment air in said space on the side facing the positive electrode of the paired electrodes; and that the determination of the article temperature including the food temperature, or frozen/thawed state, based on the detected capacitance, keeping the air temperature slightly higher than the dew point temperature, is made possible.

19. A noncontact article temperature measuring device for food characterized in that; a substantial electric insulator on the surface of which an article of food is disposed is provided under a space and on the upper side of the space is provided at least a pair of electrodes serving as a capacitance sensor, through or in which space the food article passes or placed in a noncontact state with the electrodes; a capacitance measuring section for determining the capacitance of the food article located in said space from the electric signal obtained from the paired electrodes, is provided; a means for heating the environment air in said space on the side facing the positive electrode of the paired electrodes, is provided; and the determination of the article temperature including the food temperature, or frozen/thawed state, based on the detected capacitance, keeping the air temperature slightly higher than the dew point, is made possible.

* * * * *